US008163710B2

(12) United States Patent
Kerr

(10) Patent No.: US 8,163,710 B2
(45) Date of Patent: *Apr. 24, 2012

(54) REDUCTION OF GRAFT-VERSUS-HOST DISEASE BY MODULATION OF SHIP ACTIVITY

(75) Inventor: William G. Kerr, Syracuse, NY (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/651,809

(22) Filed: Jan. 4, 2010

(65) Prior Publication Data
US 2010/0144841 A1 Jun. 10, 2010

Related U.S. Application Data

(63) Continuation of application No. 11/787,064, filed on Apr. 13, 2007, now Pat. No. 7,713,945, which is a continuation of application No. 10/097,101, filed on Mar. 14, 2002, now abandoned, which is a continuation-in-part of application No. 09/955,174, filed on Sep. 19, 2001, now abandoned.

(60) Provisional application No. 60/233,661, filed on Sep. 19, 2000, provisional application No. 60/314,099, filed on Aug. 23, 2001.

(51) Int. Cl.
*A61K 31/70* (2006.01)
(52) U.S. Cl. .................................................. 514/44 R
(58) Field of Classification Search ............. 435/6, 91.1, 435/91.31, 455; 514/1, 2, 44; 536/23.1, 536/24.5
See application file for complete search history.

(56) References Cited

U.S. PATENT DOCUMENTS

| 4,603,112 | A | 7/1986 | Paoletti et al. |
| 4,769,330 | A | 9/1988 | Paoletti et al. |
| 4,777,127 | A | 10/1988 | Suni et al. |
| 4,987,071 | A | 1/1991 | Cech et al. |
| 5,017,487 | A | 5/1991 | Stunnenberg et al. |
| 5,087,617 | A | 2/1992 | Smith |
| 5,093,246 | A | 3/1992 | Cech et al. |
| 5,116,742 | A | 5/1992 | Cech et al. |
| 5,135,917 | A | 8/1992 | Burch |
| 5,144,019 | A | 9/1992 | Rossi et al. |
| 5,166,057 | A | 11/1992 | Palese et al. |
| 5,168,053 | A | 12/1992 | Altman et al. |

(Continued)

FOREIGN PATENT DOCUMENTS
EP 0 345 242 A2 12/1989
(Continued)

OTHER PUBLICATIONS
Crooke, S., Ann. Rev. Medicine, vol. 55, pp. 61-95 (2004).*
(Continued)

*Primary Examiner* — Terra Cotta Gibbs
(74) *Attorney, Agent, or Firm* — Saliwanchik, Lloyd & Eisenschenk

(57) ABSTRACT

Inhibition of dendritic cell function in solid organ grafts or allogeneic bone marrow transplants prior to or during engraftment by blocking SH2-containing inositol phosphatase (SHIP) expression or function is taught as a method of abrogating immune rejection and thereby increasing the efficacy of engraftment of an allogeneic bone marrow transplant or solid organ allograft or xenograft. Also disclosed is a transgenic mouse having the genotype SHIP$^{-/-}$ which exhibits enhanced survival following mismatched allogeneic marrow grafts.

18 Claims, 18 Drawing Sheets

U.S. PATENT DOCUMENTS

| | | | |
|---|---|---|---|
| 5,176,996 | A | 1/1993 | Hogan et al. |
| 5,180,818 | A | 1/1993 | Cech et al. |
| 5,190,931 | A | 3/1993 | Inouye |
| 5,272,262 | A | 12/1993 | Rossi et al. |
| 5,804,412 | A | 9/1998 | Gill et al. |
| 6,025,198 | A | 2/2000 | Bennett et al. |
| 6,090,621 | A | 7/2000 | Kavanaugh et al. |
| 6,117,850 | A | 9/2000 | Patchen et al. |
| 6,200,807 | B1 | 3/2001 | Bennett et al. |
| 6,506,559 | B1 | 1/2003 | Fire et al. |
| 6,703,215 | B2 | 3/2004 | Erneux et al. |
| 7,691,821 | B2 | 4/2010 | Desponts et al. |
| 7,704,963 | B2 | 4/2010 | Kerr et al. |
| 7,713,945 | B2 * | 5/2010 | Kerr .................... 514/44 R |
| 7,763,592 | B1 | 7/2010 | Kerr et al. |
| 7,807,646 | B1 | 10/2010 | Kerr et al. |
| 8,008,273 | B2 | 8/2011 | Kerr et al. |
| 2002/0137711 | A1 | 9/2002 | Kerr |
| 2002/0165192 | A1 | 11/2002 | Kerr et al. |
| 2002/0193579 | A1 | 12/2002 | Usman et al. |
| 2003/0114401 | A1 | 6/2003 | Bennett et al. |
| 2003/0143732 | A1 | 7/2003 | Fosnaugh et al. |
| 2003/0166282 | A1 | 9/2003 | Brown et al. |
| 2004/0072298 | A1 | 4/2004 | Sauvageau et al. |
| 2004/0235765 | A1 | 11/2004 | Kerr et al. |
| 2004/0259247 | A1 | 12/2004 | Tuschl et al. |
| 2005/0054103 | A1 | 3/2005 | Peled et al. |
| 2006/0223749 | A1 | 10/2006 | Desponts et al. |
| 2007/0224124 | A1 | 9/2007 | Kerr et al. |
| 2008/0076731 | A1 | 3/2008 | Kerr |
| 2010/0136026 | A1 | 6/2010 | Kerr et al. |
| 2010/0183521 | A1 | 7/2010 | Kerr et al. |
| 2010/0260730 | A1 | 10/2010 | Kerr et al. |
| 2010/0266548 | A1 | 10/2010 | Kerr et al. |
| 2011/0052546 | A1 | 3/2011 | Desponts et al. |
| 2011/0064704 | A1 | 3/2011 | Kerr et al. |

FOREIGN PATENT DOCUMENTS

| | | |
|---|---|---|
| EP | 0 440 219 A1 | 8/1991 |
| GB | 2 200 651 A | 8/1988 |
| WO | WO 89/01973 A2 | 3/1989 |
| WO | WO 91/02805 A2 | 3/1991 |
| WO | WO 92/06693 A1 | 4/1992 |
| WO | WO 97/10252 A1 | 3/1997 |
| WO | WO 97/12039 A2 | 4/1997 |
| WO | WO 99/32619 A1 | 7/1999 |
| WO | WO 01/68836 A3 | 9/2001 |
| WO | WO 01/75164 A2 | 10/2001 |
| WO | WO 01/92513 A1 | 12/2001 |
| WO | WO 02/24233 A2 | 3/2002 |
| WO | WO 02/44321 A2 | 6/2002 |
| WO | WO 02/078614 A3 | 10/2002 |
| WO | WO 2008/022468 A1 | 2/2008 |
| WO | WO 2008/103648 | 8/2008 |
| WO | WO 2009/042910 A2 | 4/2009 |

OTHER PUBLICATIONS

Peracchi et al., Rev. Med. Virol., vol. 14, pp. 47-64 (2004).*
Agrawal et al., Molecular Med. Today., vol. 6, pp. 72-81 (2000).*
Chirila et al., Biomaterials, vol. 23, pp. 321-342 (2002).*
Opalinska et al., Nature Rev., vol. 1, pp. 503-514 (2002).*
Jang et al., Expert Rev. Medical Devices, vol. 1, No. 1, pp. 127-138 (2004).*
Paraiso et al. (The Journal of Immunology, 2007 vol. 178:2893-2900).*
Amarzguioui, M. et al. "An algorithm for selection of functional siRNA sequences" *Biochemical and Biophysical Reasearch Communications*, 2004, 316:1050-1058.
Ara, T. et al. "Long-Term Hematopoietic Stem Cells Require Stromal Cell-Derived Factor-1 for Colonizing Bone Marrow during Ontogeny" *Immunity*, Aug. 2003, 19:257-267.
Bagheri, S. et al. "Ribozymes in the Age of Molecular Therapeutics" *Current Molecular Medicine*, 2004, 4(5):489-506.
Brauweiler, A. et al. "Differential Regulation of B Cell Development, Activation, and Death by the Src Homology 2 Domain-containing 5' Inositol Phosphatase (SHIP)" *J. Exp. Med.*, May 1, 2000, 191(9):1545-1554.
Brummelkamp, T.R. et al. "A System for Stable Expression of Short Interfering RNAs in Mammalian Cells" *Science*, Apr. 19, 2002, 296:550-553.
Clawson, G.A. et al. "Inhibition of papilloma progression by antisense oligonucleotides targeted to HPV11 E6/E7 RNA" *Gene Therapy*, 2004, 11:1331-1341.
Clement, S. et al. "The lipid phosphatase SHIP2 controls insulin sensitivity" *Nature*, Jan. 4, 2001, 409:92-97.
Desponts, C. et al. "s-SHIP Associates with Receptor Complexes Essential for Pluripotent Stem Cell Growth and Survival" *Stem Cells and Development*, 2006, 15:641-646.
Gong, D. et al."Picking a winner: new mechanistic insights into the design of effective siRNAs"*TRENDS in Biotechnology*, Sep. 2004, 22(9):451-454.
Grassi, G. et al. "Therapeutic Potential of Hammerhead Ribozymes in the Treatment of Hyper-Proliferative Diseases" *Current Pharmaceutical Biotechnology*, 2004, 5(4):369-386.
Hazen, A.L. et al. "SHIP is required for a functional hematopoietic stem cell niche" *Blood*, Mar. 26, 2009, 113(13):2924-2933.
Helgason, C.D. et al."A Dual Role for Src Homology 2 Domain-containing Inositol-5-Phosphatase (SHIP) in Immunity: Aberrant Development and Enhanced Function of B Lymphocytes in SHIP-/- Mice" *J. Exp. Med.*, Mar. 6, 2000, 191(5):781-794.
Hendry, P. et al."Redesigned and chemically-modified hammerhead ribozymes with improved activity and serum stability" *BMC Chemical Biology*, Dec. 9, 2004, 4(1):1-11.
Huber, M. et al. "Targeted disruption of SHIP leads to Steel factor-induced degranulation of mast cells" *The EMBO Journal*, 1998, 17(24):7311-7319.
Kerr, W.G. "Role of SHIP in Stem Cell Biology: Seed or Soil?" Presented at the University of Minnesota Stem Cell Institute, held Sep. 26, 2007, Minneapolis, Minnesota, 48 pages.
Kerr, W.G. "A Role for SHIP in Stem Cell Biology and Transplantation" Presented at The Walter and Eliza Hall Institute of Medical Research, held Oct. 24, 2008, at the Melbourne Town Hall, Melbourne, VIC, Australia, 2 pages.
Kerr, W.G. "A Role for SHIP in Stem Cell Biology and Transplantation" *Current Stem Cell Research & Therapy*, 2008, 3(2):99-106.
Khvorova, A. et al. "Functional siRNAs and miRNAs Exhibit Strand Bias" *Cell*, Oct. 17, 2003, 115:209-216.
Kim, B. et al. "Inhibition of Ocular Angiogenesis by siRNA Targeting Vascular Endothelial Growth Factor Pathway Genes" *American Journal of Pathology*, Dec. 2004, 165(6):2177-2185.
Lioubin, M. et al. "p150Ship, a signal transduction molecule with inositol polyphosphate-5-phosphatase activity" *Genes & Development*, 1996, 10:1084-1095.
Liu, Y. et al. "Scaffolding Protein Gab2 Mediates Differentiation Signaling Downstream of Fms Receptor Tyrosine Kinase" *Molecular and Cellular Biology*, May 2001, 21(9):3047-3056.
McManus, M.T. et al. "Gene Silencing in Mammals by Small Interfering RNAs" *Nature Reviews*, Oct. 2002, 3:737-747.
Mittal, V. "Improving the Efficiency of RNA Interference in Mammals" *Nature Reviews*, May 2004, 5:355-365.
Miyagishi, M. et al."U6 promoter-driven siRNAs with four uridine 3' overhangs efficiently suppress targeted gene expression in mammalian cells" *Nature Biotechnology*, May 2002, 19:497-500.
Pancoska, P. et al. "Efficient RNA interference depends on global context of the target sequence: quantitative analysis of silencing efficiency using Eulerian graph representation of siRNA" *Nucleic Acids Research*, 2004, 32(4):1469-1479.
Pesesse, X. et al. "Identification of a Second SH2-Domain-Containing Protein Closely Related to the Phosphatidylinositol Polyphosphate 5-Phosphatase SHIP" *Biochemical and Biophysical Research Communications*, 1997, 239:697-700.
Petit, I. et al. "G-CSF induces stem cell mobilization by decreasing bone marrow SDF-I and up-regulating CXCR4" *Nature Immunology*, Jul. 2002, 3(7):687-787.
Rauh, M.J. et al. "SHIP Represses the Generation of Alternatively Activated Macrophages"*Immunity*, Oct. 2005, 23:361-374.
Reynolds, A. et al. "Rational siRNA design for RNA interference" *Nature Biotechnology*, Mar. 2004, 22(3):326-330.

Sattler, M. et al. "SHIP1, an SH2 Domain Containing Polyinositol-5-phosphatase, Regulates Migration through Two Critical Tyrosine Residues and Forms a Novel Signaling Complex with DOK1 and CRKL" *J. Biol. Chem.*, Jan. 26, 2001, 276(4):2451-2458.
Schubert, S. et al. "Local RNA Target Structure Infuences siRNA Efficacy: Systematic Analysis of Intentionally Designed Binding Regions" *J. Mol. Biol.*, 2005, 883-893.
Schwarz, D.S. et al. "Asymmetry in the Assembly of the RNAi Enzyme Complex" *Cell*, Oct. 17, 2003, 115:199-208.
Semerad, C.L. et al. "G-CSF potently inhibits osteoblast activity and CXCL12 mRNA expression in the bone marrow" *Blood*, Nov. 1, 2005, 106(9):3020-3027.
Sly, L.M. et al. "LPS-Induced Upregulation of SHIP Is Essential for Endotoxin Tolerance" *Immunity*, Aug. 2004, 21:227-239.
Ui-Tei, K. et al. "Guidelines for the selection of highly effective siRNA sequences for mammalian and chick RNA interference" *Nucleic Acid Research*, 2004, 32(3):936-948.
Wahle, J.A. et al. "Cutting Edge: Dominance by an MHC-Independent Inhibitory Receptor Compromises NK Killing of Complex Targets" *J. Immunol.*, 2006, 176:7165-7169.
Wahle, J.A. et al. "Inappropriate Recruitment and Activity by the Src Homology Region 2 Domain-Containing Phosphatase 1 (SHP1) Is Responsible for Receptor Dominance in the SHIP-Deficient NK Cell" *J. Immunol.*, 2007, 179:8009-8015.
Wright, D.E. et al. "Physiological Migration of Meatopoietic Stem and Progenitor Cells" *Science*, Nov. 30, 2001, 294:1933-1936.
Yuan, B. et al. "siRNA Selection Server: an automated siRNA oligonucleotide prediction server" *Nucleic Acids Research*, 2004, 32:W130-W134, Web Server Issue.
Zhang, J. et al. "Identification of the haematopoietic stem cell niche and control of the niche size" *Nature*, Oct. 23, 2003, 425:836-841.
Zhang, J. et al. "PTEN maintains haemotopoietic stem cells and acts in lineage choice and leukaemia prevention" *Nature*, May 25, 2006, 441:518-522.
Genbank Accenssion No. NM_001017915 (May 13, 2005), pp. 1-8.
Genbank Accenssion No. NM_005541 (Sep. 25, 2007), pp. 1-7.
Genbank Accenssion No. NM_010566 (Sep. 24, 2007), pp. 1-7.
Genbank Accenssion No. U55192 (Jan. 14, 1997), pp. 1-3.
Office Action mailed May 2, 2011 in U.S. Appl. No. 12/883,470, filed Sep. 16, 2010.
Office Action mailed Dec. 8, 2011 in U.S. Appl. No. 12/670,360, filed Feb. 10, 2010.
Abreu, M.T. et al. "Translational Research in Inflammatory Bowel Disease" *Mount Sinai Journal of Medicine*, Dec. 2006, 73(8):1067-1073.
Avecilla, S.T. et al. "Chemokine-mediated interaction of hematopoietic progenitors with the bone marrow vascular niche is required for thrombopoiesis" *Nature Medicine*, Jan. 2004, 10(1):64-71.
Bernstein, E. et al. "The rest is silence" *RNA*, 2001, 7:1509-1521.
Bernstein, E. et al. "Role for a bidentate ribonuclease in the initiation step of RNA interference". *Nature*, Jan. 2001, 409:363-366.
Best, W.R. "Predicting the Chron's Disease Activity Index From the Harvey-Bradshaw Index"*Inflamm Bowel Dis*, Apr. 2006, 12(4):304-310.
Brooks, R. et al., "SHIP1 Inhibition Increases Immunoregulatory Capacity and Triggers Apoptosis of Hematopoietic Cancer Cells" *J. Immuno.*, 2010, 184:3582-3589.
Browning, B.L. et al. "Has Toll-Like Receptor 4 Been Premature Dismissed as an Inflammatory Bowel Disease Gene? Association Study Combined with Meta-Analysis Shows Strong Evidence for Association" *American Journal of Gastroenterology*, Nov. 2007, 102(11):2504-2512.
Carthew, R.W. "Gene silencing by double-stranded RNA" *Current Opinion in Cell Biology*, 2001, 13:244-248.
Chae, S.S. et al. "Requirement for sphingosine 1-phosphate receptor-1 in tumor angiogenesis demonstrated by in vivo RNA interference" *The Journal of Clinical Investigation*, 2004, 114(8):1082-1089.
Chernock, R.D. etal. "SHP2 and cbl participate in α-chemokine receptor CXCR4-mediated signaling pathways" *Blood*, Feb. 1, 2001, 97(3):608-615.

Chiu, Y.L. et al. "RNAi in Human Cells: Basic Structural and Functional Features of Small Interfering RNA" *Molecular Cell*, Sep. 2002, 10(3):549-561.
Clemens, J.C. et al. "Use of double-stranded RNA interference in *Drosophila* cell lines to dissect signal transduction pathways" *PNAS*, 2000, 97:6499-6503.
Desponts, C. et al. "SHIP deficiency enhances HSC proliferation and survival but compromises homing and repopulation" *Blood*, 2006, 107(11):4338-4345.
De Jager, P.L. et al. "The role of the Toll receptor pathway in susceptibility to inflammatory bowel diseases" *Genes and Immunity*, 2007, 8:387-397.
Dorn, G. et al. "siRNA relieves chronic neuropathic pain" *Nucleic Acids Research*, 2004, 32:e49.
Drachman, J.G. et al. "Dissecting the thrombopoietin receptor: Functional elements of the Mpl cytoplasmic domain" *Proc Natl Acad Sci USA*, Mar. 1997, 94(6):2350-2355.
Drachman, J.G. et al. "Thrombopoietin Signal Transduction in Purified Murine Megakaryocytes" *Blood*, Jan. 15, 1997, 89(2):483-492.
De Fougerolles, A. et al. "RNA interference In Vivo: Toward Synthetic Small Inhibitory RNA-Based Therapeutics" *Methods in Enzymology: RNA Interference*, 2005, 392:278-296.
Fuchs, U. et al. "Silencing of Disease-related Genes by Small Interfering RNAs" *Current Molecular Medicine*, 2004, 4:507-517.
Fukata, M. etal. "Toll-Like Receptor-4 Promotes the Development of Colitis-Associated Colorectal Tumors" *Gastroenterology*, 2007, 133(6):1869-1881.
Fukata, M. et al. "TLR4 signalling in the intestine in health and disease" *Biochemical Society Transactions*, 2007, 35:1473-1478.
Geddis, A.E. et al. "Phosphatidylinositol 3-Kinase Is Necessary but Not Sufficient for Thrombopoietin-induced Proliferation in Engineered Mpl-bearing Cell Lines as Well as in Primary Megakaryocytic Progenitors" *The Journal of Biological Chemistry*, Sep. 14, 2001, 276(37):34473-34479.
Genbank Accession No. AAG48558.2 (Nov. 5, 2001), pp. 1-3.
Genbank Accession No. AF216648 (Nov. 5, 2001), pp. 1-5.
Genbank Accession No. AF467287 (Aug. 7, 2002), pp. 1-5.
Genbank Accession No. BC064834.1 (Jan. 3, 2005), pp. 1-4.
Genbank Accession No. EAX04996 (Dec. 18, 2006), pp. 1-5.
Giuriato, S. et al. "Tyrosine Phosphorylation and Relocation of SHIP Are Integrin-mediated in Thrombin-stimulated Human Blood Platelets" *The Journal of Biological Chemistry*, Oct. 24, 1997, 272(43):26857-26863.
Giurato, S. et al. "SH2-containing inositol 5-phosphatases 1 and 2 in blood platelets: their interactions and roles in the control of phosphatidylinositol 3,4,5-trisphosphate levels" *Biochemical Journal*, 2003, 276:199-207.
Gribar, S.C. et al. "The role of epithelial Toll-like receptor signaling in the pathogenesis of intestinal inflammation" *Journal of Leukocyte Biology*, Mar. 2008, 83:493-498.
Gupta, N. et al. "Negative Signaling Pathways of the Killer Cell Inhibitory Receptor and FcγRllb1 Require Distinct Phosphatases" *The Journal of Experimental Medicine*, Aug. 4, 1997, 186(3):473-478.
Gupta, S. et al. "Inducible, reversible, and stable RNA interference in mammalian cells" *Proc Natl Acad Sci USA*, Feb. 4, 2004, 101(7). 1927-1932.
Hamada, T. et al. "Transendothelial Migration of Megakaryocytes in Response to Stromal Cell-derived Factor 1 (SDF-1) Enhances Platelet Formation" *The Journal of Experimental Medicine*, Aug. 3, 1998, 188(3):539-548.
Hattori, K. et al. "Plasma elevation of stromal cell-derived factor-1 induces mobilization of mature and immature hematopoietic progenitor and stem cells" *Blood*, Jun. 1, 2001, 97(11):3354-3360.
Hume, G.E. et al. "Novel NOD2 Haplotype Strengthens the Association Between TLR4 Asp299Gly and Crohn's Disease in an Australian Population" *Inflammatory Bowel Diseases*, 2008, 14(5):585-590.
Hutvagner, G. et al. "RNAi: nature abhors a double-strand" *Current Opinion in Genetics & Development*, 2002, 12:225-232.
Ichim, T.E. et al. "RNAa Interference: A Potent Tool for Gene-Specific Therapeutics" *American Journal of Transplantation*, 2004, 4(8):1227-1236.

Jana, S. et al. "RNA interference: potential therapeutic targets" *Appl Microbiol Biotechnol*, 2004, 65(6):649-657.

Kaplan, J. et al. "Chediak-Higashi syndrome" *Current Opinion in Hematology*, 2008, 15:22-29.

Karrasch, T. et al. "NF-κB and the Intestine: Friend or Foe?" *Inflamm Bowel Dis*, 2008, 14:114-124.

Kaushansky, K. et al. "Promotion of megakaryocyte progenitor expansion and differentiation by the c-Mpl ligand thrombopoietin" *Nature*, Jun. 16, 1994, 369(6481):568-571.

Kaushanksy, K. "Review Article: Drug Therapy: Thrombopoietin" *The New England Journal of Medicine*, Sep. 10, 1998, 339(11):746-754.

Kerr, W.G. et al. "Analysis of lipopolysaccharide-response genes in B-lineage cells demonstrates that they can have differentiation stage-restricted expression and contain SH2 domains" *Proc Natl Acad Sci USA*, Apr. 1996, 93:3947-3952.

Kisielow, M. et al. "Isoform-specific knockdown and expression of adaptor protein ShcA using small interfering RNA" *Biochem J.*, 2002, 363(1):1-5.

Kim, C.H. et al. "Altered responsiveness to chemokines due to targeted disruption of SHIP" *The Journal of Clinical Investigation*, Dec. 1999, 104(12):1751-1759.

Komarova, E.A. et al. "p53 is a suppressor of inflammatory response in mice" *The FASEB Journal*, Jun. 1, 2005, 19(8):1030-1032.

Lee, N. S. et al. "Expression of small interfering RNAs targeted against HIV-1 rev transcripts in human cells" *Nature Biotechnology*, May 2002, 20:500-505.

Liu, L. et al. "Multiple Cytokines Stimulate the Binding of a Common 145-Kilodalton Protein to the Shc at the Grb2 Recognition Site of Shc" *Molecular and Cellular Biology*, Oct. 1994, 14(10):6926-6935.

Lok, S. et al. "Cloning and expression of murine thrmbopoietin cDNA and stimulation of platelet production in vivo" *Nature*, Jun. 16, 1994, 369(6481):565-568.

Mailand, N. et al. "Deregulated human Cdc14a phosphatase disrupts centrosome separation and chromosome segregation" *Nature Cell Biology*, 2002, 4(4):317-322.

Matzke, M. et al. "RNA: Guiding Gene Silencing" *Science*, 2001, 293:1080-1083.

McManus, M.T. et al. "Gene silencing using micro-RNA designed hairpins" *RNA*, Jun. 2002, 8(6):842-850.

Narayan, S. et al. "Role of APC and DNA mismatch repair genes in the development of colorectal cancers" *Molecular Cancer*, Dec. 2003, 2:41, 15 pages.

Nykanen, A. et al. "ATP Requirements and small Interfering RNA Structure" *Cell*, Nov. 2001, 107:309-321.

Office Action mailed Oct. 12, 2010 in U.S. Appl. No. 12/819,711, filed Jun. 21, 2010.

Paddison, P.J. et al. "Short hairpin RNAs (shRNAs) induce sequence-specific silencing in mammalian cells" *Genes & Development*, 2002, 16:948-958.

Paul, C.P. et al. "Effective expression of small interfering RNA in human cells" *Nature Biotechnology*, May 2002, 20:505-508.

Perez, L.E. et al. "Increased plasma levels of stromal-derived factor-1 (SDF-1/CXCL12) enhance human thrombopoiesis and mobilize human colony-forming cells (CFC) in NOD/SCID mice" *Experimental Hematology*, Mar. 2004, 32(3):300-307.

Plasterk, R.H.A., "RNA Silencing: The Genome's Immune System" *Science*, 2002, 296:1263-1265.

Ryther, R.C.C. et al. "siRNA therpeutics: big potential from small RNAs" *Gene Therapy*, 2005, 12(1):5-11.

Sandborn, W.J. et al. "MMX Multi Matrix System® mesalazine for the induction fo remission inpatients with mild-to-moderate ulcerative colitis: a combined analysis of two randomized, double-blind, placebo-controlled trials" *Alimentary Pharmacology & Therapeutics*, 2007, 26(2):205-215.

Scadden, A.D.J. "RNAi is antagonized by A→I hyper-editing" *EMBO Reports*, 2001, 11(2):1107-1111.

Scherr, M. et al. "Inhibition of GM-CSF Receptor Function by Stable RNA Interference in a NOD/SCID Mouse Hematopoietic Stem Cell Transplantation Model" *Oligonucleotides*, Oct. 2003, 13(5): 353-363.

Sharp, P.A. "RNAi and double-strand RNA" *Genes & Development*, 1999, 13:139-141.

Sharp, P.A. "RNA interference—2001" *Genes & Development*, 2001, 15:485-490.

Shen, W.G. "RNA interference and its current application in mammals" *Chinese Medical Journal*, 2004, 117(7):1084-1091.

Song, E. et al. "RNA interference targeting Fas protects mice from fulminant hepatitis" *Nature Medicine*, 2003, 9(3):347-351.

Soutschek, J. et al. "Therapeutic silencing of an endogenous gene by systemic administration of modified siRNAs"' *Nature*, Nov. 2004, 432:173-178.

Sui, G. et al. "A DNA vector-based RNAi technology to suppress gene expression in mammalian cells" *Proc Natl Acad Sci USA*, Apr. 16, 2002, 99(8):5515-5520.

Takaku, H. "Gene silencing of HIV-1 by RNA interference" *Antiviral Chemistry & Chemotherapy*, 2004, 15:57-65.

Takeshita, S. et al. "SHIP-deficient mice are severely osteoporotic due to increased numbers of hyper-resorptive osteoclasts" *Nature Medicine*, Sep. 2002, 8(9):943-949.

Tridandapani, S. etal. "Src Homology 2 Domain-Containing Inositol Polyphosphate Phosphatase Regulates NF-78 B-Mediated Gene Transcription by Phagocytic Fc γRs in Human Myeloid Cells" *The Journal of Immunology*, Oct. 15, 2002, 169(8):4370-4378.

Tuschl, T. "Expanding small RNA interference" *Nature Biotechnology*, 2002, 20:446-448.

Van Limbergen, J. et al. "The Genetics of Inflammatory Bowel Disease" *American Journal of Gastroenterology*, 2007, 102:2820-2831.

Wadhwa, R. et al. "Know-how of RNA interference and its applications in research and therapy" *Mutation Research: Reviews in Mutation Research*, 2004, 567:71-84.

Wang, J.F. et al. "The α-Chemokine Receptor CXCR4 Is Expressed on the Megakaryocyte Lineage From Progenitor to Platelets and Modulates Migration and Adhesion" *Blood*, Aug. 1, 1998, 92(3):756-764.

Wang, J.W. et al. "Deregulated expression of LRBA facilitates cancer cell growth" *Oncogene*, Apr. 2004, 23:4089-4097.

Wang, N. et al. "BEACH Family of Proteins: Phylogenetic and Functional Analysis of Six Dictyostelium Beach Proteins" *Journal of Cellular Biochemistry*, 2002, 86:561-570.

Yu, J.Y. et al. "RNA interference by expression of short-interfering RNAs and hairpin RNAs in mammalian cells" *PNAS USA*, Apr. 2002, 99(9):6047-6052.

Zamore, P.D. "RNA interference: listening to the sound of silence" *Nature Structural Biology*, Sep. 2001, 8(9):746-750.

Zamore, P.D. "Ancient Pathways Programmed by Small RNAs" *Science*, 2002, 296(5571):1265-1269.

Zeng, Y. et al. "Both Natural and Designed Micro RNAs Can Inhibit the Expression of Cognate mRNAs When Expressed in Human Cells" *Molecular Cell*, Jun. 2002, 9:1327-1333.

Zhang, X. et al. "Small Interfering RNA Targeting Heme Oxygenase-1 Enhances Ischemia-Reperfusion-induced Lung Apoptosis" *The Journal of Biological Chemistry*, Mar. 2004, 279(11):10677-10684.

Zheng, B.J. et al. "Prophylactic and therapeutic effects of small interfering RNA targeting SARS-coronavirus" *Antiviral Therapy*, 2004, 9(3):365-374.

Zimmerman, T.S. et al. "RNAi-mediated gene silencing in non-human primates" *Nature*, May 2006, 441:111-114.

U.S. Appl. No. 10/605,452, Kerr et al.

U.S. Appl. No. 10/709,801, Desponts et al.

U.S. Appl. No. 10/904,667, Kerr at al.

U.S. Appl. No. 11/451,004, Kerr et al.

Office Action mailed Jan. 14, 2009 in U.S. Appl. No. 09/955,174, filed Sep. 19, 2001.

Office Action mailed Dec. 29, 2005 in U.S. Appl. No. 09/955,174, filed Sep. 19, 2001.

Office Action mailed Aug. 9, 2005 in U.S. Appl. No. 10/605,452, filed Sep. 30, 2003.

Office Action mailed Oct. 17, 2006 in U.S. Appl. No. 10/605,452, filed Sep. 30, 2003.

Office Action mailed Apr. 28, 2009 in U.S. Appl. No. 10/709,801, filed May 28, 2004.

Office Action mailed Sep. 22, 2008 in U.S. Appl. No. 10/709,801, filed May 28, 2004.
Office Action mailed Jan. 7, 2009 in U.S. Appl. No. 10/904,667, filed Nov. 22, 2004.
Office Action mailed Apr. 7, 2009 in U.S. Appl. No. 11/451,004, filed Jun. 12, 2006.
Adams, A. "RNA Therapeutics Enter Clinical Trials" *The Scientist*, Jan. 17, 2005, 19(1):1-4.
Agrawal, S. "Antisense oligonucleotides: towards clinical trials" *Tibtech*, Oct. 1996, 14:376-387.
Agrawal, N. et al. "RNA Interference: Biology, Mechanism, and Applications" *Microbiology and Molecular Biology*, Dec. 2003, 67(4):657-685.
Ahmed, N. at al. "Cytokine-Induced Expansion of Human $CD34^+$ Stem/Progenitor and $CD34^+CD41^+$ Early Megakaryocytic Marrow Cells Cultured on Normal Osteoblasts" *Stem Cells*, 1999, 17:92-99.
Akagi, K. et al. "Cre-mediated somatic site-specific recombination in mice" *Nucleic Acids Research*, 1997, 25(9):1766-1773.
Bender, M.A. et al. "Description and Targeted Deletion of 5' Hypersensitive Site 5 and 6 of the Mouse β-Globin Locus Control Region" *Blood*, Dec. 1998, 92(11):4394-4403.
Berkner, K.L. "Development of adenovirus vectors for the expression of heterologous genes" *BioTechniques*, 1988, 6(7):616-627.
Bjorklund, L.M. et al. "Embryonic stem cells develop into functional dopaminergic neurons after transplantation in a Parkinson rat model" *PNAS*, Feb. 19, 2003, 99(4):2344-2349.
Bolland, S. et al. "SHIP Modulates Immune Receptor Responses by Regulating Membrane Association of Btk" *Immunity*, Apr. 1998, 8:509-516.
Bonetta, L. "RNAi: Silencing never sounded better" *Nature Methods*, Oct. 2004, 1(1):79-86.
Braasch, D.A. et al. "Novel Antisense and Peptide Nucleic Acid Strategies for Controlling Gene Expression" *Biochemistry*, Apr. 9, 2002, 41(14):4503-4510.
Branch, A.D. "A good antisense molecule is hard to find" *Trends in Biochem Sci*, Feb. 1998, 23:45-50.
Caillaud, C. et al. "Adenoviral vector as a gene delivery system into cultured rat neuronal and glial cells" *Eur. J. Neurosci.*, 1993, 5:1287-1291.
Cantley, L.C. et al. "Oncogenes and Signal Transduction" *Cell*, Jan. 25, 1991, 64:281-302.
Caplen, N.J. et al. "Specific inhibition of gene expression by small double-stranded RNAs in invertebrate and vertebrate systems" *PNAS*, Aug. 14, 2001, 98(17):9742-9747.
Caplen, N.J. "RNAi as a gene therapy approach" *Expert Opinion Biol Ther.*, 2003, 3(4):575-586.
Crooke, S.T. "Basic principles of antisense therapeutics" in Antisense Research and Application, Chapter 1, pp. 1-50, S. Crooke, Editor, Springer-Verlag, 1999.
Damen, J.E. et al. "The 145-kDa protein induced to associate with Shc by multiple cytokines is an inositol tetraphosphate and phosphatidylinositol 3,4,5-trisphosphate 5-phosphatase" *Proc Natl Acad Sci USA*, Feb. 1996, 93:1689-1693.
Desponts, C. et al. "MHC Class I inhibitory receptors on natural killer cells recruit SHIP in an attempt to control cell survival" *FASEB Journal*, Mar. 20, 2002, 16(4):A707, abstract.
De Souza, A.T. et al. "Transcriptional and phenotypic comparisons of Ppara knockout and siRNA knockdown mice" *Nucleic Acids Research*, 2006, 34(16):4486-4494.
Elbashir, S.M. etal. "RNA interference is mediated by 21-and 22-nucleotide RNAs" *Genes & Development*, 2001, 15:188-200.
Elbashir, S.M. et al. "Duplexes of 21-nucleotide RNAs mediate RNA interference in cultured mammalian cells" *Nature*, May 2001, 411:494-498.
Evans, D.J. et al. "An engineered poliovirus chimaera elicits broadly reactive HIV-1 neutralizing antibodies" *Nature*, Jun. 1989, 339:385-388.
Examination Report dated Nov. 11, 2006 in European Application No. 01973144.7.
Fire, A. et al. "Potent and specific genetic interference by double-stranded RNA in *Caenorhabditis elegans*" *Nature*, Feb. 1998, 391:806-811.

Fisher-Hoch, S.P. et al. "Protection of rhesus monkeys from fatal Lassa fever by vaccination with a recombinant vaccinia virus containing the Lassa virus glycoprotein gene" *Proc Natl Acad Sci USA*, Jan. 1989, 86:317-321.
Flexner, C. et al. "Attenuation and immunogenicity in primates of vaccinia virus recombinants expressing human interleukin-2" *Vaccine*, 1990, 8, 17-21.
Geier, S.J. et al. "The Human SHIP Gene Is Differentially Expressed in Cell Lineages of the Bone Marrow and Blood" *Blood*, 1997, 89:1876-1885.
Gewirtz, A.M. et al. "Facilitating oligonucleotide delivery: Helping antisense deliver on its promise" *Proc Natl Acad Sci USA*, Apr. 1996, 93:3161-3163.
Ghansah, T. et al. "A role for the SH2-containing Inositol phosphatase in the biology of natural killer cells and stem cells" in Activating and inhibitory immunoglobulin-like Receptors, 2001, pp. 129-140.
Ghansah, T. et al. "Target disruption of Src homology 2-containing 5' inositol phosphatase murine natural killer cells" *FASEB Journal*, Mar. 20, 2002, 16(4):A706, abstract.
Ghansah, T. Of al. "The Src homology 2 containing inositol phosphatase is vital for the function and homeostasis of Natural Killer cells" *FASEB Journal*, Mar. 7, 2001, 15(4):A655, abstract.
Ghansah, T. et al. "Expansion of Myeloid Suppressor Cells in SHIP-Deficient Mice Represses Allogeneic T Cell Responses" *The Journal of Immunology*, 2004, 173:7324-7330.
Guzman, R.J. et al. "Molecular and cellular cardiology/receptors: efficient and selective adenovirus-mediated gene transfer into vascular neointima" *Circulation*, 1993, 88(6):2838-2848.
Guzman, R.J. et al. "Efficient and Selective Adenovirus-Mediated Gene Transfer Into Vascular Neointima" *Circulation*, Dec. 1993, 88(6):2838-2848.
Hannon, G.J. et al. "Unlocking the potential of the human genome with RNA interference" *Nature*, Sep. 16, 2004, 431:371-378.
Harborth, J. et al. "Identification of essential genes in cultured mammalian cells using small interfering RNAs" *Journal of Cell Science*, 114(24):4557-4565, (2001).
Hawkins, P.T. et al. "Platelet-derived growth factor stimulates synthesis of $PtdIns(3,4,5)P_3$ by activating a $PtdIns(4,5)P_2$ 3-OH kinase" *Nature*, Jul. 1992, 358(6382):157-159.
Held, W. et al. "Transgenic Expression of the Ly49A Natural Killer Cell Receptor Confers Class I Major Histocompatibility Complex (MHC)-specific Inhibition and Prevents Bone Marrow Allograft Rejection" *J Exp Med*, Nov. 1996, 184:2037-2041.
Helgason, C.D. et al. "Targeted disruption of SHIP leads to homopoietic perturbations, lung pathology, and a shortened life span" *Genes & Development*, 1998, 12:1610-1620.
Helgason, C.D. et al. "Homeostasis and regeneration of the hematopoietic stem cell pool are altered in SHIP-deficient mice" *Blood*, 2003, 102(10):3541-3547.
Hemann, M.T. et al. "An epi-allelic series of p53 hypomorphs created by stable RNAi produces distinct tumor phenotypes in vivo" *Nature Genetics*, Mar. 2003, 33:396-400.
Hemmati-Brivanlou, A. et al. "Vertebrate Embryonic Cells Will Become Nerve Cells Unless Told Otherwise" *Cell*, Jan. 10, 1997, 88:13-17.
Huber, M. et al. "The src homology 2-containing inositol phosphatase (SHIP) is the gatekeeper of mast cell degranulation" *Proc Natl Acad Sci USA*, Sep. 1998, 95:11330-11335.
Huber, M. et al. "The role of SHIP in growth factor induced signalling" *Progress in Biophysics & Molecular Biology*, 1999, 71:423-434.
Jaffe, H.A. et al. "Adenovirus-mediated in vivo gene transfer and expression in normal rat liver" *Nat. Genet.*, 1992, 1:372-378.
Jefferson, A.B. et al. "Properties of Type II Inositol Polyphosphate 5-Phosphatase" *The Journal of Biological Chemistry*, Apr. 1995, 270(16):9370-9377.
Jen, K.Y. et al. "Suppression of Gene Expression by Targeted Disruption of Messenger RNA: Available Options and Current Strategies" *Stem Cells*, 2000, 18:307-319.
Jolly, D. "Viral vector systems for gene therapy" *Cancer Gene Therapy*, 1994, 1(1):51-64.

Kapeller, R. et al. "Phosphatidylinositol 3-Kinase" *BioEssays*, 1994, 16:565-576.

Kass-Eisler, A. et al. "Quantitative determination of adenovirus-mediated gene delivery to rat cardiac myocytes in vitro and in vivo" *Proc Natl Acad Sci USA*, Dec. 1993, 90:11498-11502.

Kawasaki, H. etal. "Induction of Midbrain Dopaminergic Neurotechnique Neurons from ES Cells by Stromal Cell-Derived Inducing Activity" *Neuron*, Oct. 2000, 28:31-40.

Kerr, W.G., "The SH2 Containing Inositol Phosphatase (SHIP) is a Crucial Regulator of NK Cell Repertoire and Function" Abstract #34, presented at Core Research for Evolutional Science and Technology (CREST) International Symposium on Immunoglobulin-like Receptors, held Sep. 19-20, 2000, at the Sendai International Center, Sendai City, Japan.

Kerr, W.G. et al. "Critical role for SHIP in engraftment of histo-incompatible stem cells" *Oncology Research*, 2001, 12:285.

Kim, J.H. et al. "Dopamine neurons derived from embryonic stem cells function in an animal model of Parkinson's disease" *Nature*, Jun. 20, 2002, pp. 1-7, doi.1038/nature00900, advance online publication.

Kit, S. "Recombinant-derived modified-live herpesvirus vaccines" *Immunobiology of Proteins and Peptides V Vaccines: Mechanisms, Design, and Applications*, Atassi, M.Z. Ed. Plenum Press, New York, 1989, 215:219-236.

Klippel, A. et al. "Membrane Localization of Phosphatidylinositol 3-Kinase Is Sufficient to Activate Multiple Signal-Transducing Kinase Pathways" *Molecular and Cellular Biology*, Aug. 1996, 16(8):4117-4127.

Koh, C.Y. et al. "Augmentation of antitumor effects by NK cell inhibitory receptor blockade in vitro and in vivo" *Blood*, 2001, 97(10):3132-3137.

Kolls, J. et al. "Prolonged and effective blockade of tumor necrosis factor activity through adenovirus-mediated gene transfer" *Proc Natl Acad Sci USA*, Jan. 1994, 91:215-219.

Krystal, G. et al. "Molecules in focus: SHIPs ahoy" *The International Journal of Biochemistry & Cell Biology*, 1999, 31:1007-1010.

Lanier, L.L. "NK Cell Receptors" *Annu Rev Immunol*, 1998, 16:359-393.

Levrero, M. et al. "Defective and nondefective adenovirus vectors for expressing foreign genes in vitro and in vivo" *Gene*, 1991, 101:195-202.

Li, Q. et al. "Assessment of recombinant adenoviral vectors for hepatic gene therapy" *Hum. Gene Ther.*, 1993, 4:403-409.

Liu, L. et al. "The Src Homology 2 (SH2) Domain of SH2-containing Inositol Phosphatase (SHIP) Is Essential for Tyrosine Phosphorylation of SHIP, Its Association with Shc, and Its Induction of Apoptosis" *The Journal of Biological Chemistry*, Apr. 4, 1997, 272(14):8983-8988.

Liu, Q. et al. "Molecular Cloning and Chromosomal Localization in Human and Mouse of the SH2-Contianing Inositol Phosphatase, *INPP5D* (SHIP)" *Genomics*, 1997, 39:109-112.

Liu, Q. et al. "The Inositol Polyphosphate 5-Phosphatase Ship Is a Crucial Negative Regulator of B Cell Antigen Receptor Signaling" *J Exp Med*, Oct. 5, 1998, 188(7):1333-1342.

Liu, Q. etal. "SHIP is a negative regulator of growth factor receptor-mediated PKB/Akt activation and myeloid cell survival" *Genes & Development*, 1999, 13(7):786-791.

Lotzova, E. et al. "Prevention of Rejection of Allogeneic Bone Marrow Transplants by NK-1.1 Anti Serum" *Transplantation*, 1983, 35(5):490-494, abstract.

Lucas, D.M. et al. "A Novel Spliced Form of SH2-Containing Inositol Phosphatase is Expressed During Myeloid Development" *Blood*, Mar. 15, 1999, 93:6):1922-1933.

Luytjes, W. et al. "Amplification, expression, and packaging of a foreign gene by influenza virus" *Cell*, 1989, 59:1107-1113.

McMichael, A.J. et al. "Cytotoxic T-cell immunity to influenza" *N. Eng. J. Med.*, 1983, 309(1):13-17.

Mendelson, E. et al. "Expression and rescue of a nonselected marker from an integrated AAV vector" *Virol.*, 1988, 166:154-165.

Montgomery, M.K. et al. "RNA as a target of double-stranded RNA-mediated genetic interference in *Caenorhabditis elegans*" *Proc Natl Acad Sci USA*, Dec. 1998, 95:15502-15507.

Moody, J.L. et al. "Anemia, thrombocytopenia, leukocytosis, extramedullary hematopoiesis, and impaired progenitor function in Pten+/−SHIP−/− mice: a novel model of myelodysplasia" *Blood*, 2004, 103:4503-4510.

Muraille, E. et al. "Distribution of the Src-homology-2-domain-containing inositol 5-phosphatase SHIP-2 in both non-haemopoietic and haemopoietic cells and possible involvement of SHIP-2 in negative signaling of B-cells" *Biochem J*, 1999, 342:697-705.

Moss, B. et al, "Vaccinia virus expression vectors" *Ann. N.Y. Acad. Sci.*, 1989, 569:86-103.

Mulligan, R.C. et al. "Synthesis of rabbit β-globin in cultured monkey kidney cells following infection with a SV40 β-globin recombinant genome" *Nature*, 1979, 277:108-114.

Munroe, S.S. et al. "Subgenomic RNA sequence of human astrovirus supports classification of astroviridae as a new family" *J. Vir.*, 1993, 67(6):3611-3614.

Novina, C.D. et al, "The RNAi revolution" *Nature*, Jul. 8, 2004, 430:161-164.

Okada, H. et al. "Cutting Edge: Role of the Inositol Phosphatase SHIP in B Cell Receptor-Induced Ca2+ Oscillatory Response" *The Journal of Immunology*, 1998, 161:5129-5132.

Odorico, J.S. et al. "Multilineage Differentiation from Human Embryonic Stem Cell Lines" *Stem Cells*, 2001, 19:193-204.

Overbaugh, J. et al. "Molecular Cloning of a Feline Leukemia Virus That Induces Fatal Immunodeficiency Disease in Cats" *Science*, 1988, 239:906-910.

Palu, G. et al. "In pursuit of new developments for gene therapy of human diseases" *Journal of Biotechnology*, 1999, 68:1-13.

Paroo, Z. et al. "Challenges for RNAi in vivo" *TRENDS in Biotechnology*, Aug. 2004, 22(8):390-394.

Pasquet, J.M. et al. "Phosphatidylinositol 3,4,5-trisphosphate regulates Ca2+ entry via Btk in platelets and megakaryocytes without increasing phospholipase C activity" *EMBO Journal*, Jun. 15, 2000, 19(12):2793-2802.

Pera, M.F. et al. "Commentary: Human embryonic stem cells" *Journal of Cell Science*, 2000, 113:5-10.

Pesesse, X. et al, "The SH2 domain containing inositol 5-phosphatase SHIP2 displays phosphatidylinositol 3,4,5-trisphosphate and inositol 1,3,4,5-tetrakisphosphate 5-phosphatase activity" *FEBS Letters*, 1998, 437:301-303.

Pihl-Carey, K. "Disease Drug fails in Phase III" *BioWorld Today*, Dec. 16, 1999, 10:1-2.

Poznansky, M. et al. "Gene Transfer into Human Lymphocytes by a Defective Human Immunodeficiency Virus Type 1 Vector" *Journal of Virology*, Jan. 1991, 65(1):532-536.

Program and Abstracts for CREST International Symposium on Immunoglobulin-like Receptors, held Sep. 19-20, 2000, 77 pages.

Puente, X.S. et al. "Human and Mouse Proteases: A Comparative Genomic Approach" *Nature Reviews: Genetics*, Jul. 2003, 4:544-558.

Rauh, M.J. et al. "The role of SHIP1 in macrophage programming and activation" *Biochemical Society Transactions*, 2004, 32(5):785-788.

Rehli, M. et al. "The Membrane-Bound Ectopeptidase CPM as a Marker of Macrophage Maturation In Vitro and In Vivo" *Cellular Peptidases in Immune Functions and Diseases 2*, 2000, pp. 205-216, eds. Lagner and Ansorge, Kluwer Academic/Plenum Publishers.

Rohrschneider, L.R. et al. "Structure, function, and biology of SHIP proteins" *Genes & Development*, 2000, 14:505-520.

Rosenfeld, M.A. et al. "Adenovirus-mediated transfer of a recombinant α1-antitrypsin gene to the lung epithelium in vivo" *Science*, 1991, 252:431-434.

Ruggeri, L. et al. "Role of Natural Killer Cell Alloreactivity in HLA-Mismatched Hematopoietic Stem Cell Transplantation" *Blood*, Jul. 1, 1999, 94(1):333-339.

Sabin, A.B. et al. "History of Sabin attenuated poliovirus oral live vaccine strains" *Journal of Biological Standardization*, 1973, 1:115-118.

Samulski, R.J. et al. "Helper-Free Stocks of Recombinant Adeno-Associated Viruses: Normal Integration Does Not Require Viral Gene Expression" *Journal of Virology*, Sep. 1989, 63(9):3822-3828.

Sawyers, C.L. "Chronic Myeloid Leukemia" *The New England Journal of Medicine*, Apr. 29, 1999, 340(17)1330-1340.

Sly, L.M. et al. "SHIP, SHIP2, and PTEN activities are regulated in vivo by modulation of their protein levels: SHIP is up-regulated in macrophages and mast cells by lipopolysaccharide" *Experimental Hematology*, 2003, 31:1170-1181.

Statement of Dr. Toshiyuki Takai dated Apr. 10, 2007, an organizer of the CREST International Symposium on Immunoglobulin-like Receptors, held Sep. 19-20, 2000, 1 page.

Stephens, L.R. etal. "Agonist-stimulated synthesis of phasphatidylinositol(3,4,5)- trisphosphate: a new intracellular signalling system?" *Biochimica et Biophysica Acta*, 1993, 1179:27-75.

Svoboda, P. et al. "Selective reduction of dormant maternal mRNAs in mouse oocytes by RNA interference" *Development*, 2000, 127:4147-4156.

Tamm, I. et al. "Antisense therapy in oncology: new hope for an old Idea?" *Lancet*, 2001, 358:489-497.

Tu, Z. et al. "Embryonic and hematopoietic stem cells express a novel SH2-containing inositol 5'-phosphatase isoform that partners with the Grb2 adapter protein" *Blood*, 2001, 98:2028-2038.

Tuschl, T. et al. "Targeted mRNA degradation by double-stranded RNA in vitro" *Genes & Development*, 13:3191-3197, (1999).

Tuschl, T. "RNA Interference and Small Interfering RNAs" *ChemBioChem*, 2001, 2:239-245.

Verfaillie, C.M. et al. "Hematopoietic stem cells for transplantation" *Nature Immunology*, 2002, 3(4):314-317.

Vincent, N. et al. "Long-term correction of mouse dystrophic degeneration by adenovirus-mediated transfer of a minidystrophin gene" *Nat. Genet.*, 1993, 5:130-134.

Wang, C.Y. et al. "pH-sensitive immunoliposomes mediate target-cell-specific delivery and controlled expression of a foreign gene in mouse" *Proc Natl Acad Sci USA*, Nov. 1987, 84:7851-7855.

Wang, J.W. et al. "Influence of SHIP on the NK Repertoire and Allogeneic Bone Marrow Transplantation" *Science*, Mar. 15, 2002, 295(5562):2094-2097.

Ware, M.D. et al. "Cloning and Characterization of Human Ship, the 145-kD Inositol 5-Phosphatase That Associates With SHC After Cytokine Stimulation" *Blood*, Oct. 15, 1996, 88(8):2833-2840.

Wisniewski, D. et al. "Neoplasia: A Novel SH2-Containing Phosphatidylinositol 3,4,5- Trisphosphate 5-Phosphatase (SHIP2) Is Constitutively Tyrosine Phosphorylated and Associated With src Homologous and Collagen Gene (SHC) in Chronic Myelogenous Leukemia Progenitor Cells" *Blood*, Apr. 1999, 93(8):2707-2720.

Wolf, I. et al. "Cloning of the Genomic Locus of Mouse SH2 Containing Inositol 5-Phosphatase (SHIP) and a Novel 110-kDA Splice Isoform, SHIPδ" *Genomics*, 2000, 69:104-112.

Yap, K.L. et al. "Transfer of specific cytotoxic T lymphocytes protects mice inoculated with influenza virus" *Nature*, 1978, 273:238-239.

Yokoyama, W.M. et al. "Natural killer cell receptors" *Current Opinion in Immunology*, 1998, 10:298-305.

Zabner, J. at al. "Adenovirus-mediated gene transfer transiently corrects the chloride transport defect in nasal epithelia of patients with cystic fibrosis" *Cell*, 1993, 75:207-216.

Zamore, P.D. etal. "RNAi:Double-Stranded RNA Directs the ATP-Dependent Cleavage of mRNa at 21 to 23 Nucleotide Intervals" *Cell*, Mar. 31, 2000, 101:25-33.

Zandstra, P.W. et al. "Leukemia Inhibitory Factor (LIF) Concentration Modulates Embryonic Stem Cell Self-Renewal and Differentiation Independently of Proliferation" *Biotechnol Bioeng*, 2000, 69:607-617.

Zwaka, T.P. et al. "Homologous recombination in human embryonic stem cells" *Nature Biotechnology*, Feb. 10, 2003, pp. 1-3, doi: 10.1038/nbt788, advance online publication.

Office Action mailed Feb. 10, 2006 in U.S. Appl. No. 10/097,101, filed Feb. 14, 2002.

Office Action mailed Apr. 12, 2006 in U.S. Appl. No. 10/605,452, filed Sep. 30, 2003.

Office Action mailed Jul. 22, 2009 in U.S. Appl. No. 10/904,667 filed Nov. 22, 2004.

Office Action mailed Sep. 28, 2009 in U.S. Appl. No. 11/451,004, filed Jun. 12, 2006.

Office Action mailed Aug. 5, 2008 in U.S. Appl. No. 11/451,004, filed Jun. 12, 2006.

Office Action mailed Jun. 5, 2009 in U.S. Appl. No. 11/787,064, filed Apr. 13, 2007.

Office Action mailed Dec. 16, 2008 in U.S. Appl. No. 11/787,064, filed Apr. 13, 2007.

Notice of Allowance mailed Oct. 7, 2009 in U.S. Appl. No. 11/787,064, filed Apr. 13, 2007.

Barton, G.M. et al. "Retroviral delivery of small interfering RNA into primary cells" *PNAS*, Nov. 12, 2002, 99(23):14943-14945.

Collazo, M.M. et al. "SHIP limits immunoregulatory capacity in the T-cell compartment" *Blood*, 2009, 113(13):2934-2944.

Donzé, O. et al. "RNA interference in mammalian cells using siRNAs synthesized with T7 RNA polymerase" *Nucleic Acids Research*, 2002, 30(10):e46, 4 pages.

Kim, V.N. "RNA Interference in Functional Genomics and Medicine" *J Korean Med Sci*, 2003, 18:309-318.

Krichevsky, A.M. et al. "RNAi functions in cultured mammalian neurons" *PNAS*, Sep. 2002, 99(18):11926-11929.

Lewis, D.L. et al. "Efficient delivery of siRNA for inhibition of gene expression in postnatal mice" *Nature Genetics*, Sep. 2002, 32:107-108.

McManus, M.T. et al. "Small Interfering RNA-Mediated Gene Silencing in T Lymphocytes" *The Journal of Immunology*, 2002, 169:5754-5760.

Milhavet, O. et al. "RNA Interference in Biology and Medicine" *Pharmacological Reviews*, 2003, 55(4):629-648.

Oliveira, D.M. et al. "Transient RNA interference in hematopoietic progenitors with functional consequences" *Genesis*, Aug. 2003, 36(4):203-208, abstract.

Paraiso, K.H.T. et al. "Induced SHIP Deficiency Expands Myeloid Regulatory Cells and Abrogates Graft-versus-Host Disease" *The Journal of Immunology*, 2007, 178(5):2893-2900.

Peng, Y. et al. "Silencing Expression of the Catalytic Subunit of DNA-dependent Protein Kinase by Small Interfering RNA Sensitizes Human Cells for Radiation-induced Chromosome Damage, Cell Killing, and Mutation" *Cancer Research*, Nov. 15, 2002, 62:6400-6404.

Perez, L.E. et al. "$SH_2$-Inositol Phosphatase 1 Negatively Influences Early Megakaryocyte Progenitors" *PLOS One*, Oct. 2008, 3(10):e3565, pp. 1-8.

Reich, S.J. etal. "Small interfering RNA (siRNA) targeting *VEGF* effectively inhibits ocular neovascularization in a mouse model" *Molecular Vision*, May 2003, 9:210-216.

Sauer, B. "Inducible Gene Targeting in Mice Using the Cre/*lox* System" *METHODS: A Companion to Methods in Enzymology*, 1998, 14:381-392.

Tuschl, T. et al. "Small Interfering RNAs: A Revolutionary Tool for the Analysis of Gene Function and Gene Therapy" *Molecular Interventions*, 2002, 2(3):158-167.

Wang, J.W. et al. Identification of a Novel Lipopolysaccharide-Inducible Gene with Key Features of Both a Kinase Anchor Proteins and chs1/beige Proteins, *The Journal of Immunology*, 2001, 166:4586-4595.

Yang, D. et al. "Short RNA duplexes produced by hydrolysis with *Escherichia coli* Rnase III mediate effective RNA interference in mammalian cells" *PNAS*, Jul. 2002, 99(15):9942-9947.

* cited by examiner

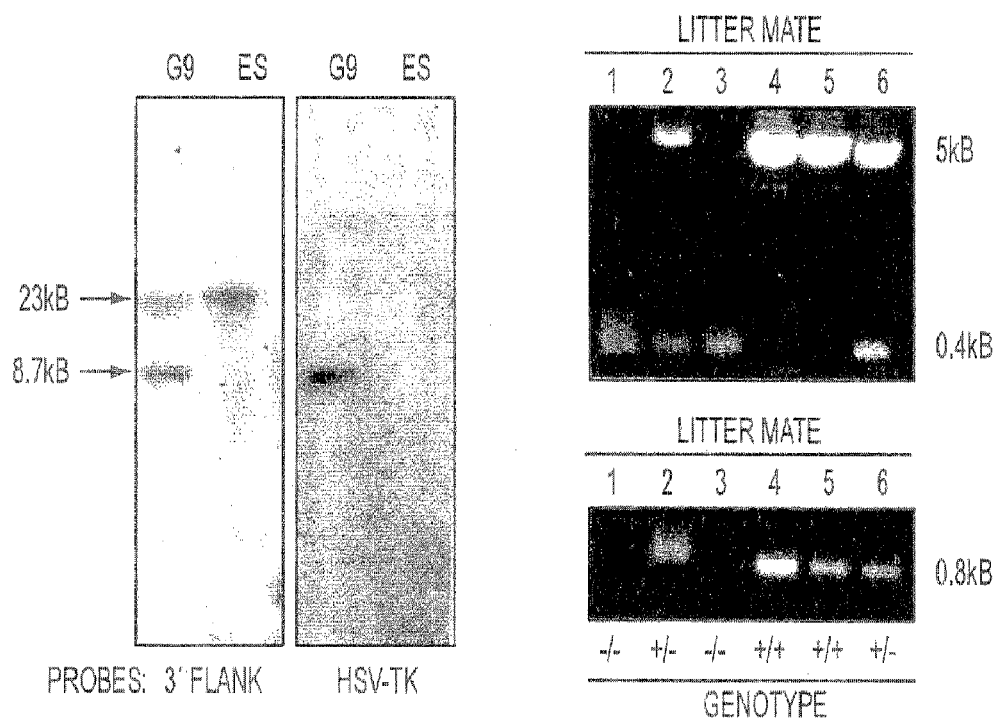
FIG. 1B
FIG. 1C
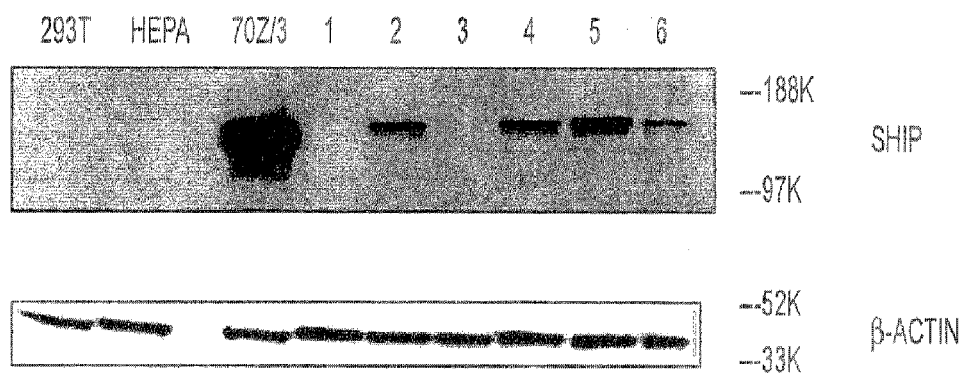
FIG. 1D

US 8,163,710 B2

REDUCTION OF GRAFT-VERSUS-HOST DISEASE BY MODULATION OF SHIP ACTIVITY

CROSS-REFERENCE TO RELATED APPLICATION

The present application is a continuation of U.S. application Ser. No. 11/787,064, filed Apr. 13, 2007, now U.S. Pat. No. 7,713,945, which is a continuation of U.S. application Ser. No. 10/097,101, filed Mar. 14, 2002, now abandoned, which is a continuation-in-part of U.S. application Ser. No. 09/955,174, filed Sep. 19, 2001, now abandoned, which claims the benefit of U.S. Provisional Application Ser. Nos. 60/233,661, filed Sep. 19, 2000 and 60/314,099, filed Aug. 23, 2001, each of which is hereby incorporated by reference herein in its entirety, including any figures, tables, nucleic acid sequences, amino acid sequences, and drawings.

GOVERNMENT SUPPORT

This invention was made with government support under grant DK54767awarded by the National Institutes of Health and National Institute of Diabetes and Digestive and Kidney Diseases, and by grant NS27405 awarded by the National Institute of Neurological Disorders and Stroke. The government has certain rights in the invention.

FIELD OF THE INVENTION

This invention relates to the hematopoietic-specific SH2-containing Inositol Polyphosphatase (SHIP) and its effect in modulating Natural Killer (NK) cell function and survival. Specifically, genetic and pharmaceutical methods are disclosed for the modulation of SHIP activity in order to influence NK cell function. The invention further relates to methods for decreasing immune rejection of histo-incompatible bone marrow grafts and solid organ allografts or xenografts, and methods for screening substances or genetic constructions for their ability to modulate SHIP activity.

BACKGROUND OF THE INVENTION

Activation of phosphatidylinositol 3'-kinase (PI 3-kinase) by growth factors and oncogenes has been implicated as a critical step in mitogenic signaling, cellular transformation, and in the prevention of cell death (apoptosis), as described in Cantley et al., Cell 64:281-302 (1991), Kapeller and Cantley. Bioessays 16:565-76 (1994), and Stephens et al, Biochim BiophysActa 1179:27-75 (1993). PI 3-kinase consists of 85 kDa and 110 kDa subunits which associate with receptor tyrosine kinases, other receptors and intracellular signaling molecules in response to survival signals, treatment with growth factors or in normal or transformed cells. Blockade of PI 3-kinase function either by mutagenesis or with pharmacological inhibitors prevents mitogenic signaling and can enhance apoptosis by blocking the activation of Akt/Protein Kinase B. Further, two products of PI 3-kinase, PtdIns(3,4,5)P$_3$ (PIP3) and PtdIns/3,4)P$_2$, increase in cells treated with mitogenic stimuli, as shown by Hawkins, et al. Nature 358: 157-910, (1992) and Klippel et al, Molecular and Cellular Biology 16:4117-4127 (1996). The products of PI 3-kinase are presumed to act as second messengers, as regulators of protein-protein interactions, or recruit other kinases that phosphorylate downstream effectors of PI3K signaling.

Thus, engagement of receptors on the surface of mammalian cells results in the activation of phosphatidylinositol 3-phosphate kinase (PI-3 kinase) and phosphorylation of inositol phospholipids on the cytoplasmic side of the membrane. The generation of phosphatidyl inositol (3,4,5) triphosphate (PIP3) by PI-3 kinase contributes to the activation of signaling pathways that drive cell proliferation and/or prevent apoptosis. Removal of the phosphate group from the D5 position of phosphoinositides by the hematopoietic-specific SH2-containing Inositol Polyphosphatase (SHIP) has been identified as an important negative feedback mechanism influencing cell activation and survival in the mammalian hematolymphoid compartment.

SHIP was originally identified based on its ability to bind Shc, Grb2, the FcγRIIB receptor, and by a gene-trapping approach. Through the use of in vitro assays, it was demonstrated that SHIP can remove the 5'-phosphate of PIP3 and inositol 1,3,4,5-tetrakisphosphate (IP4) suggesting that SHIP may counteract the activity of PI-3 kinase or prevent the sustained influx of Ca$^{2+}$ into the cell. The tyrosine phosphorylation and membrane recruitment of SHIP in response to receptor stimulation has been demonstrated in a variety of transformed hematolymphoid cell lines. Following activation of hematopoietic cells, SHIP is recruited to the membrane for better access to key substrates. In addition, mounting genetic evidence indicates that SHIP plays an important role in vivo as a negative regulator of cell activation in B lymphoid cells, myeloid cells, and mast cells. For example, one study demonstrated that SHIP$^{-/-}$ mice, although viable and fertile, failed to thrive, displaying only a 40% survival rate by 14 weeks of age. Mortality was associated with extensive consolidation of the lungs resulting from infiltration of myeloid cells. Increased numbers of granulocytes-macrophage progenitors were observed in both the bone marrow and spleen. Helgason, C D et al. (1998) "Targeted disruption of SHIP leads to hemopoietic perturbations, lung pathology, and a shortened life span." Genes Dev. 12(11):1610-20. In another study, SHIP$^{-/-}$ mast cells were found to be more prone to mast cell degranulation than SHIP-/+ or +/+ cells. Huber, M. et al (1998) "The src homology 2-containing inositol phosphatase (SHIP) is the gatekeeper of mast cell degranu)ation." Proc. Natl. Acad Sci USA 95(19):11330-5. In a third study, SHIP$^{-/-}$ mice exhibited chronic hyperplasia of myeloid cells which resulted in splenomegaly, lymphadenopathy, and myeloid infiltration of vital organs. Further, neutrophils and bone marrow-derived mast cells from these mice were less susceptible to programmed cell death induced by various apoptotic stimuli or by growth factor withdrawal. Liu, Q. et al. (1999) "SHIP is a negative regulator of growth factor receptor-mediated PKB/Akt activation any myeloid cell survival." Genes Dev. 13(7):789-91; Liu, Q. et al. (1998) "The inositol polyphoshate 5-phosphatase SHIP is a crucial negative regulator of B cell antigen receptor signalling." J Exp Med 188(7): 1333-42.

Together, these results demonstrate that SHIP is an important regulator of cellular responses in mature cells of certain hematopoietic lineages. The above studies were conducted with knockout mice using the traditional approach of neomycin replacement of exon I of the SHIP gene.

Inositol polyphosphate 5-phosphatases were the subject of U.S. Pat. No. 6,090,621 to Kavanaugh et al. "Signaling inositol polyphosphate 5-phosphatases (SIPS)"; PCT WO9710252A1 to Rohrschneidcr, L. R. "DNA encoding an SH2-inositol phosphatase, a SHC binding protein"; and PCT WO9712039A2 to Krystal, G. "SH2 containing inositol phosphatase."

None of the aforementioned studies have identified a role for SHIP in NK (natural killer) cell function, nor have these studies identified a role for NK cells in graft-versus-hosts disease (GVHD). It would be advantageous for reasons disclosed and described below, to control the activity of SHIP. Methods for controlling SHIP activity, and the benefits and treatments that the instant invention provides in improving bone marrow and solid organ transplants, potentially abrogating marrow graft and solid organ rejection, together with means for screening for substances that modulate SHIP activity, and more, are contained herein as will become apparent to one of skill in the art upon reading the following disclosure.

BRIEF DESCRIPTION OF THE FIGURES

FIG. 7(A-C) illustrates the rejection of "missing self," but not histo-incompatible, bone marrow grafts by $SHIP^{-/-}$ mice.

SUMMARY OF THE INVENTION

Figure 1A:
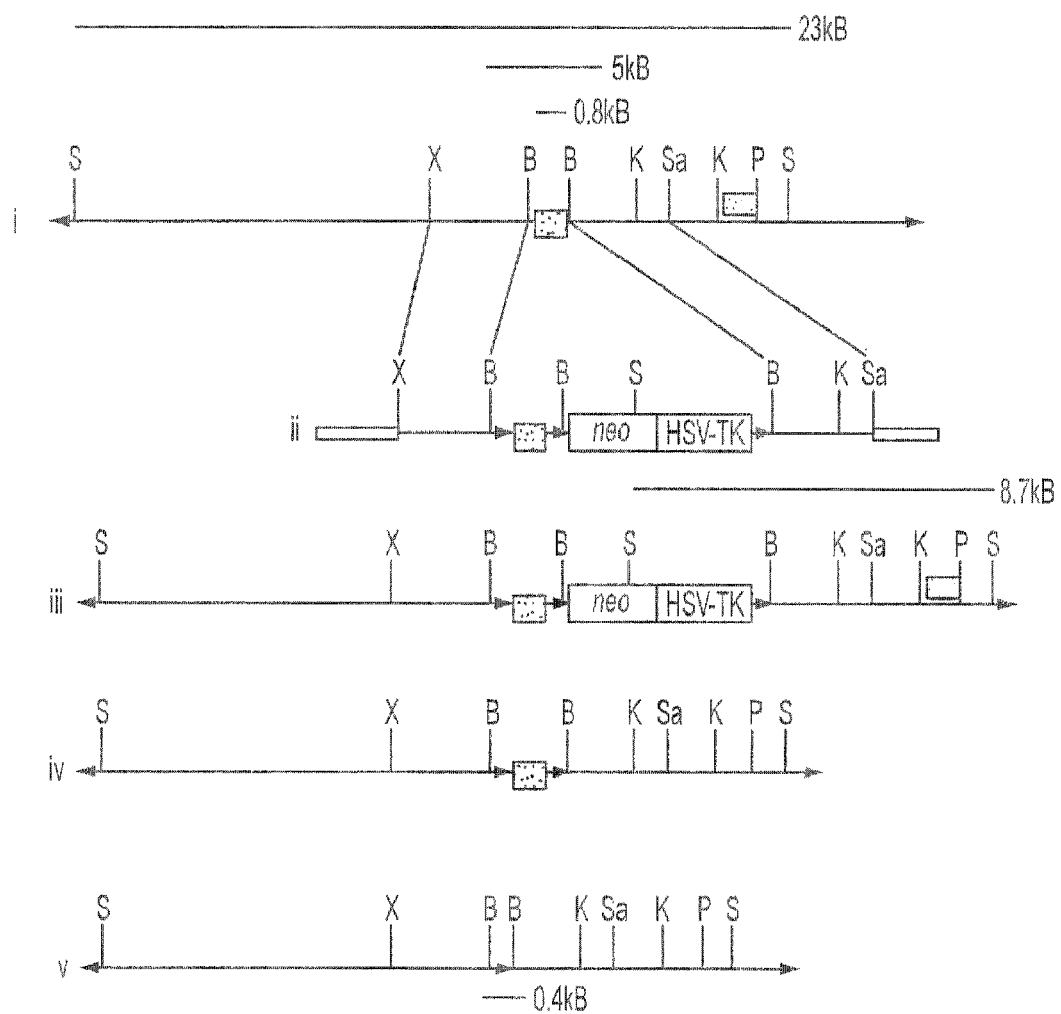
FIG. 1(A-D) illustrates the production of mice with a SHIP deficiency.

The instant invention teaches inhibition of SHIP function for the suppression of NK cell-mediated activities. Such activities include rejection of histo-incompatible marrow and stem cell grafts (e.g. pluripotent, muscle, neural, liver, and other stem cell types) and rejection of organ transplants.

Thus methods are provided for increasing the efficiency of engraftment of an allogeneic bone marrow transplant or solid organ allograft or xenograft, in the treatment of a patient having a disease, such as cancer, autoimmune disease, HIV/AIDS, or a genetic deficiency requiring such a transplant, in which an efficacious amount of a substance that inhibits SHIP function is administered to the patient, optionally in a pharmaceutically acceptable carrier. The invention also provides a method for reducing graft-versus-host-disease following histo-incompatible marrow grafts.

In another embodiment, the invention provides a method for decreasing rejection of a MHC (major histocompatability complex) histo-incompatible marrow graft in a patient, where there is a MHC disparity between donor and patient of 1, 2, 3 or more allele mismatches, or the transplanted marrow is a xenograft (e.g. bone marrow from baboon, chimp, or the like) by administering a substance that inhibits SHIP function and thereby suppresses rejection by impairing NK cell function.

Another embodiment of the invention provides methods for decreasing rejection of a bone marrow allograft, or rejection of a solid organ allograft or xenograft in a patient by administering a substance that inhibits SHIP function.

A further embodiment provides a method for treatment or prevention of graft-versus-host disease in a patient that has, or will, undergo a bone marrow allograft.

A further embodiment provides for a method of inhibiting APC function before and during allogeneic transplants of solid organs, skin and bone marrow, thereby increasing the therapeutic efficacy of such transplants.

A preferred method of the invention further comprises administering to said patient an allogeneic bone marrow transplant.

According to preferred embodiments, the substance suitable for the instant invention can be a nucleic acid, such as a genetic construct or other genetic means directing expression of an antagonist of SHIP function. Nucleic acid molecules suitable for the inventive method include anti-sense polynucleotides, other polynucleotides that bind to SHIP mRNA, recombinant retroviral vector, or a combination thereof. A preferred genetic construct of the invention comprises a gene delivery vehicle, a recombinant retroviral vector, or a combination thereof. In a preferred embodiment, the substance that inhibits SHIP function is a nucleic acid that hybridizes to a SHIP mRNA.

Preferred substances may also include peptidomimetic inhibitors of SHIP function, ribozymes, and an RNA aptamer, or a combination thereof.

Suitable substances for the instant invention may also be a low molecular weight substance having a molecular weight of less than about 10,000 that inhibits SHIP activity.

In yet a further embodiment the invention provides methods for screening substances to identify substances that inhibit SHIP function. A preferred screening method of the invention is through the use of an NK cell line comprising an indicator of SHIP function that is exposed to candidate substances. According to a preferred embodiment, the inventive method for screening a substance suspected of inhibiting SHIP function, comprising: providing an NK cell line that comprises an indicator of SHIP function; contacting said cell line with said substance; and measuring the response of said indicator to said substance, whereby the effectiveness of said substance as an inhibitor of SHIP function is assessed from the response of said indicator.

Preferred indicators include fluorogenic substrates for SHIP, indicators that indicate surface levels of Ly49 receptors, killer inhibitor receptors (KIR), and CD94NKG2 complexes, Fas, Fas ligand, or phosphatidyl serine in the extracellular leaflet of the plasma membrane.

In one embodiment, the response of said indicator is measured by flow cytometry or by a multi-well fluorescence detector.

According to preferred embodiments, substances that are suitable for screening include a nucleic acid, such as a genetic construct or other genetic means directing expression of an antagonist of SHIP function. Nucleic acid molecules suitable for the inventive method include anti-sense polynucleotides, other polynucleotides that bind to SHIP mRNA, recombinant retroviral vector, or a combination thereof. A preferred genetic construct of the invention comprises a gene delivery vehicle, a recombinant retroviral vector, or a combination thereof. In a preferred embodiment, the substance that inhibits SHIP function is a nucleic acid that hybridizes to a SHIP mRNA. Preferred substances may also include peptidomimetic inhibitors of SHIP function, ribozymes, and an RNA aptamer, or a combination thereof. A suitable substance for the instant invention may also be a low molecular weight substance having a molecular weight of less than about 10,000 that inhibits SHIP activity.

The instant invention further provides a mouse cell comprising a $SHIP^{flox}$ allele of a SHIP gene having a first exon and a promoter, wherein the first exon and the promoter have been deleted in the $SHIP^{flox}$ allele. More preferably, the mouse cell of the invention is homozygous with regard to the $SHIP^{flox}$ allele. Still more preferably, the mouse cell of the invention is an embryonic stem cell.

The instant invention further provides a transgenic mouse comprising a cell of the invention wherein the cell comprises a $SHIP^{flox}$ allele. In a preferred embodiment, the transgenic mouse of the instant invention is derived from the inventive embryonic stem cell. In a particularly preferred embodiment, the transgenic mouse of the invention has a genotype of $SHIP^{-/-}$. More preferably, the transgenic mouse of the invention does not express SHIP protein.

The instant invention further provides a transgenic mouse having the genotype $SHIP^{-/-}$ wherein the transgenic mouse has decreased numbers of dendritic cells.

The instant invention further provides a transgenic mouse having the genotype $SHIP^{-/-}$ wherein the transgenic mouse is a very poor stimulator of allogeneic T cell response in the mixed leukocyte reaction.

Further provided are therapeutic compositions comprising a substance that inhibits SHIP function, optionally in a pharmaceutically acceptable carrier.

DETAILED DESCRIPTION OF THE INVENTION

The present invention relates to the novel and unexpected finding that SHIP activity has a critical role in regulating Natural Killer (NK) cell function. The present invention comprises methods for the suppression of allograft and xenograft rejection, prevention of graft-versus-host disease (GVHD) in a patient that has, or will, undergo a bone marrow allograft, and methods for screening substances and genetic therapeutic agents to identify those capable of altering NK cell function.

In view of the following disclosure and Examples, it will be apparent to those of skill in the art that inhibition of SHIP activity is advantageous in the suppression of immune rejection reactions, and in the treatment of GVHD, since the functionality of NK cells is shown herein for the first time to be impaired in an advantageous manner, with respect to immune rejection and GVHD, in the absence of SHIP activity.

Thus in a preferred embodiment, the instant invention provides a method for increasing the efficiency of engraftment of an allogeneic bone marrow transplant, for example in the treatment of cancer, autoimmune disease, HIV/AIDS, or any other genetic impairment that is treated by a marrow transplant. It is known that NK cells have a key role in the rejection of such grafts, and that prolongation of the period before rejection, or elimination of the rejection reaction entirely, are both significantly beneficial for treatment. Thus, in preferred embodiments, a substance that inhibits SHIP function is administered, such as by a genetic construct or as a pharmaceutical, which may be a nucleic acid or other substance that is, or leads to expression of, an antagonist of SHIP function. The genetic construct of the invention is preferably operably linked to a promoter and other signals directing expression of a protein SHIP antagonist, or the antagonist can be an anti-sense nucleic acid, or a small molecule enzymatic inhibitor, or a peptidomimetic inhibitor, or a ribozyme.

In still further embodiments, as shown herein, rejection of solid organ allografts or xenografts is decreased by administration of a means for reducing SHIP activity.

The invention further includes embodiments in which the rejection of MHC disparate marrow grafts (i.e. those in which the MHC identity of donor tissue cells may differ from the recipient by 1, 2, 3 or more alleles), is suppressed, thus greatly increasing the probability that suitable donors for a given recipient may be found within a certain population. It should be noted that up to six allele mismatches can be obtained from combinations of alleles selected from the following allele pairs: HLA-A, HLA-B and HLA-C.

In further embodiments, the efficiency of bone marrow transplantation is improved by suppression of graft-versus-host disease in a patient through inhibition of SHIP activity.

In the foregoing methods for enhancing the success of allografts or xenografts, the SHIP antagonist is preferably administered prior to the graft. Administration of, for example, substances that lead to a reduction of SHIP activity can be performed sufficiently long before grafting (for example, for a period of about 1-4 weeks) that an advantageous alteration in the amounts of sub-populations of NK cells is obtained (see, Examples). In this manner, the beneficial effects of SHIP inhibition can be obtained prior to grafting, thereby reducing both the probability of graft rejection and the probability of GVHD, while simultaneously increasing the degree of MHC allelic mismatch that is tolerated.

However, it is not essential to the present invention that means for inhibiting SHIP be administered prior to grafting; beneficial reduction in both the probability of graft rejection and the probability of GVHD, and an increase the degree of MHC allelic mismatch that is tolerated, can still be obtained by administration of a means for inhibiting SHIP activity at, or subsequent to, the time of engraftment.

In yet a further embodiment the invention provides methods for screening substances to identify those substances that inhibit SHIP function. Suitable screening assays for the instant invention may be cellular based. A skilled person will recognize that any cell line that has SHIP activity that could be monitored is suitable for using for the screening assays.

Suitable screening assays may also be performed without the use of a cell culture. For example, a simple chemical reaction is also suitable that assays the impact of a substance being evaluated on the enzyme activity of SHIP. Preferably, an in vitro screening method without resorting to a cell culture may use, for example, purified natural or recombinant SHIP enzyme and a suitable substrate that generates a detectable signal when it is cleaved or otherwise acted upon by SHIP. An example of such a detectable signal is a change in the substrate's fluorescence spectra or intensity. Substances that effect a detectable signal in the presence of SHIP and a substrate are thereby identified, and may be tested for their pharmaceutical effectiveness according to methods well known to those skilled in the art.

In a preferred screening embodiment, methods are provided for screening of substances and genetic constructs that are useful for inhibiting SHIP function. Thus it is envisioned as within the scope of the present invention to use NK cell lines in an assay system that would aid in the screening and identification of pharmaceutical agents or genetic therapies that reduce or eliminate SHIP activity and function.

Such agents or genetic therapies encompass, but are not limited to the following: 1) small molecule inhibitors (preferably having a molecular weight of less than 10,000) of SHIP enzymatic activity (i.e. suicide substrates; competitive or non-competitive inhibitors of SHIP activity; RNA aptamers; or PIP 3, 4, or 5 analogs), 2) anti-sense oligonucleotides, 3) peptidomimetics, 4) ribozymes, 5) means for interfering with transcription and/or translation of SHIP RNA, or 6) genetic therapy comprising transfection with a dominant negative SHIP mutant. These agents and/or genetic therapies can exert their effects by preventing the recruitment of SHIP to complexes with other signal transduction components or to the plasma membrane where SHIP can access its inositol phospholipid substrates. Therefore, such substances are effective by blocking SHIP function in NK cells without necessarily altering enzymatic activity. Because SHIP is an intracellular enzyme, one embodiment of such an assay utilizes a fluorogenic substrate of SHIP that reports SHIP activity. Such fluorogenic SHIP substrates are introduced into NK cell lines, which are either treated with potential inhibitors or left untreated. Such fluorogenic SHIP substrates are, for example, substances that exhibit fluorescence upon cleavage. Methods for preparing such substrates based upon the release from fluorescence quenching that occurs when there is cleavage of a substrate resulting in either (a) the separation of a fluorophore from a fluorescence quenching acceptor, or (b) separation of self-quenching fluorophores, or (e) enhanced fluorescence of a single fluorophore due to changes in its immediate chemical environment subsequent to cleavage, are well known in the art. The relative activity of SHIP is assessed by the fluorescent signal emanating from the cells. NK cells derived from the SHIP$^{-/-}$ mice serve as negative controls for this assay. Further, based on the disclosure herein that loss of SHIP activity results in changes in the surface levels of Ly49 receptors, Fas and Fas ligand (FasL), as well as phosphatidyl serine flipping to the extracellular leaflet of the plasma membrane in NK cells, assays for these markers can serve as additional markers of SHIP inhibition. Therefore, cell-based assays in NK cells lines permit inhibition of SHIP activity and function to be assessed either directly or indirectly. These assays are monitored by flow cytometry or by multi-well fluorescence detectors to permit whole cell detection of SHIP activity and its reduction by such agents as described above.

Within the present disclosure, the following terms are to be understood as follows.

An "isolated polypeptide" or "isolated polynucleotide" as used herein refers to a polypeptide or polynucleotide, respectively, produced in vivo or in vitro in an environment manipulated by humans using state of the art techniques of molecular biology, biochemistry and gene therapy. For example, an isolated polypeptide can be produced in a cell free system by automated peptide or polypeptide synthesis, in heterologous host cells transformed with the nucleic acid sequence encoding the polypeptide and regulatory sequences for expression in the host cells, and in an animal into which the coding sequence of the polypeptide has been introduced for expression in the animal. A polypeptide or polynucleotide is "isolated" for purposes herein to the extent that it is not present in its natural state inside a cell as a product of nature. For example, such isolated polypeptides or polynucleotides can be 10% pure, 20% pure, or a higher degree of purity.

The term "inositol polyphosphate 5-phosphatase" as used herein refers to a family of phosphatases each of which removes the 5 phosphate from inositol- and phosphatidyli-nositol-polyphosphates. The family of proteins is determined by the substrate specificity of these enzymes and by amino acid sequence homology. A description of some of the aspects of the family is provided in Jefferson and Majerus, J Biol Chem 270: 9370-77 (1995). The term "activated T cell" and "activated B cell" refers to T and B cells that have been stimulated, for example, with cytokines or growth factors, or which have had their antigen receptors cross-linked using antibodies, all of which events stimulate gene expression, cell proliferation or other responses in T and B cells.

The term "tyrosine phosphorylated" as used herein refers to the addition of a phosphate group at a tyrosine residue. Generally, tyrosine phosphorylation of polypeptides is associated with activation or inactivation of signaling pathways. Tyrosine phosphorylation is also associated with activation or inhibition of signaling molecules. Tyrosine phosphorylation of a polypeptide of the invention can occur in response to, for example, B or T cell activation. In some cases, binding to other polypeptides occurs before, after, or during the tyrosine phosphorylation of a polypeptide.

The term "apparent molecular weight" as used herein refers to the molecular weight of the protein or polypeptide as it migrates on a polyacrylamide gel under reducing or non-reducing conditions. The "apparent" molecular weight may be accounted for by glycosylations or other moieties that alter the molecular weight of the polypeptide alone.

The term "SHIP" as used herein refers to SH2-containing inositol-5-phosphatase. SHIP may have an apparent molecular weight of about 145 kDa and is expressed in at least hemopoietic cells. It contains an amino-terminal src-homology domain (SH2), a central 5'-phosphoinositol phosphatase domain, two phosphotyrosine binding consensus sequences, and a proline-rich region at the carboxyl tail.

The term a "means for inhibiting SHIP function" comprises genetic and non-genetic means for inhibiting SHIP function, and includes substances that inhibit SHIP functions.

Among the genetic construct inhibiting SHIP function are various "gene delivery vehicles" known to those of skill in the art, that facilitate delivery to a cell of for example, a coding sequence for expression of a polypeptide, such as a SHIP inhibitor, an anti-sense oligonucleotide, an RNA aptamer capable of inhibiting SHIP enzymatic activity, an RNA aptamer capable of inhibiting a ribozyme, or another genetic construct of inhibiting SHIP activity known to those of skill in the art.

Among the non-genetic means inhibiting SHIP function are pharmaceutical agent, pharmaceutically acceptable salts thereof that are preferably administered in a pharmaceutically acceptable carrier.

According to preferred embodiments, substances suitable for the instant invention can be a nucleic acid, such as a genetic construct or other genetic means directing expression of an antagonist of SHIP function. Nucleic acid molecules suitable for the inventive method include anti-sense polynucleotides, other polynucleotides that bind to SHIP mRNA, recombinant retroviral vector, or a combination thereof. A preferred genetic construct of the invention comprises a gene delivery vehicle, a recombinant retroviral vector, or a combination thereof. In a preferred embodiment, the substance that inhibits SHIP function is a nucleic acid that hybridizes to a SHIP mRNA.

Preferred substances may also include peptidomimetic inhibitors of SHIP function, ribozymes, and an RNA aptamer, or a combination thereof.

Suitable substances for the instant invention may also be a low molecular weight substance having a molecular weight of less than about 10,000 that inhibits SHIP activity.

The cell to which said component or substance is delivered can be within a mammal, as in in vivo gene therapy, or can be removed from a mammal for transfection, or administration of a pharmaceutical agent, and can be subsequently returned to the mammal, as, for example, in ex vivo therapy or ex vivo gene therapy. The delivery vehicle can be any component or vehicle capable of accomplishing the delivery of a gene or substance to a cell, for example, a liposome, a particle, naked DNA, or a vector. A gene delivery vehicle is a recombinant vehicle, such as a recombinant viral vector, a nucleic acid vector (such as plasmid), a naked nucleic acid molecule such as a gene, a nucleic acid molecule complexed to a polycationic molecule capable of neutralizing the negative charge on the nucleic acid molecule and condensing the nucleic acid molecule into a compact molecule, a nucleic acid associated with a liposome (Wang, et al., PNAS 84:7851, 1987), and certain eukaryotic cells such as a producer cell, that are capable of delivering a nucleic acid molecule having one or more desirable properties to host cells in an organism. The desirable properties include the ability to express a desired substance, such as a protein, enzyme, or antibody, and/or the ability to provide a biological activity, which is where the nucleic acid molecule carried by the gene delivery vehicle is itself the active agent without requiring the expression of a desired substance. One example of such biological activity is gene therapy where the delivered nucleic acid molecule incorporates into a specified gene so as to inactivate the gene and "turn off" the product the gene was making, or to alter the translation or stability of the mRNA of the specified gene product. Gene delivery vehicle refers to an assembly which is capable of directing the expression of the sequence(s) or gene(s) of interest or of turning off the gene of interest. The gene delivery vehicle will generally include promoter elements and may include a signal that directs polyadenylation. In addition, the gene delivery vehicle can include a sequence which is operably linked to the sequence(s) or gene(s) of interest and, when transcribed, acts as a translation initiation sequence. The gene delivery vehicle may also include a selectable marker such as Neo, $SV^2$ Neo, TK, hygromycin, phleomycin, histidinol, or DHFR, as well as one or more restriction sites and a translation termination sequence. Gene delivery vehicles as used within the present invention refers to recombinant vehicles, such as viral vectors (Jolly, Cancer Gen. Therapy 1:5164, 1994), nucleic acid vectors, naked DNA, oligonucleotides, cosmids, bacteria, and certain eukaryotic cells (including producer cells; see U.S. Ser. No. 08/240,030 and U.S. Ser. No. 07/800,921), that are capable of eliciting an immune response within an animal. Representative examples of such gene delivery vehicles include poliovirus (Evans et al., Nature 339:385-388, 1989; and Sabin, J. Biol. Standardization 1:115-118, 1973); rhinovirus; pox viruses, such as canary pox virus or vaccinia virus (Fisher-Hoch et al., PNAS 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; WO 89/01973); SV40 (Mulligan et al., Nature 277:108-114, 1979); retrovirus (U.S. Pat. No. 4,777,127, GB 2,200,651, EP 0,345,242, and WO 91/02805); influenza virus (Luytjes et al., Cell 59:1107-1113, 1989; McMicheal et al., N. Eng. J. Med. 309:13-17, 1983; and Yap et al., Nature 273:238-239, 1978); adenovirus (Berkner, Biotechniques 6:616-627, 1988; Rosenfeld et al., Science 252:431-434, 1991; WO 93/9191; Kolls et al., PNAS 91:215-219, 1994; Kass-Eisler et al., PNAS 90:11498-11502, 1993; Guzman et al., Circulation 88:2838-2848, 1993; Guzman et al., Cir. Res. 73:1202-1207, 1993; Zabner et al., Cell 75:207-216, 1993; Li et al., Hum. Gene. Ther. 4:403-409, 1993; Caillaud et al., Eur. J. Neurosci. 5:1287-1291, 1993; Vincent et al., Nat. Genet. 5:130-134, 1993; Jaffe et al., Nat. Genet. 1:372-378, 1992; and Levrero et al., Gene 101:195-202, 1991); parvovirus such as adeno-associated virus (Samulski et al., J. Vir. 63:3822-3828, 1989; Mendelson et al., Virol. 166:154-165, 1988; PA 7/222,684); herpes (Kit, Adv. Exp. Med. Biol. 215:219-236, 1989); SV40; HIV (Poznansky, Virol. 65:532-536, 1991); measles (EP 0 440,219); astrovirus (Munroe, S. S. et al., J. Vir. 67:3611-3614, 1993); Semlild Forest Virus, and coronavirus, as well as other viral systems (e.g., EP 0,440,219; WO 92/06693; U.S. Pat. No. 5,166,057). In addition, viral carriers may be homologous, non-pathogenic(defective), replication competent viruses (e.g., Overbaugh et al., Science 239:906-910, 1988) that nevertheless induce cellular immune responses, including cytotoxic T-cell lymphocytes (CTL).

The term "ex vivo administration" refers to transfecting or administering a substance to a cell, for example a cell from a population of cells that are exhibiting aberrant SHIP activity, after the cell is removed from the mammal. After transfection or administration of the substance, the cell is then replaced in the mammal. Ex vivo administration can be accomplished by removing cells from a mammal, optionally selecting cells to transform, rendering the selected cells incapable of replication, transforming or treating the selected cells with a polynucleotide or other means for modulating SHIP activity, and placing the transformed or treated cells back into the mammal.

"Administration" or "administering" as used herein refers to the process of delivering to a mammal a therapeutic agent, or a combination of therapeutic agents. The process of administration can be varied, depending on the therapeutic agent, or agents, and the desired effect. Administration can be accomplished by any means appropriate for the therapeutic agent, for example, by parenteral, mucosal, pulmonary, topical, catheter-based, or oral means of delivery. Parenteral delivery can include, for example, subcutaneous, intravenous, intramuscular, intra-arterial, and injection into the tissue of an organ. Mucosal delivery can include, for example, intranasal delivery. Pulmonary delivery can include inhalation of the agent. Catheter-based delivery can include delivery by iontophoretic catheter-based delivery. Oral delivery can include delivery of an enteric coated pill, or administration of a liquid by mouth. Administration will generally also include delivery with a pharmaceutically acceptable carrier, such as, for example, a buffer, a polypeptide, a peptide, a polysaccharide conjugate, a liposome and/or a lipid. Gene therapy protocol is considered an administration in which the therapeutic agent is a polynucleotide capable of accomplishing a therapeutic goal when expressed as a transcript or a polypeptide in the mammal.

A "nucleic acid" or a "polynucleotide," as used herein, refers to either RNA or DNA molecule that encodes a specific amino acid sequence or its complementary strand. Nucleic acid molecules may also be non-coding sequences, for example, a ribozyme, an antisense oligonucleotide, or an untranslated portion of a gene. A "coding sequence" as used herein, refers to either RNA or DNA that encodes a specific amino acid sequence, or its complementary strand. A polynucleotide may include, for example, an antisense oligonucleotide, or a ribozyme, and can also include such items as a 3' or 5' untranslated region of a gene, or an intron of a gene, or other region of a gene that does not make up the coding region of the gene. The DNA or RNA may be single stranded or double stranded. Synthetic nucleic acids or synthetic polynucleotides can be chemically synthesized nucleic acid sequences, and can also be modified with chemical moieties to render the molecule resistant to degradation. Synthetic nucleic acids can be ribozymes or antisense molecules, for example. Modifications to synthetic nucleic acid molecules include nucleic acid monomers or derivative or modifications thereof, including chemical moieties, such as, for example, phosphothioate modification. A polynucleotide derivative can include, for example, such polynucleotides as branched DNA (bDNA). A polynucleotide can be a synthetic or recombinant polynucleotide, and can be generated, for example, by polymerase chain reaction (PCR) amplification, or recombinant expression of complementary DNA or RNA, or by chemical synthesis.

The term "an expression control sequence" or a "regulatory sequence" refers to a sequence that is conventionally used to effect expression of a gene that encodes a polypeptide and include one or more components that affect expression, including transcription and translation signals. Such a sequence includes, for example, one or more of the following: a promoter sequence, an enhancer sequence, an upstream activation sequence, a downstream termination sequence, a polyadenylation sequence, an optimal 5' leader sequence to optimize initiation of translation in mammalian cells, a Kozak sequence, which identifies optimal residues around initiator AUG for mammalian cells. The expression control sequence that is appropriate for expression of the present polypeptide differs depending upon the host system in which the polypeptide is to be expressed. For example, in prokaryotes, such a control sequence can include one or more of a promoter sequence, a Shine-Dalgarno sequence, a ribosomal binding site, and a transcription termination sequence. In eukaryotes, for example, such a sequence can include a promoter sequence, and a transcription termination sequence. If any necessary component of an expression control sequence is lacking in the nucleic acid molecule of the present invention, such a component can be supplied by the expression vector to effect expression. Expression control sequences suitable for use herein may be derived from a prokaryotic source, an eukaryotic source, a virus or viral vector or from a linear or circular plasmid. Further details regarding expression control sequences are provided below. An example of a regulatory sequence is the human immunodeficiency virus ("HIV-1") promoter that is located in the U3 and R region of the HIV-1 long terminal repeat ("LTR"). Alternatively, the regulatory sequence herein can be a synthetic sequence, for example, one made by combining the UAS of one gene with the remainder of a requisite promoter from another gene, such as the GADP/ADH2 hybrid promoter.

"Hybridization" refers to the association of two nucleic acid sequences to one another by specific hydrogen bonding. Typically, one sequence can be fixed to a solid support and the other is free in solution. The two sequences are placed in contact with one another under conditions that favor hydrogen bonding. Factors that affect this binding bonding include: the type and volume of solvent; reaction temperature; time of hybridization; agitation; agents to block the non-specific attachment of the liquid phase sequence to the solid support (Denhardt's reagent or BLOTTO); concentration of the sequences; use of substances to increase the rate of association of sequences (dextran sulfate or polyethylene glycol); and the stringency of the washing conditions following hybridization. See Sambrook et al. MOLECULAR CLONING; A LABORATORY MANUAL, SECOND EDITION (1989), Volume 2, chapter 9, pages 9.47 to 9.57. "Stringency" refers to conditions in a hybridization reaction that favor association of very similar sequences over sequences that differ. For example, the combination of temperature and salt concentration should be chosen that is approximately 12° to 20° C. below the calculated Tm of the hybrid under study.

The term "naked DNA" refers to polynucleotide DNA for administration to a mammal for expression in the mammal or to inhibit SHIP activity. The polynucleotide can be, for example, a coding sequence, and the polynucleotide DNA can be directly or indirectly connected to an expression control sequence that can facilitate the expression of the coding sequence once the DNA is inside a cell. Alternatively, the DNA can direct production of RNA or a polypeptide that inhibits SHIP activity.

"Recombinant retroviral vector" refers to an assembly which is capable of directing the expression of a sequence(s) or gene(s) of interest. Preferably, the retroviral vector construct should include a 5' LTR, a tRNA binding site, a packaging signal, one or more heterologous sequences, an origin of second strand DNA synthesis and a 3' LTR. A wide variety of heterologous sequences may be included within the vector construct, including for example, sequences which encode a protein (e.g., cytotoxic protein, disease-associated antigen, immune accessory molecule, or replacement protein), or which are useful in and of themselves (e.g., as ribozymes or antisense sequences). Alternatively, the heterologous sequence may merely be a "stutter" or "filler" sequence of a size sufficient to allow production of retroviral particles containing the RNA genome. Preferably, the heterologous sequence is at least 1, 2, 3, 4, 5, 6, 7 or 8 Kb in length. The retroviral vector construct may also include transcriptional promoter/enhancer or locus defining element(s), or other elements which control gene expression by means such as alternate splicing, nuclear RNA export, post-translational modification of messenger, or post-transcriptional modification of protein. Optionally, the retroviral vector construct may also include selectable markers that confer resistance of recombinant retroviral vector, transduced or transfected, cells to TK, hygromycin, phleomycin, histidinol, or DHFR, as well as one or more specific restriction sites and a translation termination sequence.

A "therapeutically effective amount" is that amount that will generate the desired therapeutic outcome. For example, if the therapeutic effect desired is reduction or suppression of rejection of a transplant, the therapeutically effective amount is that amount that facilitates reduction or suppression of rejection of a transplant. A therapeutically effective amount can be an amount administered in a dosage protocol that includes days or weeks of administration.

The term "pharmaceutically acceptable carrier" refers to a carrier for administration of a therapeutic agent, such as, for example, a polypeptide, polynucleotide, small molecule (preferably a molecule having a molecular weight of less than about 10,000), peptoid, or peptide, refers to any pharmaceutically acceptable carrier that does not itself induce the production of antibodies harmful to the individual receiving the composition, and which may be administered without undue toxicity.

"Vector construct" refers to an assembly which is capable of directing the expression of the sequence(s) or gene(s) of interest. The vector construct can include transcriptional promoter/enhancer or locus defining element(s), or other elements which control gene expression by other means such as alternate splicing, nuclear RNA export, post-translational modification of messenger, or post-transcriptional modification of protein. In addition, the vector construct must include a sequence which, when transcribed, is operably linked to the sequence(s) or gene(s) of interest and acts as a translation initiation sequence. Optionally, the vector construct may also include a signal which directs polyadenylation, a selectable marker such as Neo, TK, hygromycin, phleomycin, histidinol, or DHFR, as well as one or more restriction sites and a translation termination sequence. In addition, if the vector construct is placed into a retrovirus, the vector construct must include a packaging signal, long terminal repeats (LTRs), and positive and negative strand primer binding sites appropriate to the retrovirus used (if these are not already present).

"Tissue-specific promoter" refers to transcriptional promoter/enhancer or locus defining elements, or other elements which control gene expression as discussed above, which are preferentially active in a limited number of tissue types. Representative examples of such tissue-specific promoters include the PEP-CK promoter, HER2/neu promoter, casein promoter, IgG promoter, Chorionic Embryonic Antigen promoter, elastase promoter, porphobilinogen deaminase promoter, insulin promoter, growth hormone factor promoter, tyrosine hydroxylase promoter, albumin promoter, alphafetoprotein promoter, acetyl-choline receptor promoter, alcohol dehydrogenase promoter, a or P globin promoters, T-cell receptor promoter, or the osteocalcin promoter.

"Mammalian cell" as used herein refers to a subset of eukaryotic cells useful in the invention as host cells, and includes human cells, and animal cells such as those from dogs, cats, cattle, horses, rabbits, mice, goats, pigs, etc. The cells used can be genetically unaltered or can be genetically altered, for example, by transformation with appropriate expression vectors, marker genes, and the like. Mammalian cells suitable for the method of the invention are any mammalian cell capable of expressing the genes of interest, or any mammalian cells that can express a cDNA library, cRNA library, genomic DNA library or any protein or polypeptide useful in the method of the invention. Mammalian cells also include cells from cell lines such as those immortalized cell lines available from the American Type Culture Collection (ATCC). Such cell lines include, for example, rat pheochromocytoma cells (PC12 cells), embryonal carcinoma cells (P19 cells), Chinese hamster ovary (CHO) cells, HeLa cells, baby hamster kidney (BHK) cells, monkey kidney cells (COS), human hepatocellular carcinoma cells (e.g., Hep G2), human embryonic kidney cells, mouse sertoli cells, canine kidney cells, buffalo rat liver cells, human lung cells, human liver cells, mouse mammary tumor cells, as well as others. Also included are hematopoetic stem cells, neuronal stem cells such as neuronal sphere cells, and pluripotent or embryonic stem cells (ES cells).

The term "antagonist" as used herein refers to a molecule that blocks signaling, such as for example a molecule that can bind a receptor, but which does not cause a signal to be transduced by the receptor to the cell. In the case of inositol polyphosphatase 5'-phosphatases an antagonist might block signaling by binding, for example, at an SH2 domain on the molecule, or by binding, for example, so as to inhibit its phosphatase activity. In general, an antagonist of a polypeptide is an inhibitor of any biological activity of the polypeptide. A given inhibitor or agonist may target and inhibit one biological activity, while not affecting another non-target activity of the molecule.

The instant invention will be better understood by reference to the following non-limiting examples.

EXAMPLE 1

Methods $^{51}$Cr Release Assay

Cell mediated cytolytic activity can be detected with a $^{51}$Cr release assay. The percentage of specific lysis of $^{51}$Cr-labeled target cells in 200 µl is determined for each lymphocyte population by plotting specific cytotoxicity versus the log 10 of the viable effector number. Spontaneous $^{51}$Cr release values vary between 5% and 15% of the total incorporated label.

Specifically, FACS purified 2B4$^+$NK1.1$^+$ NK cells from SHIP$^{-/-}$ or SHIP$^{+/+}$ littermates are co-incubated with $5 \times 10^3$ $^{51}$Cr-labelled Yac-1 target cells at the indicated effector:target (E:T) ratio in 96-well round-bottomed plates and incubated at 37° C. for 5hr. Following incubation half the supernatant in each well is removed to determine radioactivity. The percentage of specific $^{51}$Cr release is calculated from the formula $100 \times (A-B)/(C-B)$ where A is $^{51}$Cr release in the presence of effector cells and B is the spontaneous release in the absence of effector cells. C is the total $^{51}$Cr released from target cells lysed by addition of detergent.

FACS Assays

Following specific fluorescent labeling as indicated, cells are sorted, for example, using a modified Becton Dickenson fluorescence activated cell sorter (FACS II) based on the wavelength of the fluorescent label stain, typically a fluorescein (488 nm) or phycobillidye dye (360 nm, e.g. CPE or APC or equivalent).

FACS Analysis of the NK Compartment

To analyze the peripheral NK cell compartment spleens are collected from mice at various ages, a single cell suspension prepared by NH$_4$CL lysis of erythrosis and stained with the antibodies against the NK associated markers 2B4 (PE), NK1.1 (FITC) and CD3(APC) (FIG. 1). For analysis of the NK cell repertoire (FIG. 4), cells are stained with 2B4, Nk1.1 and anti-Ly49A (A1), -Ly49C/I (5E6), -Ly49D (4E5), -Ly49G2 (4D11) or CD94 (Ebioscience, San Diego, Calif.). To distinguish Ly49C staining from Ly49I, cells are stained with Nk1.1, Ly49C/I and Ly49I (YLI90). All biotin conjugates are revealed by StrepAvidin-APC. With the exception of the anti-CD94 antibodies and StrepAvidin-APC all FACS reagents are obtained from BD-Pharmingen (San Diego, Calif.). For analysis of BudR labeling, age matched, 5 week old SHIP$^{-/-}$ and SHIP$^{+/+}$ mice are placed on drinking water containing 0.8 mg/ml BrdU for one week and then splenic NK cells are analyzed immediately following the labeling period ("Pulse") or after a two week period on normal drinking water following the one week labeling ("Pulse and Chase"). Uptake and retention of BrdU by splenic NK1.1$^+$CD3$^-$ cells is assessed using the BrdU flow kit (Pharmingen) per the manufacturer's instructions. Statistical significance of FACS assays is assessed by the Mann-Whitney U test.

Biochemical Analysis of SHIP and Akt

NK-enriched C57BL6/J splenocytes are prepared by depletion of B cells and macrophages by adherence to nylon wool followed by T cell depletion using anti-CD3 plus complement. NK cells are then lysed in modified RIPA buffer. Prior to immunoprecipitation, the NK cell lysates are precleared twice by incubation with 0.25 µg of a murine or rat IgG2a antibody (BD Pharmingen) and 50 µl of Protein A-Agarose or Protein G-Sepharose beads (Upstate Biotechnology). The beads are pelleted at 15,000×g for 15 minutes at four degrees C. The precleared supernatants are immunoprecipitated with 2 µg of anti-Ly49A (A1), -Ly49C/I (5E6), -Ly49D (HBF-719), -Ly49G2 (4D11), -Ly49G2 (YLI-90) or IgG2a (BDPharmingen). Murine IgG2a is used to pre-clear and as a control for Ly49A, Ly49C/I immune precipitates. Rat IfF2a is used to pre-clear and as a negative control for immune precipitates. Immune complexes are brought down by addition of 50 μl of Protein A-Agarose (Ly49A, Ly49C/I) or Protein G-Sephadex (Ly49F, Ly49G2, Ly49I) beads. The immunoprecipitates are resolved on a 4-12% Tris-Bis polyacrylamide gel and transferred to a nitrocellulose membrane (Amersham Pharmacia). The filters are then probed with a 1:1000 dilution of anti-SHIP(P2C6) and an anti-mouse IgG secondary antibody (Amersham Pharmacia) at a 1:80,000 dilution. The presence of SHIP is revealed using the SuperSignal West Femto reagent (Pierce). The results of the Ly49 immunoprecipitations in FIG. 5 are representative of three independent analyses of NK-enriched splenocytes. For analysis of Akt activation lysates of purified NK cells form the spleens of SHIP$^{-/-}$ and SHIP$^{+/+}$ are prepared as above. Equal quantities of protein from cell lysates prepared from SHIP$^{-/-}$ and SHIP NK cells are resolved on a 4-12% Tris-Bis polacrylamide gel (Invitrogen), transferred to a nitrocellulose membrane (Amersham) and the filters probed with an anti-PhosphoAkt(Thr308) antibody (Cell Signalling) at a 1:1000 dilution. The presence of Akt is detected by a donkey and anti-rabbit IgG secondary antibody coupled to HRP (Amersham) at a 1:2000 dilution and revealed using ECL substrate (Amersham). The blot is then stripped and reprobed in a similar manner suing anti-β-actin (Cell Signaling), anti-GAPDH (Research Diagnostics) and antiαtubulin (Oncogene Research) as internal controls for protein loading. The detection of increased Akt levels and its activation is representative of three separate analysis of NK cell lysates from SHIP$^{-/-}$ and SHIP$^{+/+}$ mice.

Analysis of BM Graft Rejection and GVHD

Whole bone marrow (WBM) cells are obtained from tibias and femurs of A/SW(H-2s)/Sn, BALB/C or β2m−/− mice and washed once in PBS. WBM cells (5×10$^6$) are injected intravenously into lethally irradiated hosts (950 Rad). After 5 days 3 μCi of 5'-[$^{125}$I]iodo-2'-deoxyuridine ($^{125}$I-dUrd) is injected intravenously. The next day mice are sacrificed, their spleens removed and the incorporated radioactivity measured. The syngeneic control is engraftment of H2b marrow (5×10$^6$ cells) in lethally irradiated H2b hosts. For Ly49C blockade studies mice are given an intraperitoneal injection of 100 μg of 5E6 F(ab')$_2$ fragments 16 hr prior to irradiation and transplant of 2.5×10$^6$WBM cells from BALB/C donors. The syngeneic control for this receptor blockade experiment is transplant of 2.5×10$^6$H2b BM cells into syngeneic hosts. This statistical significance of differences in the means between experimental groups is assessed by the Mann-Whitney U-test. For analysis of survival and GVHD following allogeneic marrow transplantation, 5×10$^6$ WBM cells are transplanted into mice that receive 950 Rads as a single dowse. The mice are kept on acidified water for the first 4 weeks post-transplant. Mice are weighed two times per week for the first 6 weeks and then weekly. Mice are observed daily for evidence of sever GVHD including hunched posrue, alopecia, inflammation or bleeding of mucous membranes during the first four weeks post-transplant and then twice weekly. Analysis of the survival differences between SHIP$^{-/-}$ and SHIP$^{+/+}$ mice in the GVHD study is done using the Kaplan-Meier log-rank test and confirms that the survival of SHIP$^{-/-}$ mice is dramatically enhanced relative to their SHIP$^{+/+}$ littermates.

EXAMPLE 2

SHIP−/− Transgenic Mice

In order to demonstrate the role that SHIP plays in NK biology, mice are developed in which the first exon and promoter of the SHIP gene are flanked by loxP sites, and the first exon is deleted by mating these mice with Cre transgenic mice (FIGS. 1A,B). The SHIP genomic locus is isolated from a 129SVJ mouse genomic library (IFIX vector, Stratagene, San Diego, Calif.), partially subcloned and sequenced to identify the SHIP first exon and genomic regions that flank the SHIP promoter and first exon. A 2.3 Kb XbaI-BamHI fragment that is immediately 5' to the SHIP first exon and promoter, a 1.7 Kb BamHI fragment containing the SHIP promoter and exon 1 and a 2.8 kB BamHI-Sau3A fragment 3' to the first exon are inserted into the pFlox plasmid to yield the SHIP targeting vector. The correct orientation and integrity of these SHIP genomic fragments in pFlox are confirmed by restriction mapping and sequencing. The SHIP targeting vector is then linearized with SspI and electroporated into the TL1 ES cell line and stable integrants selected by culture in the presence of G418. Genomic DNA from G418 resistant ES cell clones is digested with SpeI and XhoI, resolved by electrophoresis, transferred to nitrocellulose and probed with a 0.8 kB PstI-KpnI probe that flanks the 3' arm of homology in the SHIP targeting vector. These blots are stripped and reprobed with an HSV-TK cDNA probe to confirm that the ES cell clones with 8.7 kB fragment diagnostic of homologous recombination contain only a single integration of the targeting vector. The neo/HSV-TK selection cassette, itself flanked by loxP sites (foxed), is removed from homologous recombination ES cell clones by transient expression of the Cre recombinase. ES cell clones harboring this deletion are identified by PCR and Southern blot analysis. ES cell clones with the "foxed" SHIP locus that is prepared for deletion of the SHIP promoter and exon 1 by Cre-mediated deletion are used to generate chimeric mice. Chimeras are intercrossed with C57BL6/J mice and offspring carrying ES cell chromosomes identified by coat color. Offspring that inherited the SHIP$^{flox}$ allele are identified by PCR analysis. SHIP$^{flox}$ mice are mated to a Cre transgenic deleter strain and progeny with the expected deletion of the SHIP promoter and first exon (SHIP null allele) are identified by PCR analysis. The SHIP null allele is then backcrossed to the C57BL6/J background to the F4 generation and F4 SHIP$^{+/-}$ heterozygous mice are intercrossed to yield SHIP$^{+/+}$ and SHIP$^{-/-}$ littermates for test groups. Mice are genotyped by a PCR assay that amplifies genomic DNA prepared from ear punches that are diagnostic for the presence of the null or wild type SHIP alleles or both. The primers that amplify the 5 Kb and 0.4 kB DNA fragments diagnostic for the wild-type and null alleles, respectively, are

```
5'-AGTCACGTCCCACCATCCTATG-3'      (SEQ ID NO. 1)
and

3'-CCACAAGTGATGCTAAGAGATGC-5'.    (SEQ ID NO. 2)
```

The primers that amplify the 0.8 kB allele diagnostic for the wild-type allele are

```
5'-ATG AAG GGT CCC TTG TAG AG-3'   (SEQ ID NO. 3)
and

3'-CTG TGA GCA ACA CTA TTC CC-5'.  (SEQ ID NO. 4)
```

The cycling conditions for these primers are 94° C. for 4 min; followed by 35 cycles at 94° C. for 45 s, 55° C. for 45 s, and 72° C. for 6 min; ending with 10 min at 72° C. Ablation of SHIP expression is confirmed by Western blotting of spleen cells with the anti-SHIP monoclonal (P2C6) that detects all SHIP isoforms.

Mice with germline transmission of the "foxed" SHIP allele (SHIP$^{flox}$ allele) are then mated with transgenic mice that express Cre recombinase in germline gonadal tissues (CMV-Cre) (M. A. Bender et al., *Blood* 92, 4394-403, 1998). Because of this expression pattern, CMV-Cre$^+$SHIP$^{flox/+}$ male mice yield progeny with germline transmission of a SHIP null allele due to deletion of the first exon and promoter at the SHIP$^{flox}$ locus.

FIG. 1A shows genetic modification of the SHIP locus in mouse ES cells: configuration of (i) the wild-type SHIP locus; (ii) the targeting vector; and (iii) the SHIP locus after homologous recombination by the targeting vector; (iv) the deletion of the neo/HSV-TK cassette in vitro by Cre-mediated recombination results in ES cell clones with a "foxed" SHIP locus (SHIP$^{flox}$) used to generate chimeric mice; and (v) the SHIP null allele created by intercrossing of SHIP$^{+/flox}$ mice with Cre deleter mice results in the in vivo deletion of the SHIP first exon and promoter in SHIP$^{+/flox}$/CMV-Cre$^+$ progeny. SHIP$^{+/flox}$/CMV-Cre$^+$ mice were crossed with C57BL6/J mice and progeny that inherited the SHIP null allele in the absence of the CMV-Cre transgene are identified. Progeny that inherited the SHIP null allele are backcrossed to C57BL6/J out to the F4 generation. Intercrosses of F4 SHIP$^{+/-}$ mice are used to generate all wild-type and null homozygous littermates used in this study. SHIP exon 1 (black rectangle), lengths of diagnostic restriction and PCR fragments and a probe (gray rectangle) used for genotyping are shown. The targeting vector incorporates a neo/HSV-TK cassette flanked by loxP sites (black triangles) that allows selection of stable integrants in transfected ES cell clones. B, BamHI; K, KpnI; P, PstI; Sa, SalI; S, SpeI; X, XbaI.

FIG. 1B shows a Southern blot of genomic DNA from wild-type ES cells and the homologous recombinant clone G9 digested with SpeI and XhoI. When hybridized with a probe that flanks the 3' arm of homology in the targeting vector (gray rectangle in A), DNA from wild type cells shows the expected 23 kb band, while DNA from G9 cells shows both the 23b wild type band and the 8.7 kb band indicative of homologous integration into the SHIP locus. After hybridization with the 3' flanking probe, the filter is stripped and reprobed with an HSV-TK cDNA probe to confirm that the homologous recombinant clone contains a single integration of the targeting vector.

In FIG. 1C, genotyping of intercrosses between SHIP$^{+/-}$ mice is shown. DNA is prepared from ear punches of weanlings and PCR reactions that simultaneously detect both wild-type and null SHIP alleles (upper panel) or only the wild-type allele (lower panel) are performed. This analysis shows that littermates 1 are 3 are null homozygous (−/−), 2 and 6 are heterozygous (+/−) and 4-5 are wild-type homozygous (+/+).

In FIG. 1D, Western blot analysis is used to confirm loss of SHIP expression in null homozygous littermates ($^{\#}$1,$^{\#}$3). Whole cell lysates from spleen cells are prepared from the litter of mice genotyped in (C) and blotted with an anti-SHIP monoclonal antibody (P2C6) that reacts with all SHIP isoforms. Stripping and reprobing of the filter with a monoclonal antibody specific for β-actin shows equal protein loading.

In summary, mice are identified with the SHIP null allele in the germline and backcrossed the SHIP null allele to the C57BL6/J background to the F4 generation. F4 SHIP null heterozygous mice (SHIP$^{+/-}$) are intercrossed to generate SHIP$^{-/-}$ mice and wild-type littermates for the studies described below (FIG. 1C). Most importantly, SHIP$^{-/-}$ mice lack expression of SHIP protein (FIGS. 1C,D).

EXAMPLE 3

Development of an Abnormal NK Cell Population in SHIP−/− Mice

The development of an abnormal NK cell population in SHIP$^{-/-}$ mice is shown, with reference to FIG. 2. By 8 weeks of life, SHIP$^{-/-}$ mice show a gross distortion of their NK cell repertoire and a loss of NK cell homeostasis that results in an increased number of NK cells in SHIP$^{-/-}$ mice.

To assess the development of the peripheral NK cell compartment in SHIP$^{-/-}$, mice are analyzed following weaning (3 weeks), at the onset of puberty (5 weeks), and in adult mice (8 weeks or older). To analyze the peripheral NK cell compartment, spleens are collected from mice at various ages, and a single cell suspension is prepared by NH$_4$Cl lysis of erythrocytes and stained with the antibodies against the NK-associated markers 2B4 (PE), NK1.1 (FITC) and CD3(APC). For analysis of the NK cell repertoire, cells are stained with 2B4, NK1.1 and anti-Ly49A (A1), -Ly49C/I (5E6), -Ly49D (4E5), -Ly49G2 (4D11) or -CD94 (Ebioscience, San Diego, Calif.). To distinguish Ly49C staining from Ly49I, cells are stained with NK1.1, Ly49C/I and Ly49I (YLI90). All biotin conjugates are revealed by StrepAvidin-APC. With the exception of the anti-CD94 antibodies and StrepAvidin-APC all FACS reagents are obtained from BD-Pharmingen (San Diego, Calif.). The statistical significance of FACS analysis is assessed by a two-tailed Students' T-test. Splenocytes are prepared and stained with the NK cell associated markers, 2B4 and NK1.1 (L. L. Lanier, *Annual Review of Immunology* 16, 359-93 (1998); W. M. Yokoyama, *Current Opinion in Immunology* 10, 298-305 (1998)). Analysis of mice at these stages of ontogeny (FIG. 2A) indicate NK cells develop normally in the absence of SHIP expression, but in adult animals an abnormal population of NK cells is present that express approximately 10-fold higher surface levels of the NK receptor, NK1.1 (subsequently referred to as NK1.1$^{hi}$ cells) (FIG. 2A).

Figure 2A:
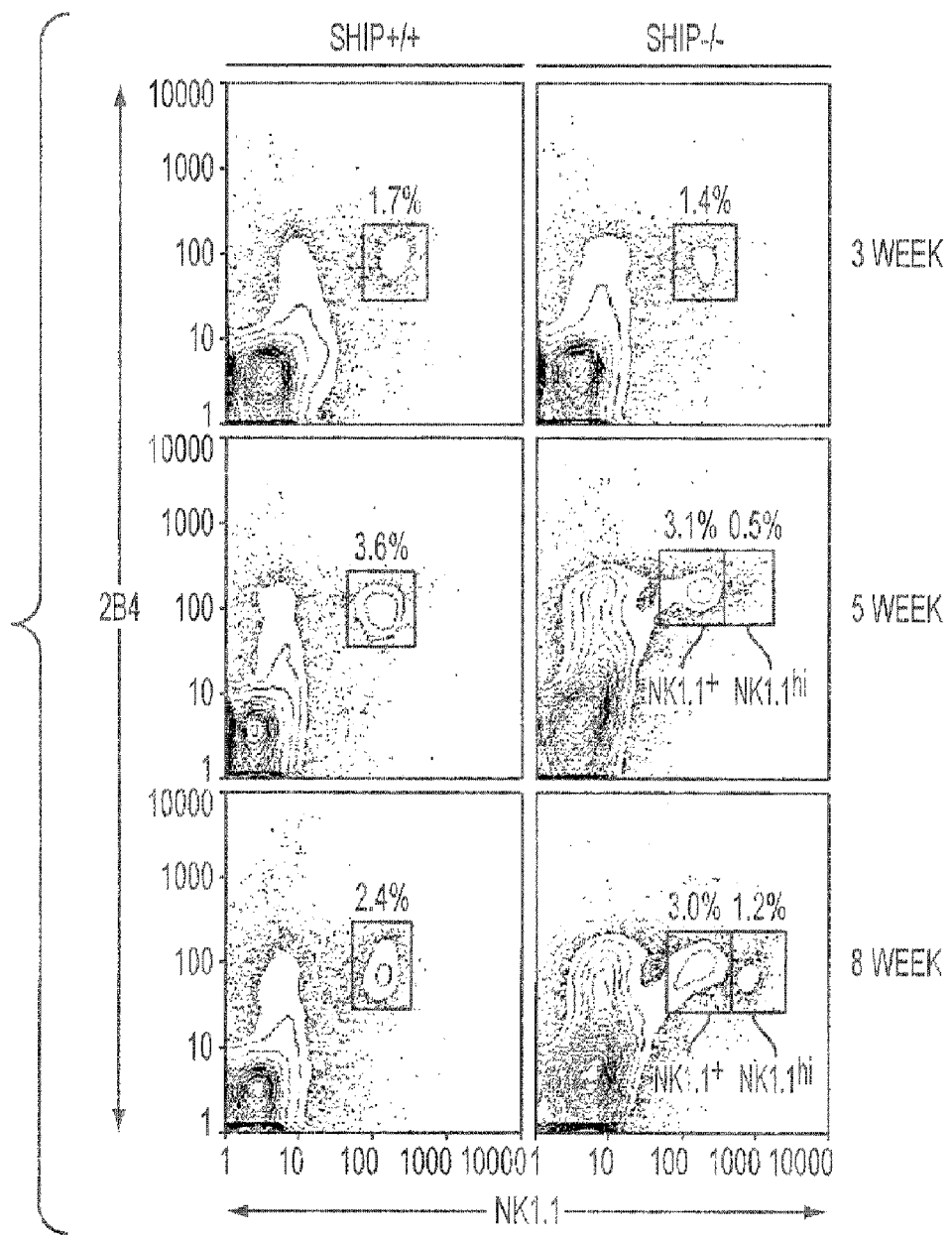
FIG. 2(A-C) illustrates flow cytometric analysis of the NK cell compartment of $SHIP^{+/+}$ and $SHIP^{-/-}$ mice.
Figure 2B:
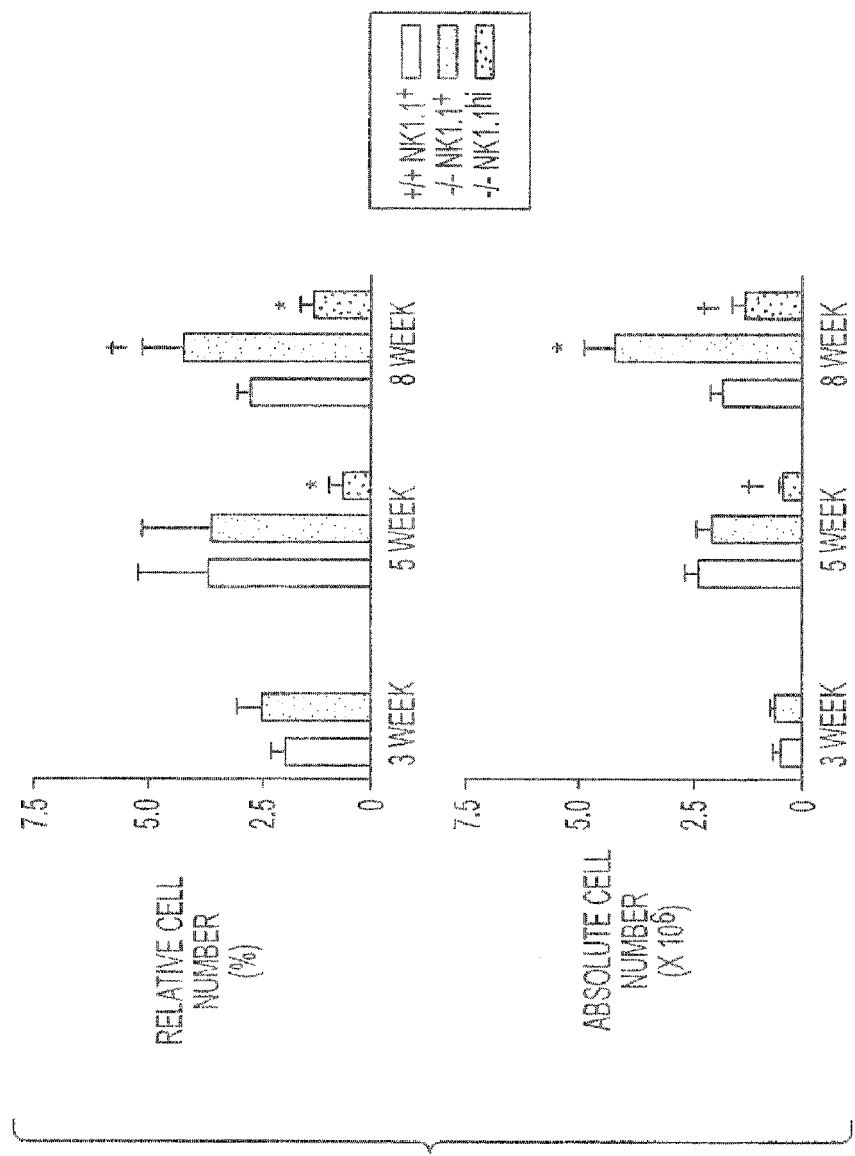
Figure 2C:
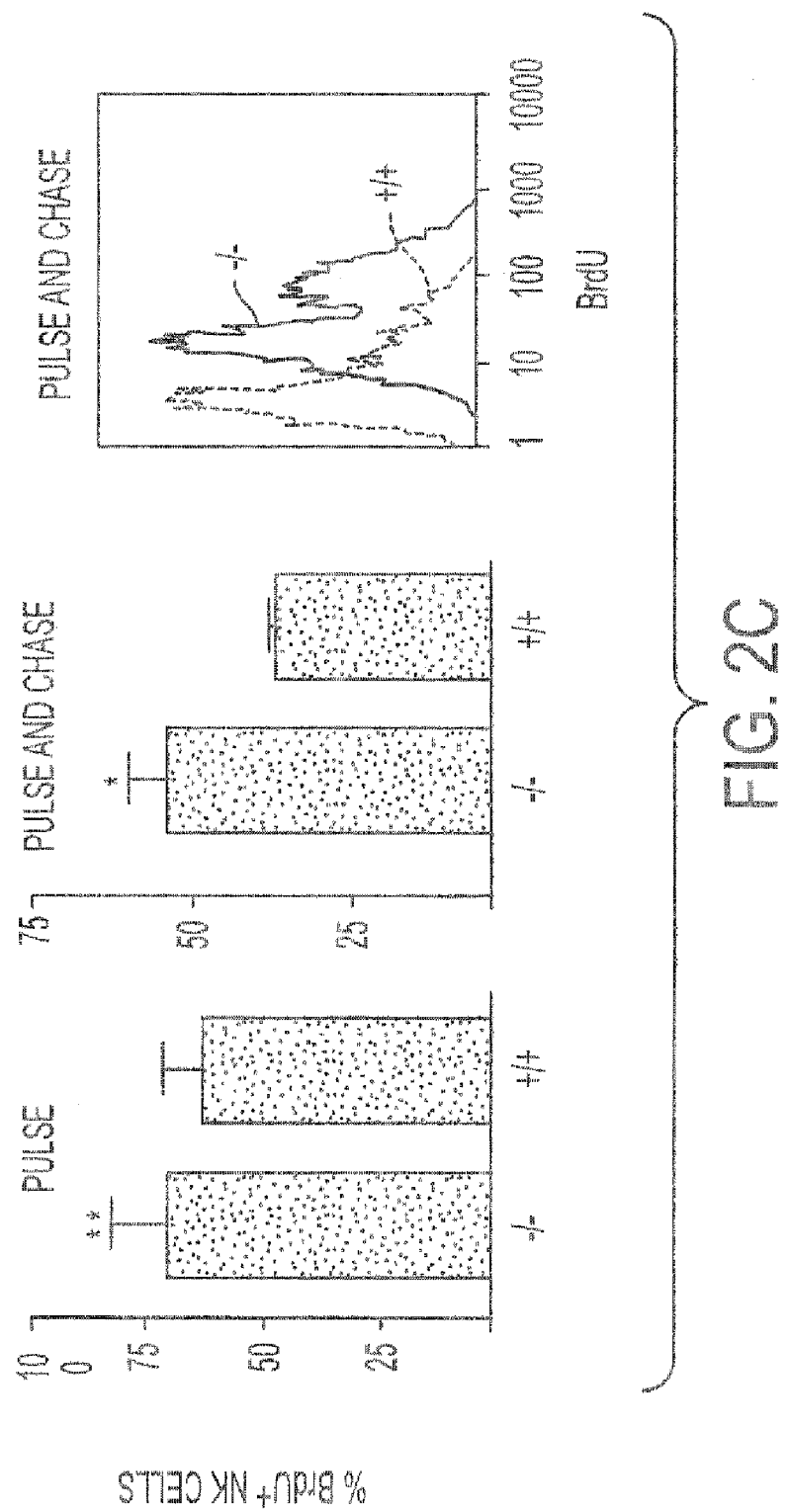

Thus, FIG. 2. illustrates increased NK cell numbers in SHIP$^{-/-}$ mice due to enhanced survival through flow cytometric analysis of the NK cell compartment: FIG. 2A provides FACS analysis of splenic NK cells in SHIP$^{+/+}$ and SHIP$^{-/-}$ littermates. Dual color contour plots of splenocytes stained with antibodies against the indicated markers. Results shown are representative of at least three mice from three separate litters. Genotype and age of the mice at the time of sacrifice and analysis are indicated. FIG. 2B provides bar graphs indicating the mean percentage of NK cells and the mean absolute number of NK cells in SHIP$^{+/+}$ and SHIP$^{-/-}$ mice at different ages. The values determined for SHIP$^{-/-}$ mice that are significantly different from that of their age-matched SHIP$^{+/+}$ counterparts, are indicated by the following symbols: *, p<0.05 and †, p<0.01. FIG. 2C provides percentage of BrdU labeled splenic NK cells in SHIP$^{+/+}$ (n=3) or SHIP$^{-/-}$ (n=3) mice immediately following one week on BrdU drinking water (Pulse) or after a two week chase (Pulse+Chase). P-values. **P=0.2 for SHIP$^{-/-}$ versus SHIP$^{+/+}$ in the Pulse analysis, *P=0.05 for SHIP$^{-/-}$ versus SHIP$^{+/+}$ in the Pulse+Chase analysis. Representative histograms for BrdU laberling of NK1.1$^+$CD3$^-$ cells from =/= and −/− animals in the Pulse+Chase group are shown.

The NK1.1$^{hi}$ population lacks CD3 and thus is not an NK-T cell population. Although the NK1.1$^{hi}$ population is most abundant in the spleens of adult mice, it is also detected as a small population as early as 5 weeks of life (FIGS. 2A,B). In addition, the relative and absolute number of NK cells with the normal 2B4$^+$NK1.1$^+$ staining profile (FIG. 2A) (herein referred to as NK1.1 cells) are also increased in adult SHIP$^{-/-}$ mice (FIG. 2B). Post-weaning SHIP mice (3 weeks) and SHIP$^{-/-}$ mice at the onset of puberty (5 weeks) show no significant increase in the percentage or absolute numbers of NK cells as compared to SHIP$^{+/+}$ littermates (FIG. 2B) indicating that NK cell homeostasis is normal in weanlings and juvenile mice. However, homeostasis is severely disrupted in adults (>8 weeks) resulting in increased numbers of both NK1.1$^+$ cells and the emergence of the abnormal NK1.1$^{hi}$ population that constitutes approximately 30% of the peripheral NK cell compartment in adult SHIP mice (FIG. 2B). Both the NK1.1$^{hi}$ population and increased numbers of NK1.1$^+$ cells are found in all adult SHIP$^{-/-}$ mice examined (8-19 weeks of age). Thus, the loss of homeostasis in adult SHIP$^{-/-}$ mice leads to an approximately three-fold increase in total NK cells in the periphery of SHIP$^{-/-}$ mice relative to wild-type littermates (FIG. 2B). SHIP deficiency leads to an NK inhibitory repertoire that is both self-specific and promiscuous for other ligands. Without being limited by theory, the loss of NK cell homeostasis may represent a failure of these cells to die due to unopposed PI3K/Akt signaling. A potential explanation for the repertoire disruption seen in SHIP$^{-/-}$ NK cells is that SHIP is recruited to certain inhibitory receptors expressed by NK cells to oppose intracellular signals that mediate survival of specific NK subsets expressing these receptors. Indeed, SHIP binds the phorphorylated ITIM motif of Ly49A in vitro.

Figure 3:
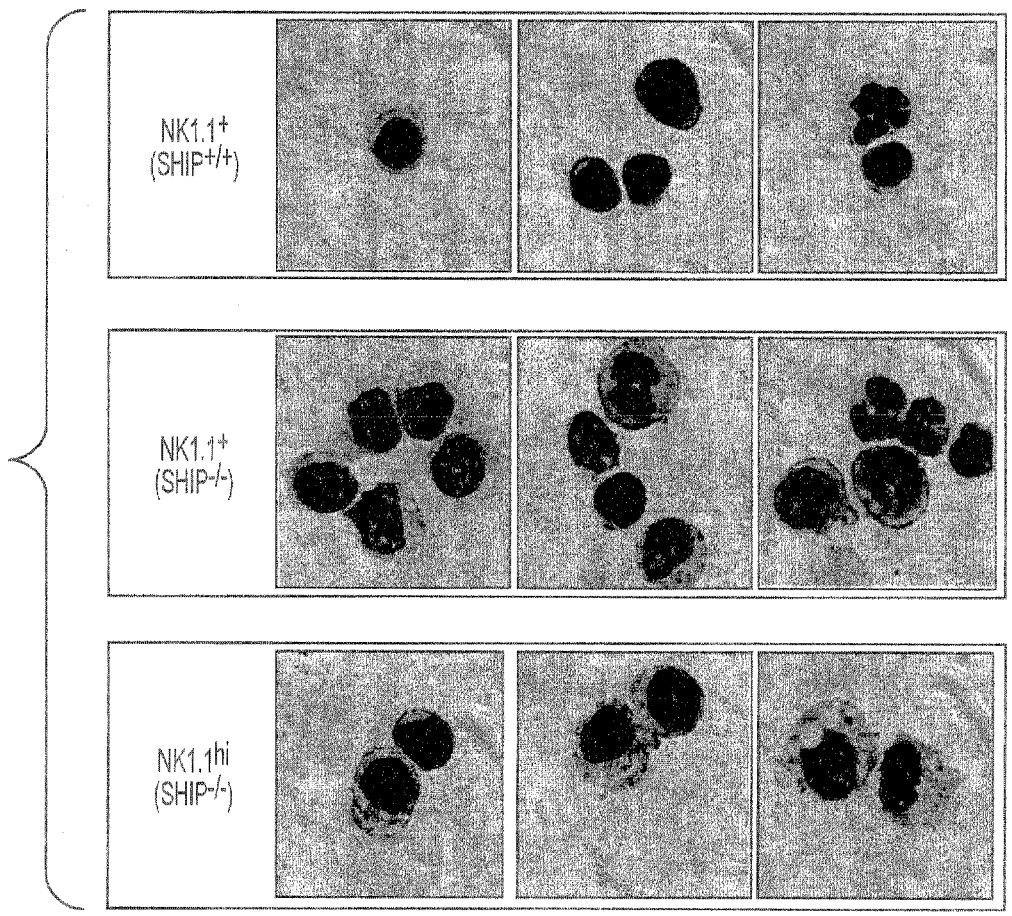
FIG. 3 illustrates Wright-Giemsa stained SHIP NK cells in which $SHIP^{-/-}$ cells exhibit abnormal morphology.

The alteration in NK cell populations shown herein is accompanied by alteration in the morphology of SHIP$^{-/-}$ NK cells, as shown in FIG. 3.

It is thereby shown in this example that the absence of SHIP function greatly influences how NK cells perceive their cellular milieu in vivo, and therefore it is shown that SHIP influences normal NK cell function. NK cells actively survey cells for MHC class I and ignore cells that have normal levels of all MHC class I haplotypes. If a departure from normalcy is detected (for example, an MHC class I haplotype normally expressed in the body is missing on a cell) then NK cells kill the aberrant cell: this is known to he how NK cells survey the body for virally infected cells or tumor cells. Such cells as these can lose MHC class I surface expression and thereby avoid T cells.

EXAMPLE 4

MHC Class I Repertoire of SHIP$^{-/-}$ Mice

Receptors that enable self/non-self recognition by lymphocytes play a critical role in their activation and differentiation into effector cells. These receptors also play a critical role in the homeostasis of these lineages through effects on their survival and proliferation in the periphery. Homeostasis in the NK cell compartment of SHIP$^{-/-}$ mice is lost at a time when the NK cell repertoire is normally established, and the repertoire is altered in the NK cell compartment of adult SHIP$^{-/-}$ mice as shown in this Example.

Figure 4A:
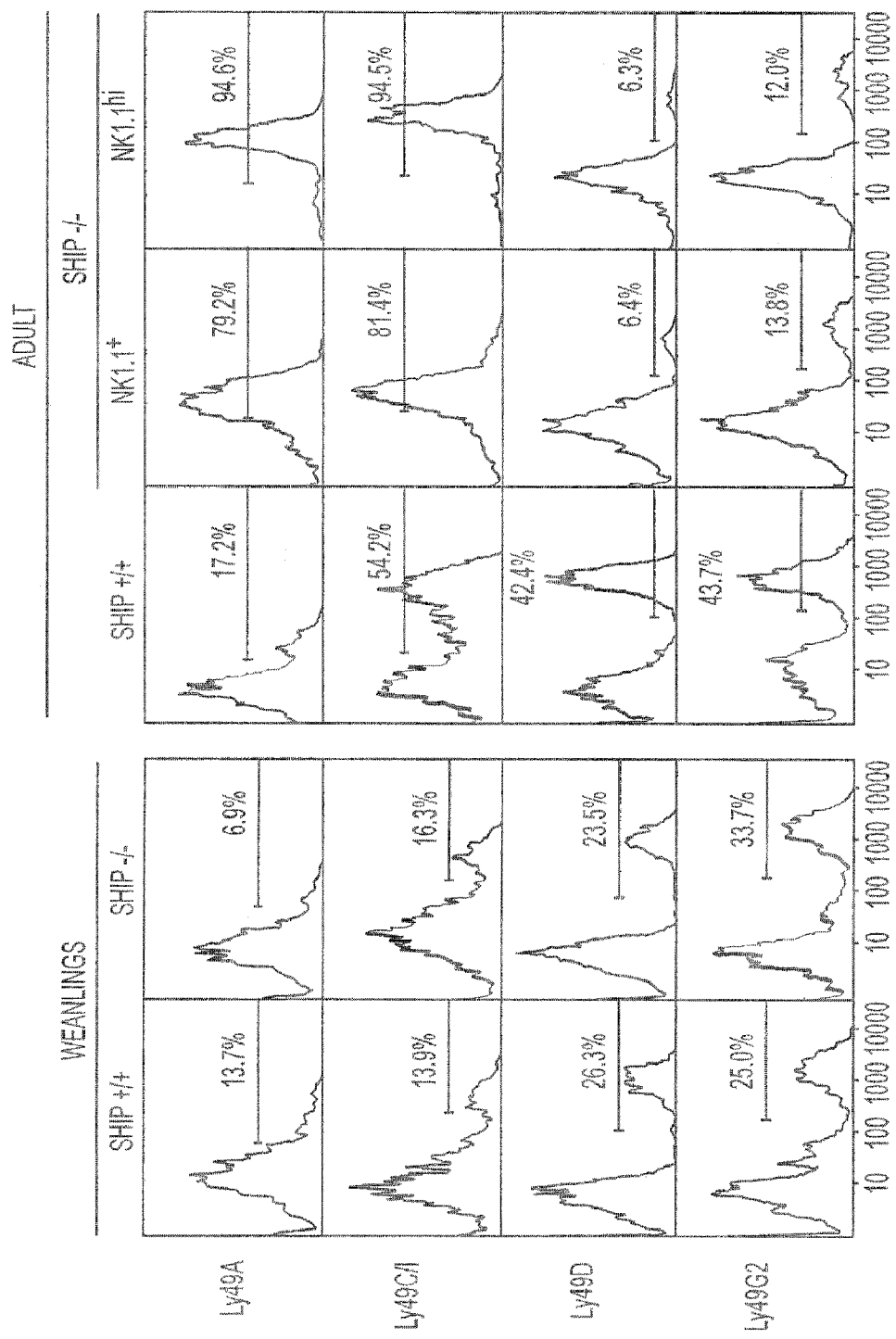
FIG. 4(A-D) illustrates flow cytometric analysis of MHC class I receptors expressed by NK cell populations in $SHIP^{-/-}$ mice.
Figure 4B:
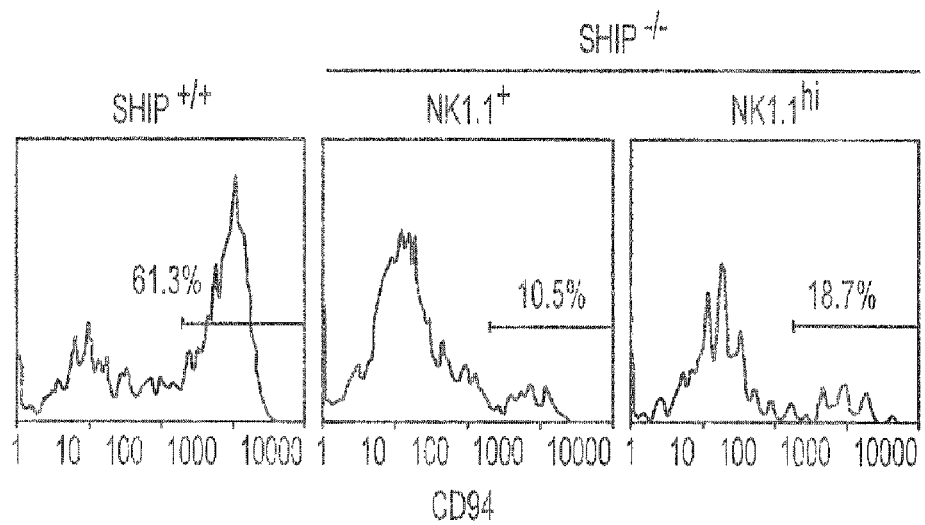

The repertoire of NK receptors for MHC class I molecules in SHIP$^{-/-}$ mice and their wild-type littermates is analyzed at discrete stages of ontogeny. Analysis of the expression of various Ly49 molecules and CD94 in weanlings (3 weeks) (FIG. 4A-D), in juvenile mice (5 weeks) (FIG. 4D) and in adult mice (8 weeks) (FIG. 4A-D) shows that the NK cell repertoire is significantly distorted in older SHIP$^{-/-}$ mice when compared to age-matched SHIP$^{+/+}$ littermates, but not in weanlings. SHIP$^{+/+}$ and SHIP$^{-/-}$ weanlings show no significant difference in the proportion of NK cells that express Ly49A, C/I, D, G2 and CD94 (FIGS. 4A,B,D). However, in juvenile mice only two weeks older, the repertoire of the NK compartment of SHIP$^{-/-}$ littermates is distorted toward the expression of Ly49A and C/I (FIG. 4D). This distortion is more pronounced in adult mice (8 weeks) and is found in both the NK1.1$^+$ and the NK1.1$^{hi}$ populations (FIG. 4A-D). Both of these NK populations in SHIP$^{-/-}$ mice are 80-90% positive for Ly49A and C/I (FIGS. 4A,B), with supernormal levels of these receptors found on the NK1.1$^{hi}$ cells (FIG. 4A). The expression of Ly49D, G2 and CD94 in the NK cell compartment of adult SHIP$^{-/-}$ mice shows the opposite trend with the percentage of NK cells expressing these molecules significantly reduced relative to wild-type littermates (FIGS. 4A,B).

Thus, in FIG. 4, flow cytometric analysis of MHC class I receptors expressed by NK cell populations in SHIP$^{-/-}$ mice is shown: (A) Histograms indicating expression of various Ly49 receptors or (B) CD94 on peripheral NK cells in SHIP$^{-/-}$ mice and their wild-type littermates. Spleen cells from 3 week old ("weanlings") or 8 week old (adult) SHIP$^{-/-}$ mice and their SHIP$^{+/+}$ littermates are stained with a combination of anti-2B4, anti-NK1.1 and anti-Ly49 or -CD94 antibodies. FIG. 4C histograms showing Ly49I expression on Ly49C$^+$ cells in the indicated NK1.1 population of adult SHIP$^{-/-}$ and SHIP$^{+/+}$ littermates. The gate used to calculate the percentage of NK cells that expresses the indicated Ly49 or CD94 molecule is shown by a horizontal black line above each histogram. All histograms are representative of analyses from at least three mice of identical age and genotype. FIG. 4D provides bar graphs indicating the mean percentage of NK cells that express the indicated Ly49 or CD94 molecule as determined in (A). The age and genotype of the mice are indicated. The values determined for SHIP$^{-/-}$ mice that are significantly different from that of their age-matched SHIP$^{+/+}$ counterparts are indicated by the following symbols: *, $p<0.05$ and †, $p<0.01$.

Figure 4C:
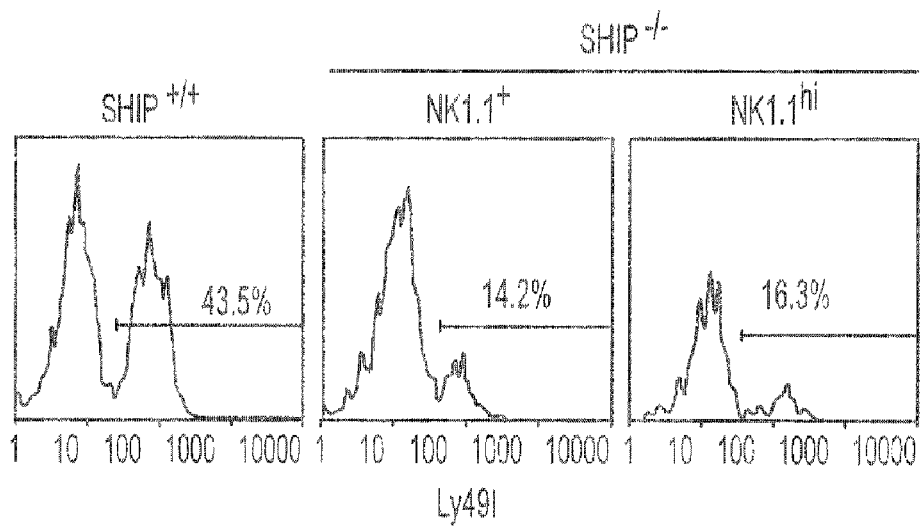
Figure 4D:
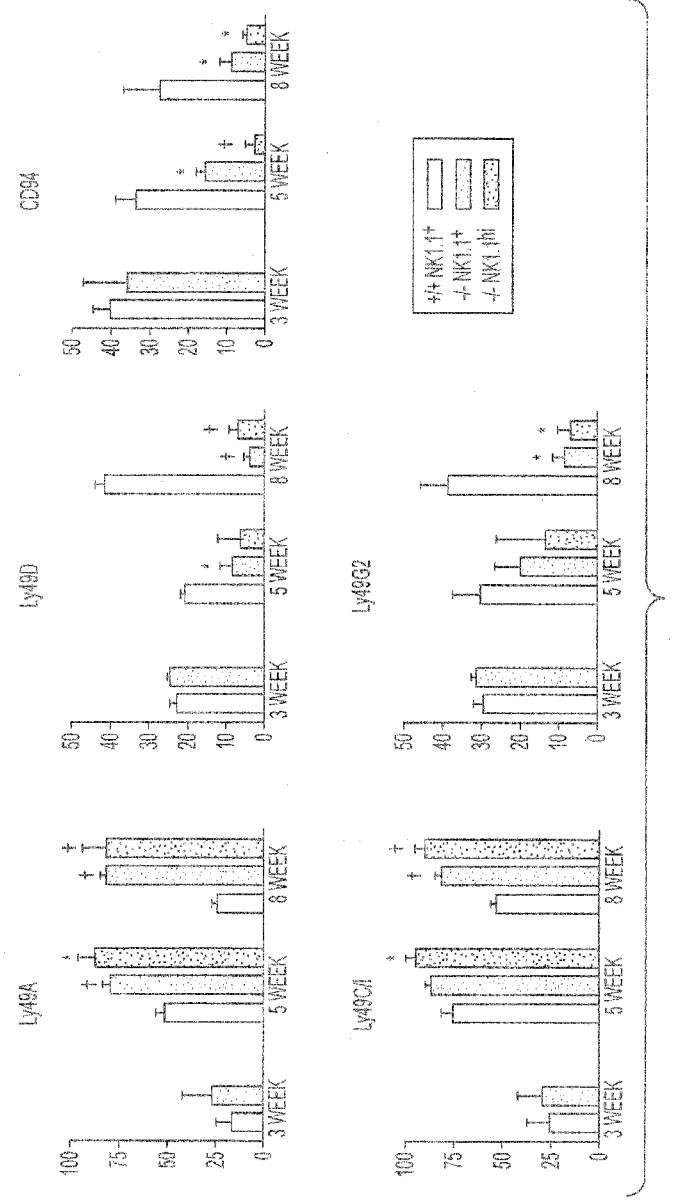

Ly49C/I staining is analyzed on adult NK cells in conjunction with an antibody specific for Ly49I (FIG. 4C), showing that both the NK1.1$^+$ and the NK1.1$^{hi}$ populations in adult SHIP$^{-/-}$ mice are predominantly Ly49C$^+$, since only a small proportion of Ly49C/I$^+$ cells express Ly49I (FIG. 4C). In contrast, nearly half of the Ly49C/I$^+$ NK cells in adult SHIP$^{+/+}$ express Ly49I (FIG. 4C). Thus, the repertoire distortion that occurs in the absence of SHIP signaling leads to an adult NK compartment that is dominated by a subset of cells with the following repertoire: Ly49A$^+$C$^+$D$^-$G2$^-$I$^-$CD94$^-$. In vitro and in vivo studies show that Ly49C and Ly49A can bind H-2$^b$ and H-2$^d$ class I ligands while Ly49D and Ly49G2 have specificity only for a ligand in the H-2$^d$ haplotype. Studies of Ly49A transgenic mice demonstrate that the H-2b haplotype possesses functional inhibitory ligands for Ly49A, since both anti-tumor and anti-viral responses by T cells expressing Ly49A are negatively impacted in the presence of the H-2b haplotype. Taken together, this demonstrates that both Ly49A and Ly49C are capable of binding and transmitting inhibitory signals from ligands present in all major murine WIC class I haplotypes, including H-2b. Thus, the MHC specificity of the NK inhibitory repertoire in adult SHIP$^{-/-}$ mice is both self-specific and promiscuous.

SHIP association in vivo with inhibitory Ly49 receptors expressed by NK cells is next shown. NK-enriched C57BL6/J splenocytes are prepared by depletion of B cells and macrophages by adherence to nylon wool followed by T cell depletion using anti-CD3 plus complement. NK cells are then lysed in modified RIPA buffer. Prior to immunoprecipitation the NK cell lysates are pre-cleared by incubation with 0.25 µg, of an IgG2a antibody (BD Pharmingen) and 80 µl of Protein G-Sepharose beads (Amersham Pharmacia). Immune precipitates bound to beads were pelleted at 15,000×g for 15 min at 4° C. The supernatants are immunoprecipitated with Ly49A, Ly49C/I, Ly49G2 and IgG2a by the sequential addition of 1-2 µg of the following antibodies to the pre-cleared lysates: anti-Ly49A (A 1), anti-Ly49C/I (5E6), Ly49G2 (4D11) and an IgG2a isotype control (BD Pharmingen, San Diego, Calif.). Immune complexes were brought down by addition of 50 µl of Protein G-Sephadex beads. Following each immunoprecipitation, excess antibody is removed by the addition of Protein G-Sephadex beads followed by centrifugation. The immunoprecipitates are resolved on a 4-12% Tris-Bis polyacrylamide gel and transferred to a nitrocellulose membrane (Amersham Pharmacia). The filters are then probed with a 1:1000 dilution of anti-SHIP (P2C6) and an anti-mouse IgG secondary antibody (Amersham Pharmacia) at a 1:100,000 dilution. The presence of SHIP is revealed using the SuperSignal West Femto reagent (Pierce). For analysis of Akt activation, lysates of purified NK cells from the spleens of SHIP$^{-/-}$ and SHIP$^{+/+}$ are prepared as above. Equal quantities of protein from cells lysates prepared from SHIP$^{+/+}$ and SHIP$^{-/-}$ NK cells are resolved on a 4-12% Tris-Bis polyacrylamide gel (Invitrogen), transferred to a nitrocellulose membrane (Amersham) and the filters probed with an anti-Akt-F'(Threo) antibody (Cell Signaling) at a 1:1000 dilution. The presence of Akt is detected by a donkey anti-rabbit IgG secondary antibody coupled to HRP (Amersham) at a 1:2000 dilution and revealed using ECL substrate (Amersham). The blot is then stripped and reprobed in a similar manner using an anti-β-actin antibody (Cell Signaling) as an internal control for protein loading.

Figure 5A:
FIG. 5(A-E) illustrates recruitment of SHIP to NK inhibitory receptors and opposition of Akt activation in vivo.
Figure 5B:
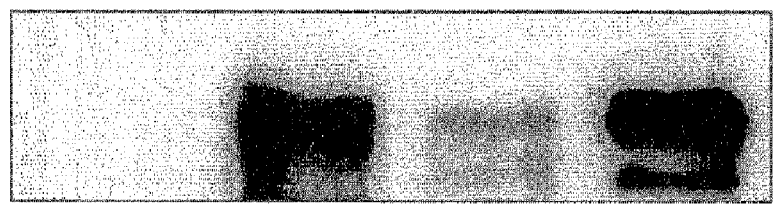
Figure 5C:
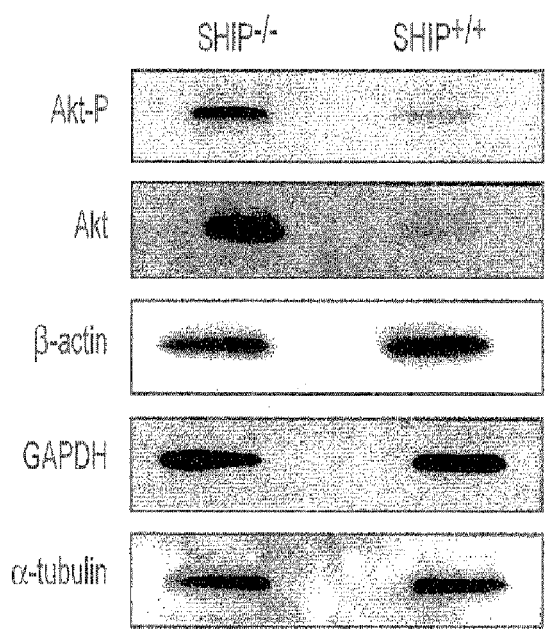
Figure 5E:
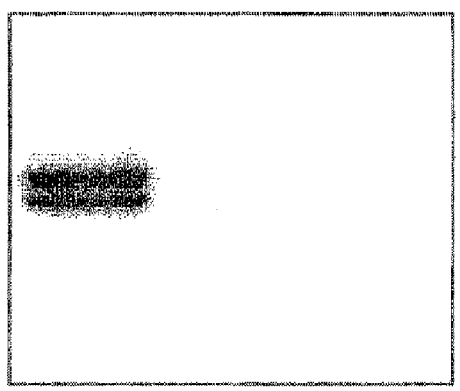
Figure 5E:
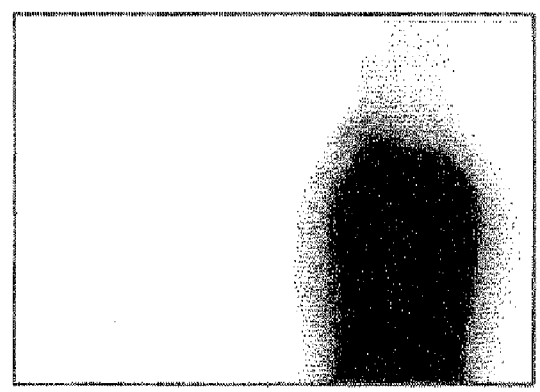

This analysis shows that SHIP associates with Ly49A and Ly49C, but not Ly49G2, under physiological conditions. Thus, in FIG. 5, SHIP is shown to be recruited to NK inhibitory receptors and to oppose Akt activation in vivo. FIG. 5A shows western blot detection of SHIP in Ly49 immunoprecipitates prepared from lysates of NK-enriched C57BL6/J splenocytes. A mock immunoprecipitation of the NK lysates with an IgG2a antibody is analyzed in parallel as a negative control. The results of these immunoprecipitations are representative of two independent analyses of NK-enriched splenocytes. FIG. 5B shows western blot analysis of SHIP in Ly49A and Ly49C immunoprecipitates prepared from lysates of SHIP$^{+/+}$ (+/+) and SHIP$^{-/-}$ (-/-) NK lysates. Immunoprecipitation of SHIP from NK cell lysates serves as positive control in both (A) and (B). In (A) a one-tenth exposure of the SHIP lane enables the 135/145 kD SHIP isoforms to be distinguished clearly. FIG. 5C shows western blot analysis of Akt activation using an antibody specific for Ala phosphorylated at Threo$^{408}$. To control for the amount of cell lysate loaded in each sample, the Akt-P blot is stripped and re-probed with an antibody specific for β-actin, GAPDH, and a tubulin. The detection of Akt activation is representative of three separate analyses of NK cell lysates from SHIP$^{-/-}$ and SHIP$^{+/+}$ mice. FIG. 5D shows Western blot detection of SHIP in Ly49A and Ly49C immunoprecipitates. Immunoprecipitation with a murine IgG2a antibody (IgG2a) is analyzed as a negative control and SHIP is immunoprecipitated as a positive control. FIG. 5E show Western blotting for SHIP in other Ly49 immunoprecipitates (Ly49G2, Ly49F, and Ly49I).

As further confirmation that the protein co-precipitating with Ly49A and Ly49C is SHIP, NK lysates from SHIP$^{+/+}$ and SHIP$^{-/-}$ mice are analyzed (FIG. 5B). SHIP is only co-precipitated in the SHIP$^{+/+}$ NK lysates.

Not to be limited by theory, but solely to clarify the possible mechanism of the present invention, SHIP and SHP-1 are both recruited to inhibitory Ly49 receptors, but at different times in the life of an NK cell. SHP-1 may be recruited to these receptors in activated NK cells to prevent inappropriate INK effector functions, while SHIP may influence the survival of specific NK cell subsets in vivo by counteracting the PI3K/Akt pathway that promotes their survival. Consistent with this, Akt/Protein Kinase B is activated in SHIP$^{-/-}$ NK cells in vivo based on its phosphorylation at Threonine 408, while Akt in SHIP$^{+/+}$ NK cells shows only basal level activation (FIG. 5C). Thus, SHIP can oppose activation of Akt in NK cells in vivo. In performing this function, SHIP likely prevents the survival and inappropriate expansion of specific NK subsets that express inhibitory receptors capable of recruiting SHIP to the membrane. This mechanism is consistent with the repertoire disruption seen in SHIP$^{-/-}$ mice where 90-95% on adult NK cells co-express Ly49A and Ly49C.

Figure 10:
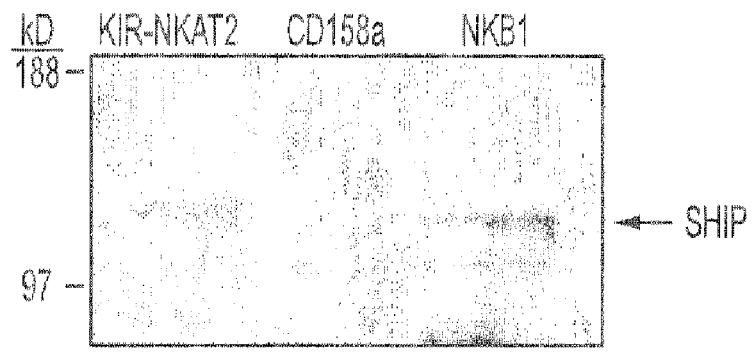
FIG. 10 illustrates that SHIP associates with killer inhibitory receptors (KIR) in human NK cells in vivo.

Significantly, we have shown that there exists a similar association between SHIP and human Killer Inhibitory Receptors (KIR), the human equivalent of the mouse MHC Class I Ly49 inhibitory receptors Ly49. Specifically, as shown in FIG. 10, human NK cells were enriched from peripheral blood mononuclear cells by magnetic depletion of B cells, T cells, monocytes, granulocytes and red blood cells with a cocktail of anti-CD19, -CD3, -CD4, -CD66b, and glycphorin A (StemSep, Vancouver), and the NK enriched fraction was lysed in RIPA buffer. Anti-bodies specific for the indicated KIR molecules and ProteinG+A-sepharose were used to immunoprecipitate the KIR molecules from human NK cell lysates. The immunoprecipitates were then resolved by SDS-Page and transferred to a blotting membrane. A Western blot of the immunoprecipitates indicates that SHIP is associated with some KIR (KIR-NKAT2, NKB1) in this individual. Mock immunoprecipitations with antibody isotype matched controls for the indicated KIR antibodies failed to immunoprecipitate SHIP (data not shown). Again, not to be limited by theory, the data in FIG. 10 show that SHIP is likely to influence signals that affect NK subset survival or proliferation and function via KIRs, probably because the cytoplasmic tails of both Ly49 and KIR have conserved ITIM motifs to which SI—HP binds to allow its recruitment to the membrane and access to its substrate, PIP3.

EXAMPLE 5

NK Cell Function in SHIP$^{-/-}$ Mice, and Effect Upon Graft Rejection

The severe distortion of the NK cell repertoire towards receptors with promiscuous specificity for ligands from many different MHC haplotypes increases the inhibitory signals received by these cells and may hamper their function. The ability of SHIP$^{-/-}$ and SHIP$^{+/+}$ NK cells from juvenile and adult mice to carry out cytolysis of an NK-sensitive allogeneic target cell (YAC-1) is assayed in this Example.

Figure 6:
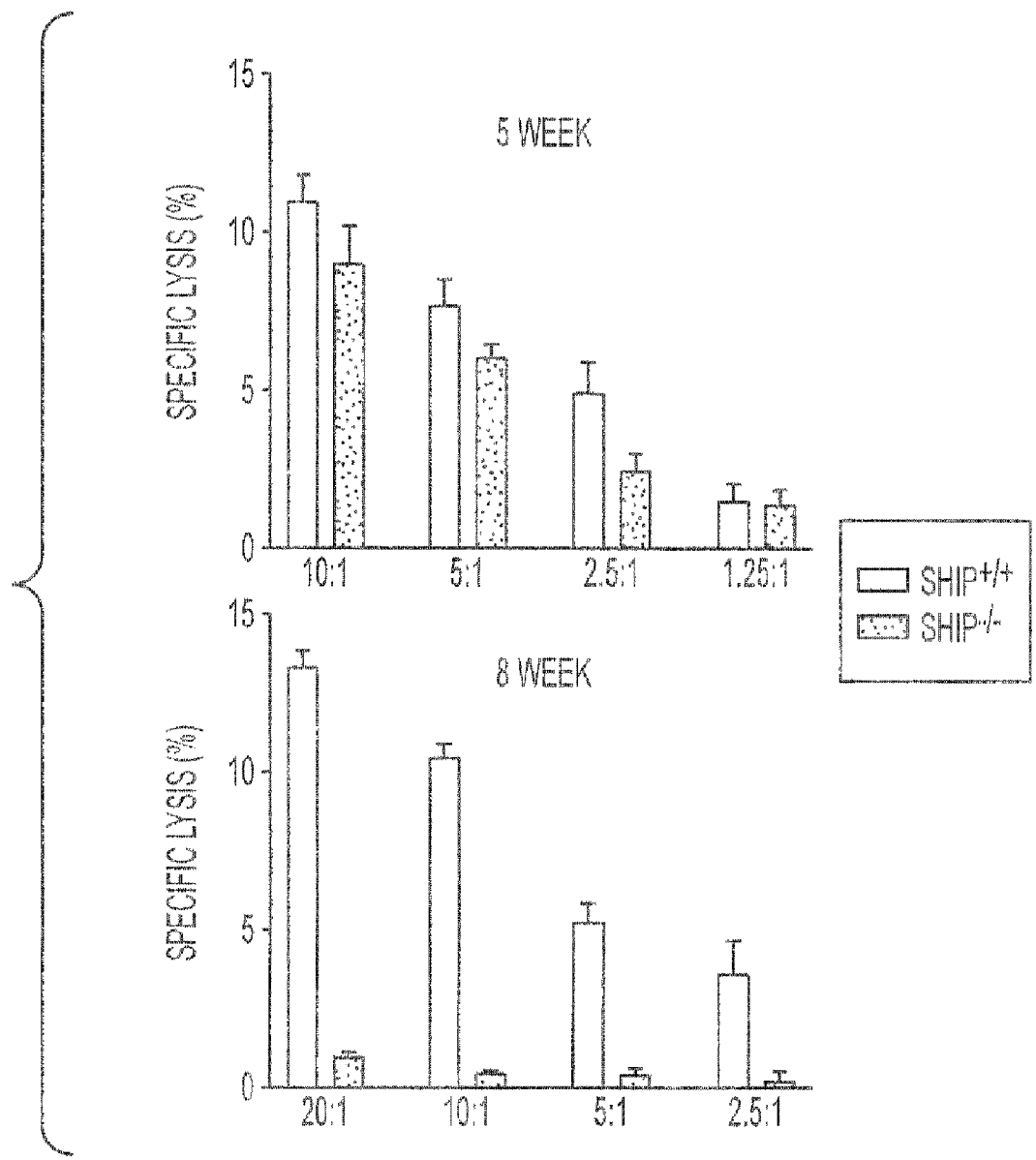
FIG. 6 illustrates inability of adult $SHIP^{-/-}$ NK cells to kill an allogeneic target cell.

YAC-1 cells are derived from A/Sn mice that have an H-2a haplotype. The results in FIG. 6 shows that there is no significant difference in the ability of wild-type and mutant NK cells from juvenile mice (5 weeks) to lyse target cells. However, purified SHIP$^{-/-}$ NK cells from adult mice (8 weeks) show severely reduced lysis of YAC-1 targets (FIG. 6). Splenic 2B4$^+$NK1.1$^+$NK cells were purified by FACS and analyzed for their ability to lyse an NK-sensitive target cell (YAC-1) in a standard $^{51}$Cr release assay at the indicated effector:target ratios (E:T). The percent specific lysis of target cells, by NK cells from SHIP$^{-/-}$ and SHIP$^{+/+}$ littermates of the indicated ages are shown in FIG. 6. The results are representative of three independent experiments using SHIP$^{+/+}$ and SHIP$^{-/-}$ littermates from three different litters. Adult SHIP$^{-/-}$ NK cells enriched following nylon wool depletion of adult splenocytes also fail to kill target cells.

SHIP$^{-/-}$ NK cells, however, showed reduced capacity to kill normal cells of the H-2s and H-2d MHC backgrounds. Whole bone marrow (WBM) cells are obtained from tibias and femurs of A/SW-(H-2s)/Sn (H-2s), BALB/C(H-2d) or β2 m$^{-/-}$ donor mice and washed once in PBS. WBM cells ($5\times10^6$) are injected intravenously into lethally irradiated hosts (950 Rad). After 5 days, 3 µCi of 5'-[$^{125}$I]iodo-2'-deoxyuridine (125I-dUrd) is injected intravenously. The next day mice are sacrificed, their spleens removed and the incorporated radioactivity measured. The statistical significance of differences in the means between experimental groups is assessed by a two-tailed Students' T-test. For analysis of survival and GVHD (Graft Versus Host Disease) following allogeneic marrow transplantation, $5\times10^6$ WBM cells are transplanted into mice that received 950Rads as a single dose. The mice are kept on acidified water for the first 4 weeks post-transplant. Mice are weighed two times per week for the first 6 weeks and then weekly. Mice are observed daily for evidence of severe GVHD including hunched posture, alopecia, inflammation or bleeding of mucous membranes during the first four weeks post-transplant and then twice weekly.

Figure 7A:
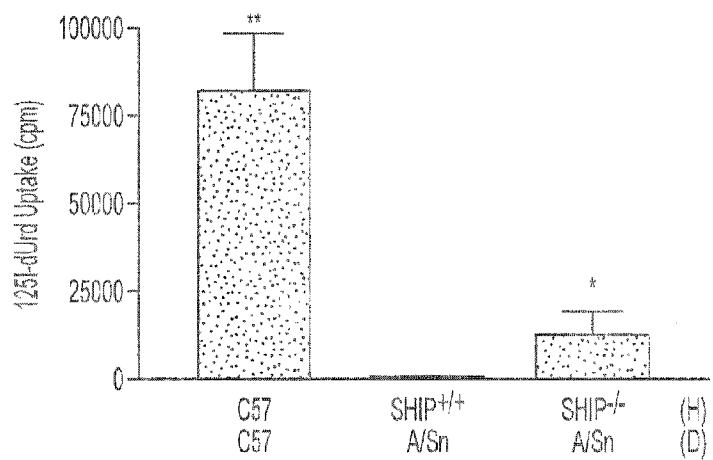
FIG. 7A shows the growth of A/Sw(H-2s)/Sn donor marrow in $SHIP^{+/+}$ or $SHIP^{-/-}$ (C57BL6/J) hosts (*p=0.0006 for $SHIP^{-/-}$ vs. $SHIP^{+/+}$, and **p=0.002 for $SHIP^{-/-}$ vs. positive control)

As shown in FIG. 7A, SHIP$^{-/-}$ mice are permissive for the growth of A/Sw(H-2s)/Sn marrow grafts while their SHIP$^{+/+}$ littermates reject these grafts. The inability of SHIP$^{-/-}$ NK cells to reject A/Sw(H-2s)/Sn marrow grafts is primarily due to the co-expression of Ly49A and Ly49C by an overwhelming proportion of the adult SHIP$^{-/-}$ NK cell compartment. Consistent with this proposed mechanism, the H-2s haplotype is also capable of binding and/or transmitting inhibitory signals via either Ly49A or Ly49C. Ly49D, an activating receptor that is down regulated in SHIP$^{-/-}$ mice, does not have a ligand in the H-2 haplotype and thus its under-representation in SHIP$^{-/-}$ mice is not responsible for acceptance of H-2s marrow grafts.

Figure 7B:
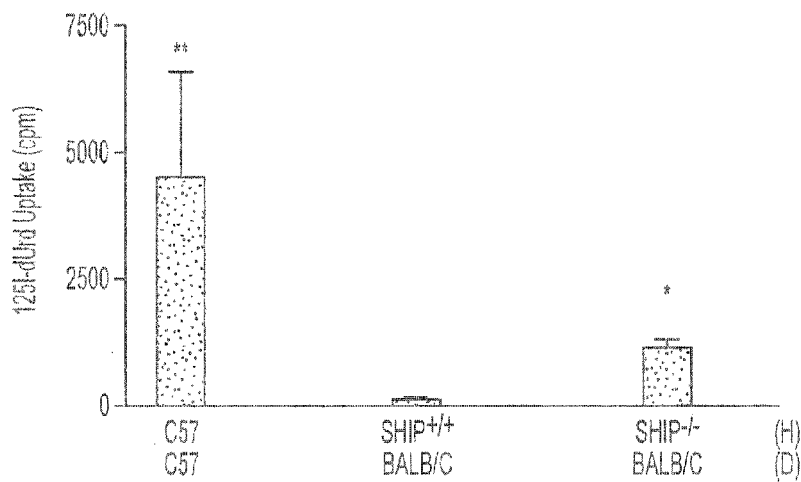
FIG. 7B shows the growth of BALB/C(H-$2^d$) (B) donor marrow in $SHIP^{+/+}$ or $SHIP^{-/-}$ (C57BL6/J) hosts (*p=0.0001 for $SHIP^{-/-}$ vs. $SHIP^{+/+}$, and **p=0.0633 for $SHIP^{-/-}$ vs. positive control)

NK killing of other histo-incompatible targets is also compromised in SHIP$^{-/-}$ mice, including killing of cells bearing other MHC haplotypes that bear MHC ligands bound by Ly49A and Ly49C. SHIP$^{-/-}$ mice cannot reject a fully allogeneic bone marrow graft from BALB/C mice whose H-2d haplotype forms strong interactions with both Ly49A and Ly49C. BALB/C marrow is not rejected by SHIP$^{-/-}$ mice, but their wild type littermates reject these fully histo-incompatible marrow grafts (FIG. 7B). Thus, SHIP$^{-/-}$ mice fail to reject allogeneic marrow grafts from either H-2d or H-2s donors, consistent with the observation that Ly49A transgenic mice on an H-2b background also fail to reject BALB/C marrow grafts.

Because Ly49A and Ly49C are highly promiscuous receptors capable of interactions with all major murine MHC haplotypes, SHIP$^{-/-}$ mice may be universal recipients for histo-incompatible marrow grafts of any MHC haplotype.

Figure 9:
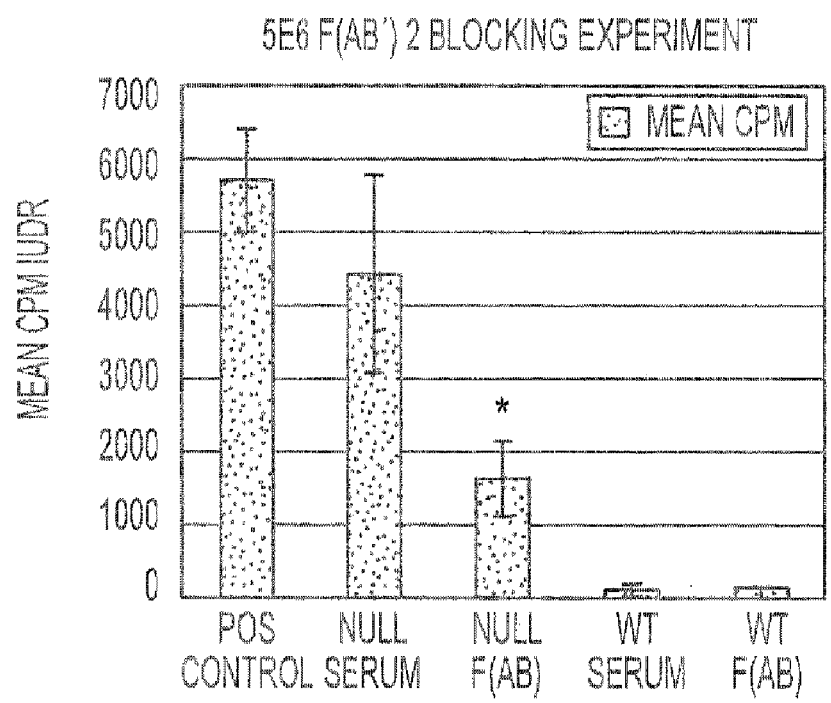
FIG. 9 illustrates that receptor blockade (Ly49C) partially restores rejection of histo-incompatible marrow grafts in $SHIP^{-/-}$ mice.

This is supported by the data in FIG. 9, which shows that in vivo blocking of Ly49C partially restores the ability of SHIP$^{-/-}$ mice to reject BALB/C(H-2D) marrow grafts. Specifically, anti-Ly49C F(ab')$_2$ fragments were injected into SHIP–/– (Null) and SHIP+/+ (WT) recipients 18 hr prior to lethal irradiation and these mice were transplanted with 2.5× 10$^6$ whole bone marrow (WBM) cells. Five days later the mice were injected with 3 µCi of 125I-UdR. The next day their spleens were removed and counted in a gamma counter to determine the degree of marrow growth. Mice treated with the F(ab')$_2$ fragment show significantly reduced growth of BALB/C marrow (*Null Serum vs Null Fab, p=0.0476) relative to SHIP$^{-/-}$ mice treated with normal mouse serum (Serum), indicating a partial restoration of marrow rejection due to blocking of the Ly$^{49}$C receptors over-represented in the SHIP$^{-/-}$ NK compartment. The effect is only partial, since SHIP$^{-/-}$ NK cells also over-express Ly49A and thus this inhibitory receptor may still render some SHIP$^{-/-}$ NK cells unresponsive to the allogeneic marrow cells. Positive control is C57BL/6 marrow transplanted into lethally irradiated C57BL/6 hosts. P-values determined by a Mann-Whitney U-test.

Figure 7C:
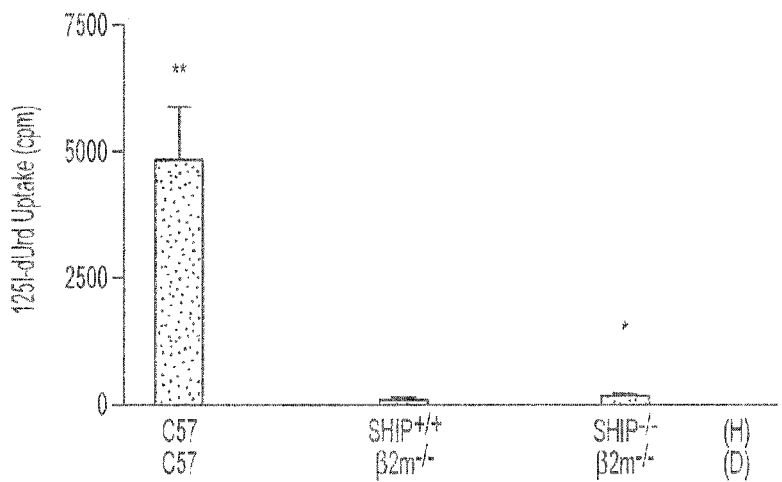
FIG. 7C is an analysis of "missing self" marrow graft rejection in $SHIP^{-/-}$ hosts, showing the growth of $\beta 2$ $m^{-/-}$ donor bone marrow in $SHIP^{+/+}$ (C57BL6/J) or $SHIP^{-/-}$ (C57BL6/J) hosts (*p=0.2894 for $SHIP^{-/-}$ vs. $SHIP^{+/+}$, **p=0.0001 for $SHIP^{-/-}$ vs. positive control). The positive control for engraftment in (A-C) is syngeneic transplants of C57BL6/J WBM into C57BL6/J hosts (D-donor, H-host).

An alternative explanation for the lack of an NK cell response against allogeneic targets is that the NK compartment in adult SHIP$^{-/-}$ mice is impaired. To exclude this possibility, the ability of SHIP$^{-/-}$ mice to reject a "missing self" marrow graft (MHC class I negative marrow from β2m$^{-/-}$ mice) is shown. FIG. 7C shows analysis of 10 separate adult SHIP$^{-/-}$ mice which reject β2 m$^{-/-}$ marrow grafts as do their 10 SHIP$^{+/+}$ littermates.

Thus, despite their inability to reject fully histo-incompatible marrow grafts, adult SHIP$^{-/-}$ NK cells still retain cytolytic activity against "missing self" targets in vivo. This is explained by the failure of β2m$^{-/-}$ target cells to engage Ly49A and C on SHIP NK cells leading to killing, whereas these receptors are engaged by MHC ligands on allogeneic targets to prevent killing by SHIP–/– NK cells.

EXAMPLE 6

Figure 8A:
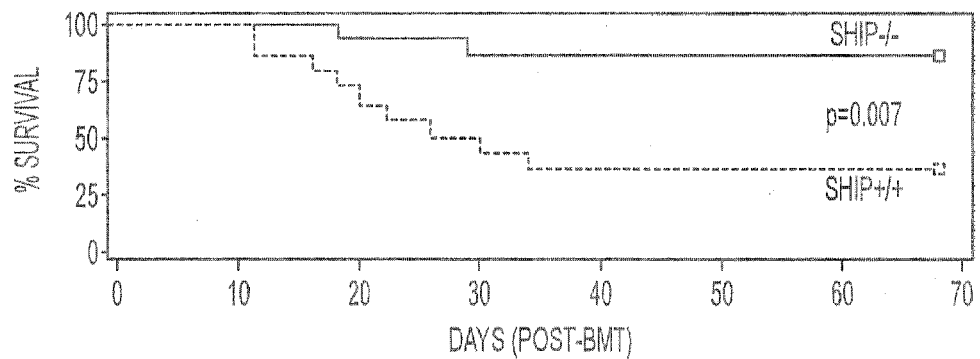
FIG. 8(A-C) illustrates the abrogation of GVHD disease in $SHIP^{-/-}$ hosts receiving fully-histoincompatible bone marrow grafts.
Figure 8B:
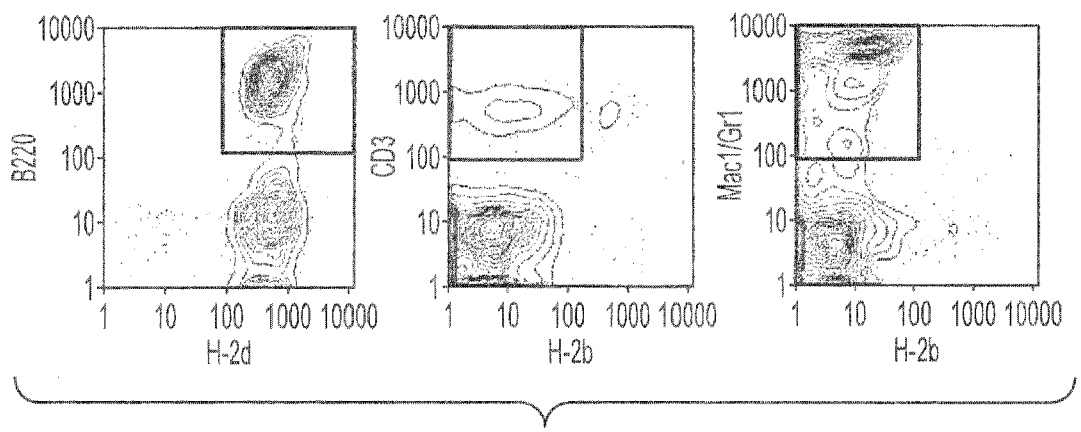

Inhibition of SHIP Prevents Rejection of Fully Histo-Incompatible Marrow Grafts and Prevents Graft-Versus-Host Disease The above Examples in an acute transplant setting demonstrate that SHIP$^{-/-}$ mice fail to reject a fully histo-incompatible marrow graft, but do not address whether engraftment of the donor marrow will result in severe graft-vs.-host disease (GVHD) and death. To address this question, a cohort of SHIP$^{-/-}$ mice and their SHIP$^{+/+}$ littermates were transplanted with whole bone marrow from BALB/C mice following lethal irradiation (FIG. 8). GVHD disease is abrogated in SHIP$^{-/-}$ hosts receiving fully-histoincompatible bone marrow grafts based on their enhanced survival and the absence of severe GVHD symptom. (FIG. 8A) Survival of SHIP$^{-/-}$ (n=14) and SHIP$^{+/+}$ (n=14) recipients on the C57BL6/J background that are transplanted with $5\times10^6$ WBM cells from BALB/C mice. Mice receive 950Rads prior to BM transplant. (FIG. 8B) FACS analysis of donor vs. host re-population for B cells (B220$^+$), myelo-granulocytic cells (Mac-1$^+$/Gr-1') or T cells (CD3) in peripheral blood of a representative SHIP$^{-/-}$ BMT survivor from (A). The rectangular gate used to assess the degree of donor (D) contribution to each lineage post-BMT is shown within the dual contour plots. (C) Donor repopulation of B cells, T cells and myelo-granulocytic cells in the 12 surviving SHIP$^{-/-}$ and 5 surviving SHIP$^{+/+}$ recipients in (A) as determined by multi-parameter FACS analysis of their peripheral blood (B).

Figure 8C:
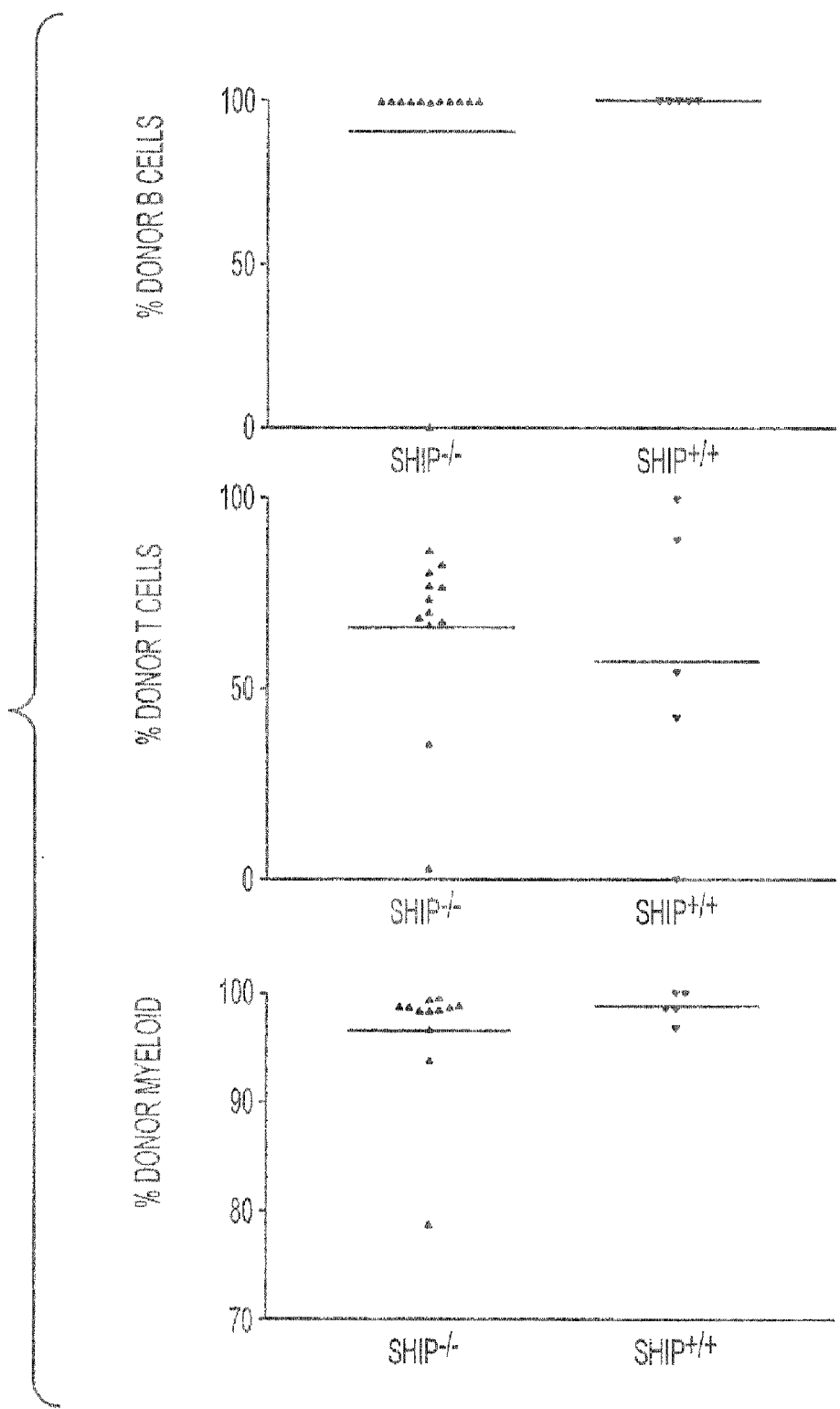

Eighty-six percent (86%) of the SHIP$^{-/-}$ mice survive lethal irradiation without developing GVHD out to 10 weeks post-transplant while only 36% survived in the SHIP$^{+/+}$ cohort. Analysis of the survival differences between the two cohorts using the Kaplan-Meier log-rank test confirms that survival of SHIP$^{-/-}$ mice is dramatically enhanced relative to their SHIP$^{+/+}$ littermates (p=0.007) (FIG. 8A). Nine of fourteen SHIP died during the 10 week post-transplant period and prior to death exhibit one or more signs of severe GVHD, including hunched posture, alopecia, weight loss and inflamed mucous tissues. The 12 of 14 surviving SHIP$^{-/-}$ mice show no evidence of severe GVHD up to 10 weeks post-transplant. To show that the transplanted mice are repopulated by BALB/C marrow, donor reconstitution by FACS at 7 weeks post-transplant is assessed (FIG. 8B) and it is found that 11 of 12 surviving SHIP$^{-/-}$ mice have full donor reconstitution of B-lymphoid and myelo-granulocytic cells (FIG. 8C) consistent with engraftment by stem/progenitor cells from the BALB/C marrow graft. The remaining SHIP$^{-/-}$ survivor is reconstituted by both host and donor stem/progenitor cells. Nearly all SHIP$^{-/-}$ hosts showed significant donor T cell reconstitution (FIG. 8C). The enhanced survival of SHIP$^{-/-}$ hosts demonstrates that SHIP not only plays a role in acute rejection of histo-incompatible marrow grafts by NK cells, but that SHIP also influences host factors that contribute to GVHD.

Because SHIP$^{-/-}$ NK cells fail to respond to histo-incompatible marrow grafts, (FIG. 7) and fail to develop GVHD, host NK cells are implicated in the initiation of GVHD. SHIP$^{-/-}$ mice reject "missing self" bone marrow grafts, but not histo-incompatible bone marrow grafts. (FIG. 7 A, B).

NK cells responding to allogeneic targets produce inflammatory cytokines ($\gamma$-IFN, TNF-$\alpha$) that contribute to GVHD. Not to be limited by theory, SHIP$^{-/-}$ NK cells fail to produce inflammatory cytokines in response to these grafts, thereby reducing the likelihood of a significant GVH reaction.

The expansion of an NK cell subset that expresses multiple Ly49 receptors specific for self MHC ligands in adult SHIP$^{-/-}$ mice means that SHIP signaling acts to prevent the survival or proliferation of such cells in vivo. Although Ly49 inhibitory receptors can block NK cell effector function, the interaction of these receptors with self WIC ligands also elicits signals that promote the survival or proliferation of these cells in vivo. Thus, SHIP counteracts these pathways and prevents the expansion of NK cells that express multiple self-specific MHC class I inhibitory receptors. SHIP performs this function in NK cells by opposing the PI3K/Akt pathway that influences survival and proliferation of both lymphoid and myeloid cells. Thus, it is shown herein that pharmaceutical inhibition of SHIP signaling limits the NK cell repertoire to subsets that co-express receptors specific for self MHC ligands. Therefore, it is further shown that modulating the NK repertoire in this manner compromises the host NK cell response to histo-incompatible marrow grafts that share some subset of host MHC class I ligands and thus facilitates engraftment in the absence of GVHD. Thus, inhibition of SHIP signaling is a means to increase the efficacy and utility of allogeneic bone marrow transplantation.

EXAMPLE 7

Figure 11A:
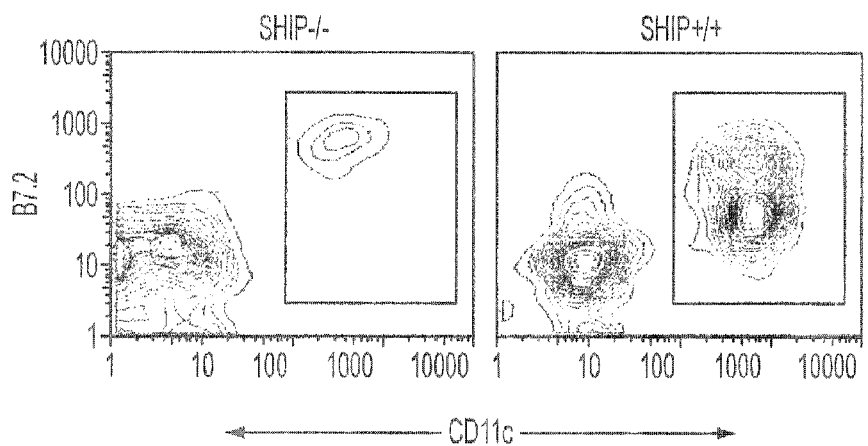
FIG. 11(A-C) illustrates that SHIP deficiency leads to decreased APC numbers and a decreased ability of APC to prime allogeneic T cell responses.
Figure 11B:
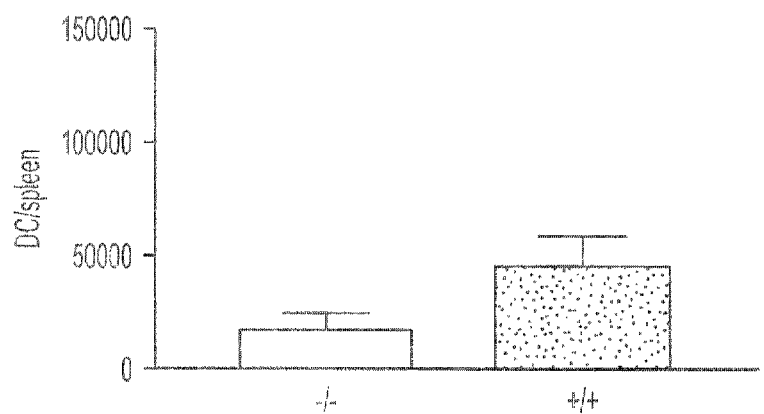
Figure 11C:
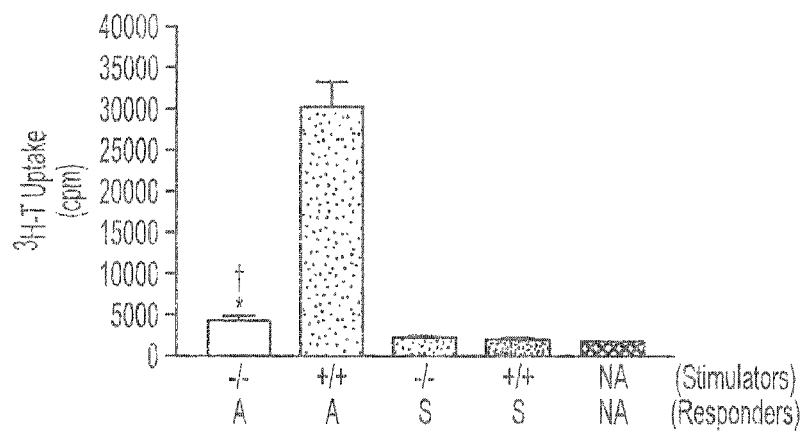

SHIP Deficiency Leads to Decreased APC Numbers and a Decreased Ability of APC to Prime Allogeneic T Cell Responses FIG. 11 illustrates reduction in dendritic cell number and function in SHIP$^{-/-}$ mice. FIG. 11A illustrates multi-color FACS detection of dendritic cell number in the spleens of SHIP$^{-/-}$ and SHIP$^{+/+}$ mice. Spleens are prepared by collagenase treatment and RBC lysis. The cell suspension is then stained with a "LIN" panel (CD3, B220, Gr1, Ter119 and NK1.1), CD11 and B7.2 The dual color contour plots in FIG. 11A show staining of CD11 and B7.2 on the LIN-fraction of the spleen. The percentage of splenocytes that are dendritic cells is determined by the indicated rectangular gate. FIG. 11B illustrates absolute dendritic cell number per spleen for SHIP$^{+/+}$ and SHIP$^{-/-}$ mice for each genotype. The number of dendritic cells is determined by multiplying the number of splenocytes obtained from an intact spleen by the percentage of dendritic cells in each spleen as determined by the FACS assay in FIG. 11A. FIG. 11C illustrates MLR using simulators irradiated splenocytes from +/+ and -/- mice on an H2 background. Responders are either syngeneic (S) T cells from BL6 mice or allogeneic (A) T cells from BALB/C mice. The hatched bar is 3H-T added wells with media without cells and is a control to determine background absorption of 3H-T.

In view of the fact that SHIP deficient mice have reduced numbers of dendritic cells and the fact that SHIP deficient dendritic cells have a severely compromised ability to stimulate allogeneic T cells relative to dendritic cells expressing normal levels of SHIP, methods to inhibit SHIP's expression, enzymatic activity of signaling activity could be used to compromise dendritic cell function. Inhibition of dendritic cell function in solid organ grafts prior to or during engraftment by blocking SHIP expression or function can be used to abrogate immune rejection of these transplants. In addition, treatment of patients who are about to receive allogeneic BM transplants with SHIP inhibitors can also be used to prevent GVHD from developing.

EXAMPLE 8

Ship Deficient Hosts are Universal Recipients Allogeneic Grafts

Figure 12:
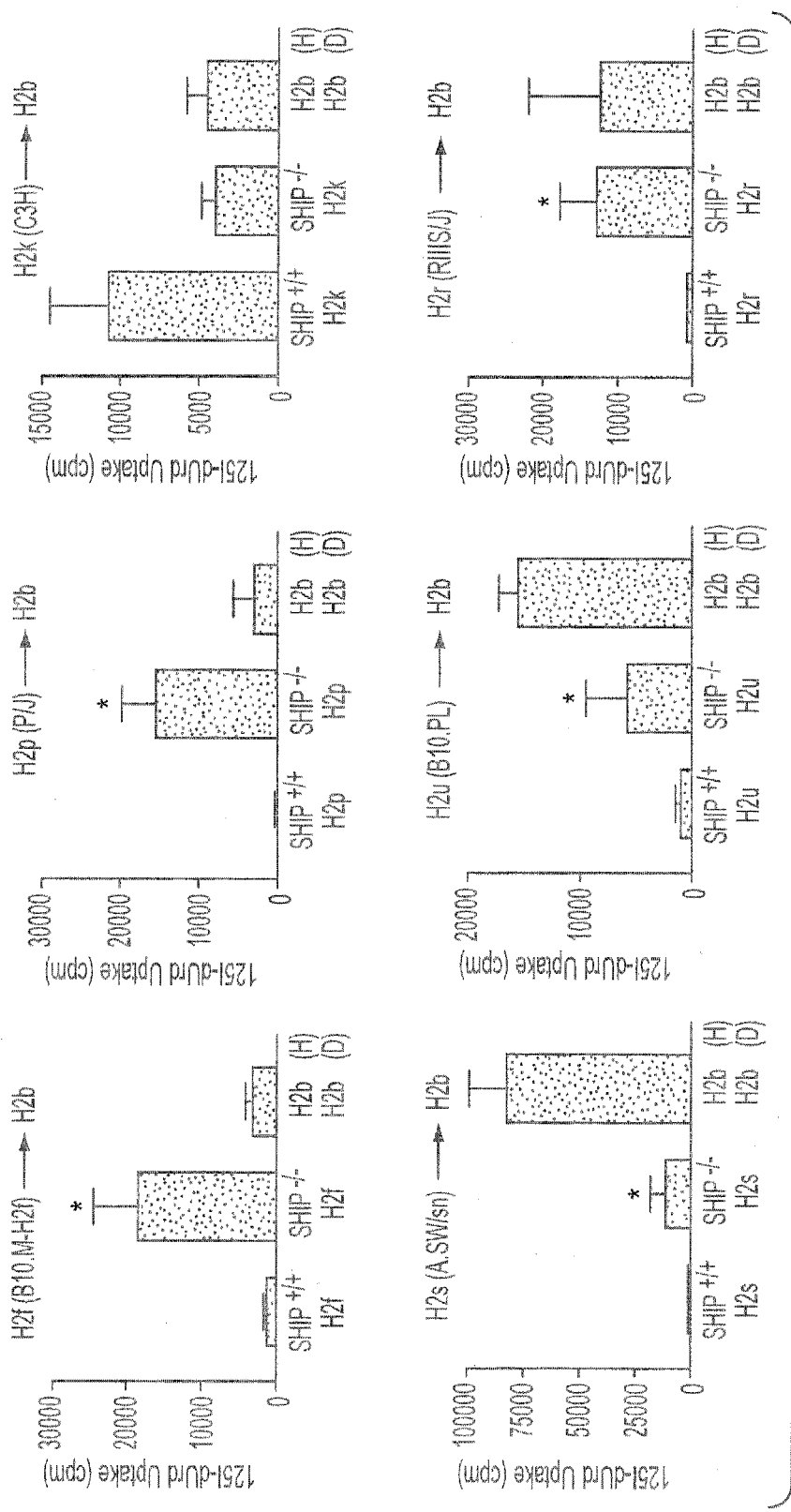
FIG. 12 illustrates that SHIP deficient hosts are universal recipients allogeneic BM grafts.

FIG. 12 illustrates the fact that SHIP deficient recipients fail to reject BM grafts from fully MHC-mismatched donors of all major mouse MHC haplotypes. SHIP$^{+/+}$ and $^{-/-}$ hosts (on an H2b background) are irradiated with a single dose of 950 Rads and then transplanted with a $5\times10^6$ whole bone marrow cells from various donors with full MHC mismatches. BM from all major H2 haplotypes is found to engraft including H2S, H2f, H2p, H2u and H2r. Engraftment of allogeneic donor BM into SHIP +/+ or SHIP -/- hosts is measured by splenic uptake of $^{125}$I-dUrd. All p-values for SHIP$^{-/-}$ vs. SHIP$^{+/+}$ littermates are p<0.05(*).

SUMMARY

Not to be limited by theory, the findings suggest an interplay of SHIP and PI3K may influence the relative survival of NK subsets expressing MHC class I receptors capable of recruiting these enzymes. Indeed transgenic mice with enforced expression of ly49A are unable to reject allogeneic bone marrow grafts from H2d donors. For example, BALB/C BM is not rejected by SHIP$^{-/-}$ mice, whereas their wild-type littermates can reject a similar graft. Further, SHIP$^{-/-}$, but not SHIP hosts, fail to reject H2s marrow grafts. It is thus proposed that over representation of an inhibitory receptor contributes directly to the compromised ability of SHIP$^{-/-}$ hosts to reject allogeneic BM grafts. The findings disclosed herein also support a previously unappreciated role for host NK cells in the initiation of GVHD. Likely, SHIP$^{-/-}$ NK cells fail to produce inflammatory cytokines in response to allogeneic BM cells, thereby reducing the likelihood of a significant GVH reaction by donor T cells. Alternatively, other host cell types that contribute to GVHD, such as antigen presenting cells could also be altered by SHIP deficiency. Further, although Ly49 inhibitory receptors prevent inappropriate killing by NK cells, the interaction of these receptors with self MHC ligands may also elicit signals that promote the survival or proliferation of these cells in vivo. SHIP may counteract these signals and thus prevent the expansion of NK subsets expressing more than one self-restricted inhibitory receptor. It is thus proposed herein, that inhibiting SHIP activity prior to BM transplant will restrict the NK inhibitory repertoire, such that selecting a donor with an appropriate MHC ligand, or ligands, might enable engraftment in the absence of GVHD.

Various publications, U.S. and foreign patent documents have been referred to herein, and each is hereby incorporated in its respective entirety by reference.

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

I claim:

1. A method for treating or reducing the probability of graft-versus-host disease (GvHD) in a human having or in need of a transplant, comprising administering to the human an efficacious amount of a substance that inhibits SH2-containing inositol-5-phosphatase (SHIP) expression in the human, wherein the substance comprises an interfering RNA specific for SHIP mRNA or an anti-sense polynucleotide specific for SHIP mRNA, and wherein the inhibition of SHIP expression treats or reduces the probability of GvHD.

2. The method of claim 1, wherein the transplant is a bone marrow allograft, a solid organ allograft or xenotransplant, or a major histocompatibility complex (MHC) disparate marrow graft having an MHC disparity of 1, 2, 3 or more allelic mismatches.

3. The method of claim 1, wherein the substance comprises the anti-sense polynucleotide.

4. The method of claim 1, wherein the human has cancer, autoimmune disease, HIV/AIDS, a genetic deficiency, or a combination thereof.

5. The method of claim 1, wherein the substance comprises the interfering RNA.

6. The method of claim 1, wherein the substance is administered prior to, or at the time of, the transplant.

7. The method of claim 1, wherein the substance is administered intravenously or intra-arterially.

8. A method for treating or reducing the probability of graft-versus-host disease (GvHD) in a human, comprising administering to the human: a transplant; and an efficacious amount of a substance that inhibits SH2-containing inositol-5-phosphatase (SHIP) expression in the human, wherein the substance comprises an interfering RNA specific for SHIP mRNA or an anti-sense polynucleotide specific for SHIP mRNA, and wherein the inhibition of SHIP expression treats or reduces the probability of GvHD.

9. The method of claim 8, wherein the substance comprises the interfering RNA.

10. The method of claim 8, wherein the substance comprises the anti-sense polynucleotide.

11. The method of claim 8, wherein the transplant is a bone marrow allograft, a solid organ allograft or xenotransplant, or a major histocompatibility complex (MHC) disparate marrow graft having an MHC disparity of 1, 2, 3 or more allelic mismatches.

12. The method of claim 8, wherein the human has cancer, autoimmune disease, HIV/AIDS, a genetic deficiency, or a combination thereof.

13. The method of claim 8, wherein the substance is administered prior to, or at the time of, administration of the transplant.

14. The method of claim 8, wherein the substance is administered intravenously or intra-arterially.

15. The method of claim 1, wherein the human has GvHD and the substance is administered to treat the GvHD in the human.

16. The method of claim 1, wherein the human does not have GvHD, and wherein the substance is administered to reduce the probability of GvHD in the human.

17. The method of claim 8, wherein the human has GvHD and the substance is administered to treat the GvHD in the human.

18. The method of claim 8, wherein the human does not have GvHD, and wherein the substance is administered to reduce the probability of GvHD in the human.

* * * * *

UNITED STATES PATENT AND TRADEMARK OFFICE
CERTIFICATE OF CORRECTION

| | |
|---|---|
| PATENT NO. | : 8,163,710 B2 |
| APPLICATION NO. | : 12/651809 |
| DATED | : April 24, 2012 |
| INVENTOR(S) | : William G. Kerr |

It is certified that error appears in the above-identified patent and that said Letters Patent is hereby corrected as shown below:

Column 2,
Line 61, "Rohrschneidcr" should read --Rohrschneider--.

Column 4,
Line 62, "CD94NKG2" should read --CD94/NKG2--.

Column 13,
Line 50, "neuronal stern" should read --neuronal stem--.

Column 14,
Line 16, "for Shr" should read --for 5hr--.

Column 15,
Line 17, "SHIP NK" should read --SHIP$^{+/+}$ NK--.

Column 17,
Line 1, "the "foxed" SHIP" should read --the "floxed" SHIP--.
Line 14, "a "foxed" SHIP" should read --a "floxed" SHIP--.

Column 19,
Line 1, "NK1.1 cells" should read --NK1.1$^{+}$ cells--.
Line 2, "SHIP mice" should read --SHIP$^{-/-}$ mice--.
Line 11, "SHIP mice" should read --SHIP$^{-/-}$ mice--.

Column 20,
Line 54, "WIC class" should read --MHC class--.

Signed and Sealed this
Thirty-first Day of July, 2012

David J. Kappos
*Director of the United States Patent and Trademark Office*

Column 21,
Line 23, "anti-Akt-F'(Threo)" should read --anti-Akt-P(Threo)--.
Line 47, "specific for Ala" should read --specific for Akt--.
Lines 49-50, "and rc-probed" should read --and re-probed--.
Lines 50-51, "and a tubulin" should read --and α tubulin--.

Column 22,
Line 1, "INK effector" should read --NK effector--.
Line 37, "SI-HP binds" should read --SHIP binds--.

Column 23,
Line 8, "(125I-dUrd) is" should read --($^{125}$I-dUrd) is--.

Column 24,
Line 19, "on SHIP NK" should read --on SHIP$^{-/-}$ NK--.
Lines 44-45, "(Mac-1$^+$/Gr-1') or T cells (CD3) in" should read --(Mac-1$^+$/Gr-1$^+$) or T cells (CD3$^+$) in--.
Line 60, "SHIP died" should read --SHIP$^{+/+}$ mice died--.

Column 25,
Line 27, "self WIC ligands" should read --self MHC ligands--.

Column 26,
Line 31, "H2p, H2u" should read --H2p, H2k, H2u--.
Line 46, "SHIP hosts" should read --SHIP$^{+/+}$ hosts--.

UNITED STATES PATENT AND TRADEMARK OFFICE
CERTIFICATE OF CORRECTION

| | | |
|---|---|---|
| PATENT NO. | : 8,163,710 B2 | Page 1 of 1 |
| APPLICATION NO. | : 12/651809 | |
| DATED | : April 24, 2012 | |
| INVENTOR(S) | : William G. Kerr | |

It is certified that error appears in the above-identified patent and that said Letters Patent is hereby corrected as shown below:

In the Specification

Column 1,
Lines 22-27, "This invention was made with government support under grant DK54767awarded by the National Institutes of Health and National Institute of Diabetes and Digestive and Kidney Diseases, and by grant NS27405 awarded by the National Institute of Neurological Disorders and Stroke. The government has certain rights in the invention."

Should read:
--This invention was made with government support DK054767 awarded by the National Institutes of Health. The government has certain rights to the invention.--

Signed and Sealed this
Ninth Day of May, 2017

Michelle K. Lee
*Director of the United States Patent and Trademark Office*

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: forward primer for 5kB SHIP allele

<400> SEQUENCE: 1
agtcacgtcc caccatccta tg                                                22

<210> SEQ ID NO 2
<211> LENGTH: 23
<212> TYPE: DNA
<213> ORGANISM: Artificial Sequence
<220> FEATURE:
<223> OTHER INFORMATION: reverse primer for 5kB SHIP allele

<400> SEQUENCE: 2
ccacaagtga tgctaagaga tgc                                               23

<210> SEQ ID NO 3
<211> LENGTH: 20
<212> TYPE: DNA
<213> ORGANISM: Artificial Sequence
<220> FEATURE:
<223> OTHER INFORMATION: forward primer for 0.8kB SHIP allele

<400> SEQUENCE: 3
atgaagggtc ccttgtagag                                                   20

<210> SEQ ID NO 4
<211> LENGTH: 20
<212> TYPE: DNA
<213> ORGANISM: Artificial Sequence
<220> FEATURE:
<223> OTHER INFORMATION: reverse primer for 0.8kB SHIP allele

<400> SEQUENCE: 4
ctgtgagcaa cactattccc                                                   20